United States Patent
Ito

(10) Patent No.: US 8,343,696 B2
(45) Date of Patent: Jan. 1, 2013

(54) COLORED CURABLE COMPOSITION, FLUORINE-CONTAINING DIPYRROMETHENE COMPOUND AND TAUTOMER THEREOF, AND FLUORINE-CONTAINING DIPYRROMETHENE METAL COMPLEX AND TAUTOMER THEREOF, AND COLOR FILTER USING THE SAME AND METHOD FOR PRODUCING THE COLOR FILTER

(75) Inventor: Junichi Ito, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 649 days.

(21) Appl. No.: 12/566,700

(22) Filed: Sep. 25, 2009

(65) Prior Publication Data
US 2010/0081071 A1 Apr. 1, 2010

(30) Foreign Application Priority Data
Sep. 30, 2008 (JP) .................. 2008-254529

(51) Int. Cl.
G02B 5/20 (2006.01)
G03F 7/00 (2006.01)
(52) U.S. Cl. .......................... 430/7; 430/270.1
(58) Field of Classification Search .................. None
See application file for complete search history.

(56) References Cited

U.S. PATENT DOCUMENTS

| | | | | |
|---|---|---|---|---|
| 6,106,999 A * | 8/2000 | Ogiso et al. | ................. | 430/281.1 |
| 2008/0076044 A1 | 3/2008 | Mizukawa et al. | | |
| 2010/0055582 A1* | 3/2010 | Mizukawa et al. | ............... | 430/7 |

FOREIGN PATENT DOCUMENTS

| JP | 6-75375 A | 3/1994 |
|---|---|---|
| JP | 11-352685 A | 12/1999 |
| JP | 11-352686 A | 12/1999 |
| JP | 2000-19729 A | 1/2000 |
| JP | 2000-19738 A | 1/2000 |
| JP | 3279035 B2 | 4/2002 |
| JP | 2002-236360 A | 8/2002 |
| JP | 3324279 B2 | 9/2002 |
| JP | 2009-031713 A * | 2/2009 |

* cited by examiner

*Primary Examiner* — John A. McPherson
(74) *Attorney, Agent, or Firm* — SOLARIS Intellectual Property Group, PLLC

(57) ABSTRACT

A colored curable composition contains a dipyrromethene metal complex compound formed from a fluorine-containing dipyrromethene compound represented by Formula (1) and a metal or metal compound. ($R_1$ to $R_7$: H or substituent (at least one of $R_1$ to $R_7$ includes a substituent represented by Formula (2)); $R_g$: H or substituent; $a \geq 1$; $R_f$: a fluorine atom, fluorine-containing alkyl group having 1 to 4 carbon atoms, fluorine-containing aryl group, fluorine-containing alkoxy group having 1 to 4 carbon atoms, fluorine-containing alkylsulfonamido group having 1 to 4 carbon atoms, or fluorine-containing arylsulfonamido group; m: 1 to 5; n: 0 to 4; L: single bond, O, S, NH, R—NH(R: alkylene), —Ar—NH— (Ar: arylene), CO, COO, OCO, *COS, *SCO, *CONH, *NHCO, *NHSO$_2$, SO, SO$_2$, *SO$_2$NH, an alkylene chain having 1 to 4 carbon atoms or arylene group.)

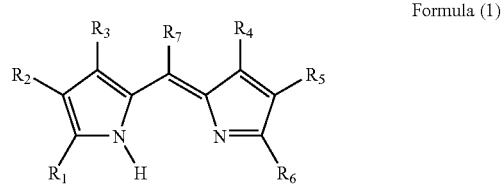

Formula (1)

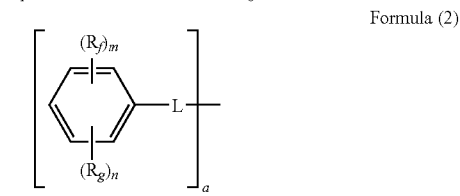

Formula (2)

7 Claims, No Drawings

COLORED CURABLE COMPOSITION, FLUORINE-CONTAINING DIPYRROMETHENE COMPOUND AND TAUTOMER THEREOF, AND FLUORINE-CONTAINING DIPYRROMETHENE METAL COMPLEX AND TAUTOMER THEREOF, AND COLOR FILTER USING THE SAME AND METHOD FOR PRODUCING THE COLOR FILTER

CROSS-REFERENCE TO RELATED APPLICATION

This application claims priority under 35 USC 119 from Japanese Patent Application No. 2008-254529 filed on Sep. 30, 2008, the disclosure of which is incorporated by reference herein.

BACKGROUND OF THE INVENTION

Field of the Invention

The present invention relates to a colored curable composition, a fluorine-containing dipyrromethene compound and a tautomer thereof, a fluorine-containing dipyrromethene metal complex and a tautomer thereof, and a color filter and a method for producing the color filter.

A pigment dispersion method has been used as one of the methods for producing color filters for use in liquid crystal display elements or solid-state image sensors. The pigment dispersion method is a method of producing a color filter by photolithography, by using a radiation-sensitive colored composition containing a pigment dispersed in various types of photosensitive compositions. This method, which uses a pigment and provides a color filter resistant to light and heat and favorable in positioning accuracy because of patterning by photolithography, has been used widely as a favorable method in producing a conventional size of patterns such as color filters for color displays.

In preparing a color filter by the pigment dispersion method, the radiation-sensitive composition is first coated on a substrate with a spin coater or roll coater and then dried to form a coating film. Subsequently, colored pixels are obtained by patterned-exposure and development of the coating film. The color filter can be prepared by repeating this operation a number of times corresponding to the number of hues.

In recent years, higher-definition color filters for solid-state image sensors such as CCDs has been desired. With an increase in definition, the size of a pattern decreases, but further improvement of definition is difficult with conventional pigment dispersion methods. One of the reasons for this is that coarse particles formed by co-aggregation of pigment particles cause unevenness of color in a fine pattern. Therefore, conventionally used pigment dispersion methods may not be suitable for applications requiring a fine pattern, such as solid-state image sensors.

In order to achieve higher-definition, the use of a dye as a coloring material has been studied (see, for example, Japanese Patent Application Laid-Open (JP-A) No. 6-75375). However, a dye-containing curable composition has the following problems.

(1) Dyes in a molecular dispersion state are inferior to pigments, which are generally in a molecular assembly state, in terms of light-fastness and heat resistance.

(2) In a general dye, since the molecules thereof have wide π conjugate planes and low solubility in aqueous alkaline solutions or organic solvents (hereinafter also referred to as a "solvent"), it is difficult to obtain a liquid curable composition having a desired spectrum.

(3) Dyes often exhibit interaction with other ingredients in the curable composition in many cases, and it is difficult to adjust the solubility (developability) of a cured area and a non-cured area.

(4) When a dye has a low molar absorption coefficient ($\epsilon$), a large amount of dye need to be added. Therefore, the amount of other ingredients such as a polymerizable compound (monomer), a binder or a photopolymerization initiator in the curable composition decreases, thereby reducing curing properties of the composition, heat resistance after curing, and developability of a (non) cured area.

Dipyrromethene metal complexes have been examined as dyes for solving the problems relating to the light-fastness and heat resistance of the dyes of the item (1) above and to the molar absorption coefficient ($\epsilon$) of the dyes of the item (4) above (see, for example, the specification of U.S. Patent Application Publication No. 2008/0076044, which is incorporated herein by reference). The dipyrromethene metal complex is a functional compound for use in a sensitizer of a radical polymerization initiator in a visible-light polymerizable composition (see, for example, Japanese Patent (JP) Nos. 3279035 and 3324279 and JP-A Nos. 11-352685, 11-352686, 2000-19729, 2000-19738, and 2002-236360). The properties of the dipyrromethene metal complexes, such as excellent light-fastness and excellent heat resistance, high molar absorption coefficient ($\epsilon$), and preferable absorption properties in terms of color reproducibility, have been reported (see, for example, the specification of U.S. patent Application Publication No. 2008/0076044).

In addition, as described in item (2) above, an increase in the solubility of a dye have in a solvent has been desired. Further, a color filter for solid-state image sensors formed into a thin film having a thickness of 1 μm or less so as to obtain a high definition pattern, has been desired. However, in order to achieve a desired absorption by the thin film, it is necessary to add a large amount of dye to a curable composition and the dye concentration in the curable composition increases.

SUMMARY OF THE INVENTION

Aspects of the invention include those described below.
<1> A colored curable composition containing at least one of a dipyrromethene metal complex compound or a tautomer thereof, in which the at least one of the dipyrromethene metal complex compound or the tautomer thereof is formed from a fluorine-containing dipyrromethene compound represented by the following Formula (1) and a metal or metal compound.

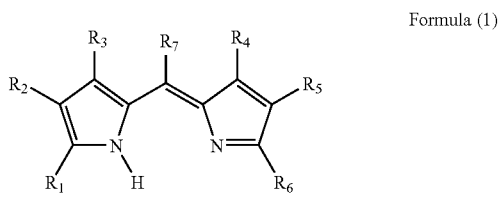

Formula (1)

In Formula (1), $R_1$, $R_2$, $R_3$, $R_4$, $R_5$, $R_6$, and $R_7$ each independently represent a hydrogen atom or a substituent, and at least one hydrogen atom in at least one of $R_1$ to $R_7$ is replaced by a substituent represented by the following Formula (2).

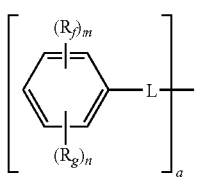

Formula (2)

In Formula (2), a represents an integer of 1 or more; each $R_f$ independently represents a fluorine atom, a fluorine-containing alkyl group having 1 to 4 carbon atoms, a fluorine-containing aryl group, a fluorine-containing alkoxy group having 1 to 4 carbon atoms, a fluorine-containing alkylsulfonamido group having 1 to 4 carbon atoms, or a fluorine-containing arylsulfonamido group; m represents an integer of from 1 to 5; each $R_g$ independently represents a hydrogen atom or a substituent; n represents an integer of from 0 to 4; and L represents a single bond, an oxygen atom, a sulfur atom, —NH—, —R—NH— (where, R represents an alkylene group), —Ar—NH— (where, Ar represents an arylene group), a carbonyl group, an ester group, an oxycarbonyl group, a thioester group, a thiocarbonyl group, *—CONH—, *—NHCO—, *—NHSO$_2$—, a sulfinyl group, a sulfonyl group, *—SO$_2$NH—, a substituted or unsubstituted alkylene chain having 1 to 4 carbon atoms, or a substituted or unsubstituted arylene group (where, * represents a bond linking to Formula (1)).

<2> The colored curable composition according to <1>, in which the dipyrromethene metal complex compound is represented by the following Formula (3).

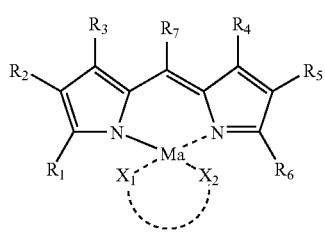

Formula (3)

In Formula (3), $R_1$, $R_2$, $R_3$, $R_4$, $R_5$, $R_6$, and $R_7$ each independently represent a hydrogen atom or a substituent, and at least one hydrogen atom in at least one of $R_1$ to $R_7$ is replaced by a substituent represented by Formula (2). In Formula (2), a represents an integer of 1 or more; each $R_f$ independently represents a fluorine atom, a fluorine-containing alkyl group having 1 to 4 carbon atoms, a fluorine-containing aryl group, a fluorine-containing alkoxy group having 1 to 4 carbon atoms, a fluorine-containing alkylsulfonamido group having 1 to 4 carbon atoms, or a fluorine-containing arylsulfonamido group; m represents an integer of from 1 to 5; each $R_g$ independently represents a hydrogen atom or a substituent; n represents an integer of from 0 to 4; and L represents a single bond, an oxygen atom, a sulfur atom, —NH—, —R—NH— (where, R represents an alkylene group), —Ar—NH— (where, Ar represents an arylene group), a carbonyl group, an ester group, an oxycarbonyl group, a thioester group, a thiocarbonyl group, *—CONH—, *—NHCO—, *—NHSO$_2$—, a sulfinyl group, a sulfonyl group, *—SO$_2$NH—, an alkylene chain having 1 to 4 carbon atoms, or an arylene group (where, * represents a bond linking to Formula (3)). In Formula (3), Ma represents a metal or metal compound; $X_1$ represents a group that can bind to Ma; and $X_2$ represents a group required for neutralizing the electric charge of Ma. $X_1$ and $X_2$ may be linked to each other to form a 5-, 6-, or 7-membered ring.

<3> The colored curable composition according to <1> or <2>, in which the dipyrromethene metal complex compound is represented by the following Formula (4) or Formula (5).

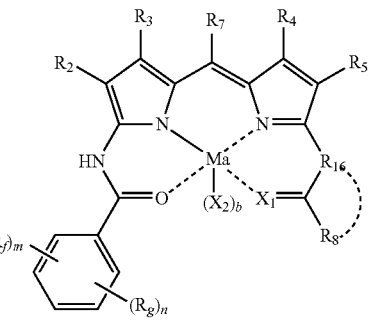

Formula (4)

In Formula (4), each $R_f$ independently represents a fluorine atom, a fluorine-containing alkyl group having 1 to 4 carbon atoms, a fluorine-containing aryl group, a fluorine-containing alkoxy group having 1 to 4 carbon atoms, a fluorine-containing alkylsulfonamido group having 1 to 4 carbon atoms, or a fluorine-containing arylsulfonamido group; m represents an integer of from 1 to 5; each $R_g$ independently represents a hydrogen atom or a substituent; n represents an integer of from 0 to 4; $R_2$, $R_3$, $R_4$, $R_5$, and $R_7$ each independently represent a hydrogen atom or a substituent; Ma represents a metal or metal compound; $X_1$ represents NY (where, Y represents a hydrogen atom, an alkyl group, an alkenyl group, an aryl group, a heterocyclic group, an acyl group, an alkylsulfonyl group, or an arylsulfonyl group), an oxygen atom, a nitrogen atom, or a sulfur atom; $R_{16}$ represents NR (where, R represents a hydrogen atom, an alkyl group, an alkenyl group, an aryl group, a heterocyclic group, an acyl group, an alkylsulfonyl group, or an arylsulfonyl group) or a carbon atom; and $R_8$ represents a hydrogen atom, an alkyl group, an alkenyl group, an aryl group, a heterocyclic group, an alkoxy group, an aryloxy group, an alkylamino group, an arylamino group, or a heterocyclic amino group. $R_{16}$ and $R_8$ may be linked to each other to form a 5-, 6-, or 7-membered ring. $X_2$ represents a group required for neutralizing the electric charge of Ma and b represents 0, 1, or 2.

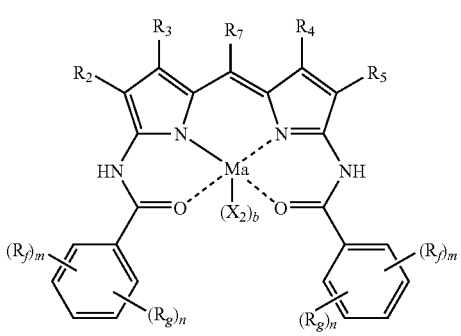

Formula (5)

In Formula (5), each $R_f$ independently represents a fluorine atom, a fluorine-containing alkyl group having 1 to 4 carbon atoms, a fluorine-containing aryl group, a fluorine-containing alkoxy group having 1 to 4 carbon atoms, a fluorine-containing alkylsulfonamido group having 1 to 4 carbon atoms, or a fluorine-containing arylsulfonamido group; m represents an integer of from 1 to 5; each $R_g$ independently represents a hydrogen atom or a substituent; n represents an integer of from 0 to 4; $R_2$, $R_3$, $R_4$, $R_5$, and $R_7$ each independently represent a hydrogen atom or a substituent; Ma represents a metal or metal compound; $X_2$ represents a group required for neutralizing the electric charge of Ma; and b represents 0, 1, or 2.

<4> The colored curable composition according to <2> or <3>, in which Ma is Zn, Co, V=O, or Cu.

<5> The colored curable composition according to <4>, in which Ma is Zn.

<6> A fluorine-containing dipyrromethene compound represented by the following Formula (6) or Formula (7) or a tautomer thereof

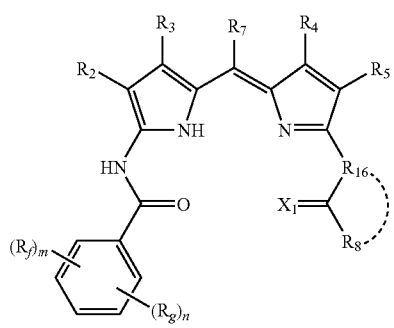

Formula (6)

In Formula (6), each $R_f$ independently represents a fluorine atom, a fluorine-containing alkyl group having 1 to 4 carbon atoms, a fluorine-containing aryl group, a fluorine-containing alkoxy group having 1 to 4 carbon atoms, a fluorine-containing alkylsulfonamido group having 1 to 4 carbon atoms, or a fluorine-containing arylsulfonamido group; m represents an integer of from 1 to 5; each $R_g$ independently represents a hydrogen atom or a substituent; n represents an integer of from 0 to 4; $R_2$, $R_3$, $R_4$, $R_5$, and $R_7$ each independently represent a hydrogen atom or a substituent; $X_1$ represents NY (where, Y represents a hydrogen atom, an alkyl group, an alkenyl group, an aryl group, a heterocyclic group, an acyl group, an alkylsulfonyl group, or an arylsulfonyl group), an oxygen atom, a nitrogen atom, or a sulfur atom; $R_{16}$ represents NR (where, R represents a hydrogen atom, an alkyl group, an alkenyl group, an aryl group, a heterocyclic group, an acyl group, an alkylsulfonyl group, or an arylsulfonyl group) or a carbon atom; and $R_8$ represents a hydrogen atom, an alkyl group, an alkenyl group, an aryl group, a heterocyclic group, an alkoxy group, an aryloxy group, an alkylamino group, an arylamino group, or a heterocyclic amino group. $R_{16}$ and $R_8$ may be linked to each other to form a 5-, 6-, or 7-membered ring.

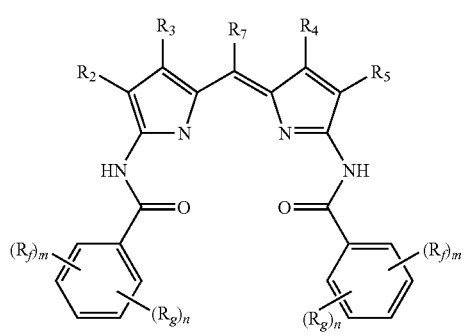

Formula (7)

In Formula (7), each $R_f$ independently represents a fluorine atom, a fluorine-containing alkyl group having 1 to 4 carbon atoms, a fluorine-containing aryl group, a fluorine-containing alkoxy group having 1 to 4 carbon atoms, a fluorine-containing alkylsulfonamido group having 1 to 4 carbon atoms, or a fluorine-containing arylsulfonamido group; m represents an integer of from 1 to 5; each $R_g$ independently represents a hydrogen atom or a substituent; n represents an integer of from 0 to 4; and $R_2$, $R_3$, $R_4$, $R_5$, and $R_7$ each independently represent a hydrogen atom or a substituent.

<7> A fluorine-containing dipyrromethene metal complex compound represented by Formula (4) or Formula (5) or a tautomer thereof

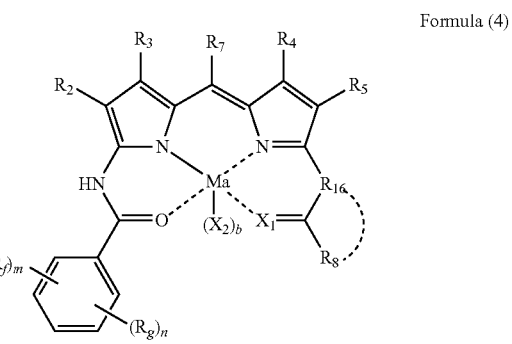

Formula (4)

In Formula (4), each $R_f$ independently represents a fluorine atom, a fluorine-containing alkyl group having 1 to 4 carbon atoms, a fluorine-containing aryl group, a fluorine-containing alkoxy group having 1 to 4 carbon atoms, a fluorine-containing alkylsulfonamido group having 1 to 4 carbon atoms, or a fluorine-containing arylsulfonamido group; m represents an integer of from 1 to 5; each $R_g$ independently represents a hydrogen atom or a substituent; n represents an integer of from 0 to 4; $R_2$, $R_3$, $R_4$, $R_5$, and $R_7$ each independently represent a hydrogen atom or a substituent; Ma represents a metal or metal compound; $X_1$ represents NY (where, Y represents a hydrogen atom, an alkyl group, an alkenyl group, an aryl group, a heterocyclic group, an acyl group, an alkylsulfonyl group, or an arylsulfonyl group), an oxygen atom, a nitrogen atom, or a sulfur atom; $R_{16}$ represents NR (where, R represents a hydrogen atom, an alkyl group, an alkenyl group, an aryl group, a heterocyclic group, an acyl group, an alkylsulfonyl group, or an arylsulfonyl group) or a carbon atom; and $R_8$ represents a hydrogen atom, an alkyl group, an alkenyl group, an aryl group, a heterocyclic group, an alkoxy group, an aryloxy group, an alkylamino group, an arylamino group, or a heterocyclic amino group. $R_{16}$ and $R_8$ may be linked to each other to form a 5-, 6-, or 7-membered ring. $X_2$ represents a group required for neutralizing the electric charge of Ma and b represents 0, 1, or 2.

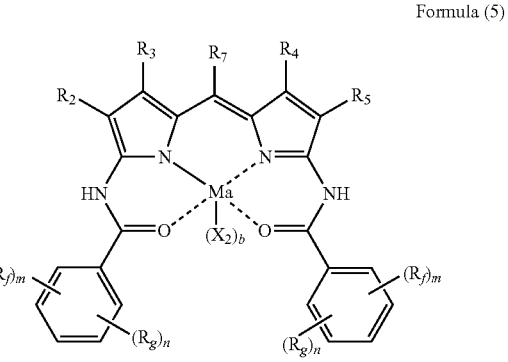

Formula (5)

In Formula (5), each $R_f$ independently represents a fluorine atom, a fluorine-containing alkyl group having 1 to 4 carbon atoms, a fluorine-containing aryl group, a fluorine-containing alkoxy group having 1 to 4 carbon atoms, a fluorine-containing alkylsulfonamido group having 1 to 4 carbon atoms, or a fluorine-containing arylsulfonamido group; m represents an integer of from 1 to 5; each $R_g$ independently represents a hydrogen atom or a substituent; n represents an integer of from 0 to 4; $R_2$, $R_3$, $R_4$, $R_5$, and $R_7$ each independently represent a hydrogen atom or a substituent; Ma represents a metal or metal compound; $X_2$ represents a group required for neutralizing the electric charge of Ma; and b represents 0, 1, or 2.

<8> A color filter formed from the colored curable composition according to any one of <1> to <5>.

<9> A method for producing a color filter, including applying the colored curable composition according to any one of <1> to <5> to form a coating layer, exposing the coating layer through a mask, and developing the coating layer to form a pattern image.

DETAILED DESCRIPTION OF THE INVENTION

Since the solvent solubility of known dipyrromethene metal complexes is insufficient, it is difficult to apply a known dipyrromethene metal complex as a coloring material in place of a pigment. In particular, when a thin film is formed from the dye, the amount of the dye relative to the total amount of the film inevitably increases as the thickness of the film decreases, whereby sufficient dissolution cannot be achieved and a desired dye concentration in the film is difficult to obtain. In order to obtain a high-definition pattern with a thin film having a thickness of 1 µm or less (the concentration of dye in the thin film preferably being 35% by mass or more) such as for a color filter for a solid state image sensor, a degree of solvent solubility is required with which the solvent solubility of the dye must be sufficient to enable complete dissolution even in a composition with a high dye content.

The invention has been made in view of the above-described circumstances, and provides a novel dipyrromethene metal complex compound. The invention also provides a dipyrromethene metal complex compound and a tautomer thereof, which have excellent solvent solubility and fastness and have a high absorption coefficient.

In addition, the invention provides a colored curable composition that can be prepared to have a high dye concentration (preferably 35% by mass or more), can be formed as a thin film with a high absorption coefficient, and has favorable color density and color purity.

The invention also provides a color filter that is a thin layer, that has high color density, and that has excellent color reproduction properties and color fastness (particularly light-fastness and heat resistance), and provides a method for producing the color filter.

As a result of detailed study of various coloring materials by the present inventor, it has been found that a specific dipyrromethene metal complex compound has a high solvent solubility, exhibits a favorable hue as a coloring material for coloring a pattern, has a high absorption coefficient and has favorable fastness to heat and light. Based on these findings, the invention has been accomplished.

In view of the above, the present invention is particularly effective in forming a color filter for solid-state image sensors, in which a pixel pattern is formed as a thin film (for example, with a thickness of 1 µm or less), in which a high-definition pixel pattern having a size as small as 2 µm or less is required (for example, a side length of the pixel pattern viewed from the substrate normal direction being 0.5 µm to 2.0 µm), and in which a favorable rectangular sectional profile is required.

According to the present invention, a novel dipyrromethene metal complex compound is provided. In addition, the present invention provides a dipyrromethene metal complex compound and a tautomer thereof, which have excellent solvent solubility and fastness and have a high absorption coefficient. As a result, the dipyrromethene metal complex compound of the invention can be prepared in a solution at a higher concentration (for example, 35% by mass or more) compared with a conventional dipyrromethene compound. In addition, the present invention provides a colored curable composition that can be prepared to have a high dye concentration (preferably 35% by mass or more), that has a high absorption coefficient which can be formed in a thin film, and has favorable color density and color purity. By using the colored curable composition of the invention, as compared with conventional ones, a thinner (preferably 1 µm or less) pixel pattern with higher definition can be formed.

The invention provides a color filter that is a thin layer, that has high color density, and that has excellent color reproduction properties and fastness (particularly light-fastness, heat resistance), and provides a method for producing the color filter.

Hereinafter, the colored curable composition of the invention, a color filter using the colored curable composition, and a method for producing the color filter will be described in detail. In addition, the fluorine-containing dipyrromethene compound, and the fluorine-containing dipyrromethene metal complex compound and the tautomer thereof of the invention will be described in detail.

Colored Curable Composition and Fluorine-Containing Dipyrromethene Compound

The colored curable composition of the invention contains, as a coloring material, at least one of a fluorine-containing dipyrromethene metal complex compound or a tautomer thereof (hereinafter sometimes referred to as a "specific metal complex compound-1"), which is formed with the compound represented by Formula (1) (hereinafter sometimes referred to as a "specific compound-1") and a metal or metal compound. The colored curable composition of the invention may further include other ingredients such as a binder, if necessary.

The colored curable composition of the invention is preferably a "photosensitive" composition and is more preferably a "ultraviolet-sensitive" composition.

Coloring Material

First, the fluorine-containing dipyrromethene metal complex compound or a tautomer thereof (the specific metal complex compound-1) formed with the compound represented by Formula (1) (the specific compound-1) and the metal or metal compound will be described.

Compound Represented by Formula (1)

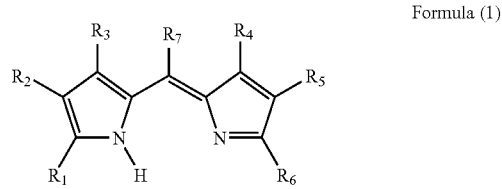

Formula (1)

In Formula (1), $R_1$, $R_2$, $R_3$, $R_4$, $R_5$, $R_6$, and $R_7$ each independently represent a hydrogen atom or a substituent, at least one hydrogen atom in at least one of $R_1$ to $R_7$ is replaced by a substituent represented by the following Formula (2).

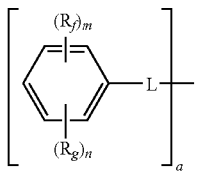

Formula (2)

In Formula (2), a represents an integer of 1 or more; each $R_f$ independently represents a fluorine atom, a fluorine-containing alkyl group having 1 to 4 carbon atoms, a fluorine-containing aryl group, a fluorine-containing alkoxy group having 1 to 4 carbon atoms, a fluorine-containing alkylsulfonamido group having 1 to 4 carbon atoms, or a fluorine-containing arylsulfonamido group; m represents an integer of from 1 to 5; each $R_g$ independently represents a hydrogen atom or a substituent; n represents an integer of from 0 to 4; and L represents a single bond, an oxygen atom, a sulfur atom, —NH—, —R—NH— (where, R represents an alkylene group), —Ar—NH— (where, Ar represents an arylene group), a carbonyl group, an ester group, an oxycarbonyl group, a thioester group, a thiocarbonyl group, *—CONH—, *—NHCO—, *—NHSO$_2$—, a sulfinyl group, a sulfonyl group, *—SO$_2$NH—, a substituted or unsubstituted alkylene chain having 1 to 4 carbon atoms, or a substituted or unsubstituted arylene group (where, * represents a bond linking to Formula (1)).

Here, the term "substituent" used in the description of the compound represented by Formula (1) is explained.

Examples of the substituent represented by $R_1$ to $R_7$ in Formula (1) include:

a halogen atom such as a fluorine atom, a chlorine atom or a bromine atom;

an alkyl group (preferably a linear, branched or cyclic alkyl group having 1 to 48 carbon atoms, more preferably having 1 to 24 carbon atoms) such as a methyl group, an ethyl group, a propyl group, an isopropyl group, a butyl group, a t-butyl group, a pentyl group, a hexyl group, a heptyl group, an octyl group, a 2-ethylhexyl group, a dodecyl group, a hexadecyl group, a cyclopropyl group, a cyclopentyl group, a cyclohexyl group, a 1-norbornyl group or a 1-adamantyl group;

an alkenyl group (preferably an alkenyl group having 2 to 48 carbon atoms, more preferably having 2 to 18 carbon atoms) such as a vinyl group, an allyl group or a 3-buten-1-yl group);

an aryl group (preferably an aryl group having 6 to 48 carbon atoms, more preferably having 6 to 24 carbon atoms) such as a phenyl group or a naphthyl group;

a heterocyclic group (preferably a heterocyclic group having 1 to 32 carbon atoms, more preferably having 1 to 18 carbon atoms) such as a 2-thienyl group, a 4-pyridyl group, a 2-furyl group, a 2-pyrimidinyl group, a 1-pyridyl group, a 2-benzothiazolyl group, a 1-imidazolyl group, a 1-pyrazolyl group or a benzotriazole-1-yl group;

a silyl group (preferably a silyl group having 3 to 38 carbon atoms, more preferably having 3 to 18 carbon atoms) such as a trimethylsilyl group, a triethylsilyl group, a tributylsilyl group, a t-butyldimethylsilyl group or a t-hexyldimethylsilyl group;

a hydroxyl group, a cyano group, a nitro group;

an alkoxy group (preferably an alkoxy group having 1 to 48 carbon atoms, more preferably having 1 to 24 carbon atoms) such as a methoxy group, an ethoxy group, a 1-butoxy group, a 2-butoxy group, an isopropoxy group, a t-butoxy group, a dodecyloxy group or a cycloalkyloxy group (such as a cyclopentyloxy group or a cyclohexyloxy group);

an aryloxy group (preferably an aryloxy group having 6 to 48 carbon atoms, more preferably having 6 to 24 carbon atoms) such as a phenoxy group or a 1-naphthoxy group;

a heterocyclic oxy group (preferably a heterocyclic oxy group having 1 to 32 carbon atoms, more preferably having 1 to 18 carbon atoms) such as a 1-phenyltetrazole-5-oxy group or a 2-tetrahydropyranyloxy group;

a silyloxy group (preferably a silyloxy group having 1 to 32 carbon atoms, more preferably having 1 to 18 carbon atoms) such as a trimethylsilyloxy group, a t-butyldimethylsilyloxy group or a diphenylmethylsilyloxy group;

an acyloxy group (preferably an acyloxy group having 2 to 48 carbon atoms, more preferably having 2 to 24 carbon atoms) such as an acetoxy group, a pivaloyloxy group, a benzoyloxy group or a dodecanoyloxy group;

an alkoxycarbonyloxy group (preferably an alkoxycarbonyloxy group having 2 to 48 carbon atoms, more preferably having 2 to 24 carbon atoms) such as an ethoxycarbonyloxy group, a t-butoxycarbonyloxy group, or a cycloalkyloxycarbonyloxy group (such as a cyclohexyloxycarbonyloxy group);

an aryloxycarbonyloxy group (preferably an aryloxycarbonyloxy group having 7 to 32 carbon atoms, more preferably having 7 to 24 carbon atoms) such as a phenoxycarbonyloxy group;

a carbamoyloxy group (preferably a carbamoyloxy group having 1 to 48 carbon atoms, more preferably having 1 to 24 carbon atoms) such as an N,N-dimethylcarbamoyloxy group, an N-butylcarbamoyloxy group, an N-pheylcarbamoyloxy group or an N-ethyl-N-pheylcarbamoyloxy group;

a sulfamoyloxy group (preferably a sulfamoyloxy group having 1 to 32 carbon atoms, more preferably having 1 to 24 carbon atoms) such as an N,N-diethylsulfamoyloxy group or an N-propylsulfamoyloxy group;

an alkylsulfonyloxy group (preferably an alkylsulfonyloxy group having 1 to 38 carbon atoms, more preferably having 1 to 24 carbon atoms) such as a methylsulfonyloxy group, a hexadecylsulfonyloxy group or a cyclohexylsulfonyloxy group;

an arylsulfonyloxy group (preferably an arylsulfonyloxy group having 6 to 32 carbon atoms, more preferably having 6 to 24 carbon atoms) such as a phenylsulfonyloxy group;

an acyl group (preferably an acyl group having 1 to 48 carbon atoms, more preferably having 1 to 24 carbon atoms) such as a formyl group, an acetyl group, a pivaloyl group, a benzoyl group, a tetradecanoyl group or a cyclohexanoyl group;

an alkoxycarbonyl group (preferably an alkoxycarbonyl group having 2 to 48 carbon atoms, more preferably having 2 to 24 carbon atoms) such as a methoxycarbonyl group, an ethoxycarbonyl group, an octadecyloxycarbonyl group, a cyclohexyloxycarbonyl group or a 2,6-di-tert-butyl-4-methylcyclohexyloxycarbonyl group;

an aryloxycarbonyl group (preferably an aryloxycarbonyl group having 7 to 32 carbon atoms, more preferably having 7 to 24 carbon atoms) such as a phenoxycarbonyl group;

a carbamoyl group (preferably a carbamoyl group having 1 to 48 carbon atoms, more preferably having 1 to 24 carbon atoms) such as a carbamoyl group, an N,N-diethylcarbamoyl group, an N-ethyl-N-octylcarbamoyl group, an N,N-dibutylcarbamoyl group, a N-propylcarbamoyl group, an N-phenylcarbamoyl group, an N-methyl-N-phenylcarbamoyl group or an N,N-dicyclohexylcarbamoyl group;

an amino group (preferably an amino group having 32 or fewer carbon atoms, more preferably having 24 or fewer carbon atoms) such as an amino group, a methylamino group, an N,N-dibutylamino group, a tetradecylamino group, a 2-ethylhexylamino group or a cyclohexylamino group;

an anilino group (preferably an anilino group having 6 to 32 carbon atoms, more preferably 6 to 24 carbon atoms) such as an anilino group or an N-methyl anilino group;

a heterocyclic amino group (preferably a heterocyclic amino group having 1 to 32 carbon atoms, more preferably 1 to 18 carbon atoms) such as a 4-pyridylamino group;

a carbonamido group (preferably a carbonamido group having 2 to 48 carbon atoms, more preferably 2 to 24 carbon atoms) such as an acetamido group, a benzamido group, a tetradecanamido group, a pivaloylamido group or a cyclohexaneamido group;

a ureido group (preferably a ureido group having 1 to 32 carbon atoms, more preferably having 1 to 24 carbon atoms) such as a ureido group, an N,N-dimethylureido group, or an N-phenylureido group;

an imido group (preferably an imido group having 36 or fewer carbon atoms, more preferably having 24 or fewer carbon atoms) such as an N-succinimido group or an N-phthalimido group;

an alkoxycarbonylamino group (preferably an alkoxycarbonylamino group having 2 to 48 carbon atoms, more preferably having 2 to 24 carbon atoms) such as a methoxycarbonylamino group, an ethoxycarbonylamino group, a t-butoxycarbonylamino group, an octadecyloxycarbonylamino group or a cyclohexyloxycarbonylamino group;

an aryloxycarbonylamino group (preferably an aryloxycarbonylamino group having 7 to 32 carbon atoms, more preferably having 7 to 24 carbon atoms) such as a phenoxycarbonylamino group;

a sulfonamido group (preferably a sulfonamido group having 1 to 48 carbon atoms, more preferably having 1 to 24 carbon atoms) such as a methanesulfonamido group, a butanesulfonamido group, a benzenesulfonamido group, a hexadecanesulfonamido group or a cyclohexanesulfonamido group;

a sulfamoylamino group (preferably a sulfamoylamino group having 1 to 48 carbon atoms, more preferably having 1 to 24 carbon atom) such as an N,N-dipropylsulfamoylamino group or an N-ethyl-N-dodecylsulfamoylamino group;

an azo group (preferably an azo group having 1 to 32 carbon atoms, more preferably having 1 to 24 carbon atoms) such as a phenylazo group or a 3-pyrazolylazo group;

an alkylthio group (preferably an alkylthio group having 1 to 48 carbon atoms, more preferably having 1 to 24 carbon atoms) such as a methylthio group, an ethylthio group, an octylthio group or a cyclohexylthio group;

an arylthio group (preferably an arylthio group having 6 to 48 carbon atoms, more preferably having 6 to 24 carbon atoms) such as a phenylthio group;

a heterocyclic thio group (preferably a heterocyclic thio group having 1 to 32 carbon atoms, more preferably having 1 to 18 carbon atoms) such as a 2-benzothiazolylthio group, a 2-pyridylthio group or a 1-phenyltetrazolylthio group;

an alkylsulfinyl group (preferably an alkylsulfinyl group having 1 to 32 carbon atoms, more preferably having 1 to 24 carbon atoms) such as a dodecanesulfinyl group;

an arylsulfinyl group (preferably an arylsulfinyl group having 6 to 32 carbon atoms, more preferably having 6 to 24 carbon atoms) such as a phenylsulfinyl group;

an alkylsulfonyl group (preferably an alkylsulfonyl group having 1 to 48 carbon atoms, more preferably having 1 to 24 carbon atoms) such as a methylsulfonyl group, an ethylsulfonyl group, a propylsulfonyl group, a butylsulfonyl group, an isopropylsulfonyl group, a 2-ethylhexylsulfonyl group, a hexadecylsulfonyl group, an octylsulfonyl group or an cyclohexylsulfonyl group;

an arylsulfonyl group (preferably an arylsulfonyl group having 6 to 48 carbon atoms, more preferably having 6 to 24 carbon atoms) such as a phenylsulfonyl group or a 1-naphthylsulfonyl group;

a sulfamoyl group (preferably a sulfamoyl group having 32 or fewer carbon atoms, more preferably having 24 or fewer carbon atoms) such as a sulfamoyl group, an N,N-dipropylsulfamoyl group, an N-ethyl-N-dodecylsulfamoyl group, an N-ethyl-N-phenylsulfamoyl group or an N-cyclohexylsulfamoyl group;

a sulfo group;

a sulfonyl group (preferably a sulfonyl group having 1 to 32 carbon atoms, more preferably having 1 to 24 carbon atoms) such as a phenoxyphosphonyl group, an octyloxyphosphonyl group or a phenylsulfonyl group; and a phosphinoylamino group (preferably a phosphinoylamino group having 1 to 32 carbon atoms, more preferably having 1 to 24 carbon atoms) such as a diethoxyphosphinoylamino group or a dioctyloxyphosphinoylamino group.

When the substituent represented by any of $R_1$ to $R_7$ in Formula (1) is a group that can be substituted, the substituent represented by any of $R_1$ to $R_7$ may have a further substituent (i.e., the substituent represented by any of $R_1$ to $R_7$ may itself has a substituent), in which the further substituent may be selected from the range of substituents represented by $R_1$ to $R_7$ described above. When the substituent represented by any of $R_1$ to $R_7$ has two or more substituents, the two or more substituents may be the same as or mutually different from one another.

In a combination of $R_1$ and $R_2$, a combination of $R_2$ and $R_3$, a combination of $R_4$ and $R_5$, and a combination of $R_5$ and $R_6$ in Formula (1), the two members of each combination may independently be linked to each other to form a 5-, 6-, or 7-membered ring, which may be saturated or unsaturated. When the 5-, 6-, or 7-membered ring formed is a group that can be substituted, the ring may be substituted with a substituent, in which the substituent may be selected from the range of substituents represented by $R_1$ to $R_7$ described above. When the ring is substituted with two or more substituents, the two or more substituents may be the same as or mutually different from one another.

In Formula (2), examples of the fluorine-containing alkyl group having 1 to 4 carbon atoms and represented by $R_f$ include —$CF_3$, —$C_2F_5$, —$CH_2CHF_2$, —$CH_2CF_3$, —$C_3F_7$, and —$CF_2$—$CF_2$—$CF_2$—$CF_3$. Among the above, —$CF_3$ is preferable in terms of the content of fluorine atoms per molecular weight.

Examples of the fluorine-containing aryl group represented by $R_f$ include —$C_6H_4$-2-F, $C_6H_4$-3-F, —$C_6H_4$-4-F, —$C_6H_3$-2-F-3-F, —$C_6H_3$-2-F-4-F, —$C_6H_3$-2-F-5-F, —$C_6H_3$-2-F-6-F, $C_6H_3$-3-F-4-F, —$C_6H_3$-3-F-5-F, —$C_6H_2$-2-F-3-F-4-F, —$C_6H_2$-2-F-3-F-5-F, —$C_6H_2$-2-F-3-F-6-F, —$C_6H_2$-2-F-4-F-5-F, —$C_6H_2$-2-F-4-F-6-F, —$C_6H_2$-3-F-4-F-5-F, —$C_6H_2$-3-F-4-F-6-F, —$C_6H$-2-F-3-F-4-F-5-F, —$C_6H$-2-F-3-F-4-F-6-F, —$C_6H$-2-F-3-F-5-F-6-F, and —$C_6F_5$. Among the above, —$C_6H_3$-2-F-3-F, —$C_6H_3$-2-F-4-F, —$C_6H_3$-2-F-5-F, —$C_6H_3$-2-F-6-F, —$C_6H_3$-3-F-4-F, and —$C_6H_3$-3-F-5-F are preferable in terms of excellent solubility and low molecular weight.

Examples of the fluorine-containing alkoxy group having 1 to 4 carbon atoms and represented by $R_f$ include —$OCF_3$, —$OC_2F_5$, —$OCH_2CHF_2$, —$OCH_2CF_3$, —$OC_3F_7$, and —$OCF_2$—$CF_2$—$CF_2$—$CF_3$. Among the above, —$OCF_3$ is preferable in terms of the content of fluorine atoms per molecular weight.

Examples of the fluorine-containing alkylsulfonamido group represented by $R_f$ include —$NHSO_2CF_3$.

Examples of the fluorine-containing arylsulfonamido group represented by $R_f$ include —$NHSO_2C_6F_5$.

The substituent represented by $R_g$ in Formula (2) has the same definition as that of the substituents represented by $R_1$ to $R_7$ in Formula (1), and preferable examples thereof are also the same as those of the substituents represented by $R_1$ to $R_7$.

In Formula (2), L represents a single bond, an oxygen atom, a sulfur atom, —NH—, —R—NH— (where, R represents an alkylene group), —Ar—NH— (where, Ar represents an arylene group), a carbonyl group (—CO—), an ester group (—COO—), an oxycarbonyl group (—OCO—), a thioester group (*—COS—), a thiocarbonyl group (*—SCO—), *—CONH—, *—NHCO—, *—$NHSO_2$—, a sulfinyl group, a sulfonyl group, *—$SO_2NH$—, a substituted or unsubstituted alkylene chain having 1 to 4 carbon atoms, or a substituted or unsubstituted arylene group. Here, * represents a bond linking to Formula (1), where the bond is formed by replacing a hydrogen atom in any one of $R_1$ to $R_7$.

Here, examples of the alkylene group represented by R include an alkylene group in which one hydrogen atom has been removed from an alkyl group that any one of $R_1$ to $R_7$ in Formula (1) may represent. Preferable examples of the alkylene group represented by R include an alkylene group in which one hydrogen atom has been removed from an alkyl group that any one of $R_1$ to $R_7$ in Formula (1) preferably represents.

Examples of the arylene group represented by Ar include an arylene group in which one hydrogen atom has been removed from an aryl group that any one of $R_1$ to $R_7$ in Formula (1) may represent. Preferable examples of the arylene group represented by Ar include an arylene group in which one hydrogen atom has been removed from an aryl group that any one of $R_1$ to $R_7$ in Formula (1) preferably represents.

Among the above, in terms of excellent solubility and low molecular weight, the substituent represented by Formula (2) is preferably a substituent in which $R_f$ represents a fluorine atom, m represents an integer of from 1 to 5, $R_g$ represents a hydrogen atom and n represents an integer of from 0 to 4, or a substituent in which $R_f$ represents —$CF_3$, m represents 1, $R_g$ represents a hydrogen atom and n represents 4. More preferably, the substituent represented by Formula (2) is a substituent in which $R_f$ represents a fluorine atom, m represents an integer of from 2 to 4, $R_g$ represents a hydrogen atom and n represents an integer of from 1 to 3, or a substituent in which $R_f$ represents —$CF_3$, m represents 1, $R_g$ represents a hydrogen atom and n represents 4. Particularly preferably, the substituent represented by Formula (2) is a substituent in which $R_f$ represents a fluorine atom, m represents 2, $R_g$ represents a hydrogen atom and n represents 3, or a substituent in which $R_f$ represents —$CF_3$, m represents 1, $R_g$ represents a hydrogen atom and n represents 4.

Preferable examples of the compound represented by Formula (1) include the fluorine-containing dipyrromethene compound represented by the following Formula (6) or Formula (7) and tautomers thereof.

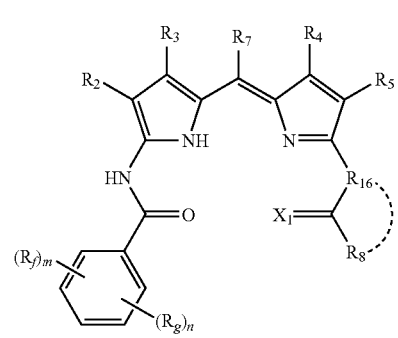

Formula (6)

In Formula (6), each $R_f$ independently represents a fluorine atom, a fluorine-containing alkyl group having 1 to 4 carbon atoms, a fluorine-containing aryl group, a fluorine-containing alkoxy group having 1 to 4 carbon atoms, a fluorine-containing alkylsulfonamido group having 1 to 4 carbon atoms, or a fluorine-containing arylsulfonamido group; m represents an integer of from 1 to 5; each $R_g$ independently represents a hydrogen atom or a substituent; n represents an integer of from 0 to 4; $R_2$, $R_3$, $R_4$, $R_5$, and $R_7$ each independently represent a hydrogen atom or a substituent; $X_1$ represents NY (where, Y represents a hydrogen atom, an alkyl group, an alkenyl group, an aryl group, a heterocyclic group, an acyl group, an alkylsulfonyl group, or an arylsulfonyl group), an oxygen atom, a nitrogen atom, or a sulfur atom; $R_{16}$ represents NR (where, R represents a hydrogen atom, an alkyl group, an alkenyl group, an aryl group, a heterocyclic group, an acyl group, an alkylsulfonyl group, or an arylsulfonyl group) or a carbon atom; and $R_8$ represents a hydrogen atom, an alkyl group, an alkenyl group, an aryl group, a heterocyclic group, an alkoxy group, an aryloxy group, an alkylamino group, an arylamino group, or a heterocyclic amino group. $R_{16}$ and $R_8$ may be linked to each other to form a 5-, 6-, or 7-membered ring.

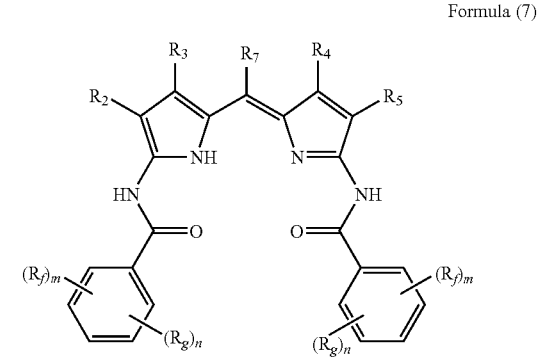

Formula (7)

In Formula (7), each $R_f$ independently represents a fluorine atom, a fluorine-containing alkyl group having 1 to 4 carbon atoms, a fluorine-containing aryl group, a fluorine-containing alkoxy group having 1 to 4 carbon atoms, a fluorine-containing alkylsulfonamido group having 1 to 4 carbon atoms, or a fluorine-containing arylsulfonamido group; m represents an integer of from 1 to 5; each $R_g$ independently represents a hydrogen atom or a substituent; n represents an integer of from 0 to 4; and $R_2$, $R_3$, $R_4$, $R_5$, and $R_7$ each independently represent a hydrogen atom or a substituent.

In Formula (6) and Formula (7), $R_2$ to $R_5$ and $R_7$ have the same definitions as those of $R_2$ to $R_5$ and $R_7$ in Formula (1), respectively, and preferable examples thereof are also the same as those of $R_2$ to $R_5$ and $R_7$ in Formula (1), respectively. $R_f$, $R_g$, m, and n in Formula (6) and Formula (7) have the same definitions as those of $R_f$, $R_g$, m, and n in Formula (2), respectively, and preferable examples thereof are also the same as those of $R_f$, $R_g$, m, and n in Formula (2), respectively.

In Formula (6), $R_8$ represents:

an alkyl group (preferably a linear, branched or cyclic alkyl group having 1 to 36 carbon atoms, more preferably 1 to 12 carbon atoms) such as a methyl group, an ethyl group, a propyl group, an isopropyl group, a butyl group, an isobutyl group, a t-butyl group, a hexyl group, a 2-ethylhexyl group, a dodecyl group, a cyclopropyl group, a cyclopentyl group, a cyclohexyl group or a 1-adamantyl group;

an alkenyl group (preferably an alkenyl group having 2 to 24 carbon atoms, more preferably 2 to 12 carbon atoms) such as a vinyl group, an allyl group or a 3-buten-1-yl group;

an aryl group (preferably an aryl group having 6 to 36 carbon atoms, more preferably 6 to 18 carbon atoms) such as a phenyl group or a naphthyl group;

a heterocyclic group (preferably a heterocyclic group having 1 to 24 carbon atoms, more preferably 1 to 12 carbon atoms) such as a 2-thienyl group, a 4-pyridyl group, a 2-furyl group, a 2-pyrimidinyl group, a 1-pyridyl group, a 2-benzothiazolyl group, a 1-imidazolyl group, a 1-pyrazolyl group or a benzotriazole-1-yl group;

an alkoxy group (preferably an alkoxy group having 1 to 36 carbon atoms, more preferably 1 to 18 carbon atoms) such as a methoxy group, an ethoxy group, a propyloxy group, a butoxy group, a hexyloxy group, a 2-ethylhexyloxy group, a dodecyloxy group or a cyclohexyloxy group;

an aryloxy group (preferably an aryloxy group having 6 to 24 carbon atoms, more preferably 1 to 18 carbon atoms) such as a phenoxy group or a naphthyloxy group;

an alkylamino group (preferably an alkylamino group having 1 to 36 carbon atoms, more preferably 1 to 18 carbon atoms) such as a methylamino group, an ethylamino group, a propylamino group, a butylamino group, a hexylamino group, a 2-ethylhexylamino group, an isopropylamino group, a t-butylamino group, a t-octylamino group, a cyclohexylamino group, an N,N-diethylamino group, an N,N-dipropylamino group, an N,N-dibutylamino group or an N-methyl-N-ethylamino group, an arylamino group (preferably an arylamino group having 6 to 36 carbon atoms, more preferably 6 to 18 carbon atoms) such as a phenylamino group, a naphthylamino group, an N,N-diphenylamino group or an N-ethyl-N-phenylamino group; or a heterocyclic amino group (preferably a heterocyclic amino group having 1 to 24 carbon atoms, more preferably 1 to 12 carbon atoms) such as a 2-aminopyrrole group, a 3-aminopyrazole group, a 2-aminopyridine group or a 3-aminopyridine group.

In Formula (6), when the alkyl, alkenyl, aryl, heterocyclic, alkoxy, aryloxy, alkylamino, arylamino, or heterocyclic amino group represented by $R_8$ is a group that can be substituted, $R_8$ may be substituted with a substituent, in which the substituent may be selected from the range of substituents represented by $R_1$ to $R_7$ described above. When $R_8$ is substituted with two or more substituents, the two or more substituents may be the same as or mutually different from one another.

In Formula (6), $X_1$ represents NY, an oxygen atom, a nitrogen atom or a sulfur atom.

Y represents a hydrogen atom;

an alkyl group (preferably a linear, branched or cyclic alkyl group having 1 to 36 carbon atoms, more preferably 1 to 12 carbon atoms) such as a methyl group, an ethyl group, a propyl group, an isopropyl group, a butyl group, an isobutyl group, a t-butyl group, a hexyl group, a 2-ethylhexyl group, a dodecyl group, a cyclopropyl group, a cyclopentyl group, a cyclohexyl group or a 1-adamantyl group;

an alkenyl group (preferably an alkenyl group having 2 to 24 carbon atoms, more preferably 2 to 12 carbon atoms) such as a vinyl group, an allyl group or a 3-buten-1-yl group;

an aryl group (preferably an aryl group having 6 to 36 carbon atoms, more preferably 6 to 18 carbon atoms) such as a phenyl group or a naphthyl group;

a heterocyclic group (preferably a heterocyclic group having 1 to 24 carbon atoms, more preferably 1 to 12 carbon atoms) such as a 2-thienyl group, a 4-pyridyl group, a 2-furyl group, a 2-pyrimidinyl group, a 1-pyridyl group, a 2-benzothiazolyl group, a 1-imidazolyl group, a 1-pyrazolyl group or a benzotriazole-1-yl group;

an acyl group (preferably an acyl group having 1 to 24 carbon atoms, more preferably 2 to 18 carbon atoms) such as an acetyl group, a pivaloyl group, a 2-ethylhexyl group, a benzoyl group or a cyclohexanoyl group;

an alkylsulfonyl group (preferably an alkylsulfonyl group having 1 to 24 carbon atoms, more preferably 1 to 18 carbon atoms) such as a methylsulfonyl group, an ethylsulfonyl group, an isopropylsulfonyl group or a cyclohexylsulfonyl group; or an arylsulfonyl group (preferably an arylsulfonyl group having 6 to 24 carbon atoms, more preferably 6 to 18 carbon atoms) such as a phenylsulfonyl group or a naphthylsulfonyl group.

In Formula (6), the alkyl, alkenyl, aryl, heterocyclic, acyl, alkylsulfonyl, or arylsulfonyl group represented by Y may be substituted with a substituent, in which the substituent may be selected from the range of substituents represented by $R_1$ to $R_7$ described above. When Y is substituted with two or more substituents, the two or more substituents may be the same as or mutually different from one another.

In Formula (6), $R_{16}$ represents NR or a carbon atom (where, R has the same definition as that of Y in $X_1$).

In Formula (6), $R_{16}$ and $R_8$ may be linked to each other to form a 5-, 6- or 7-membered ring. One bond of the ring formed by $R_{16}$, $R_8$ and carbon atoms may be replaced with a double bond. Examples of the ring formed by linking of $R_{16}$ with $R_8$ include 5-membered rings such as cyclopentane, pyrrolidine, tetrahydrofuran, dioxolane, tetrahydrothiophene, pyrrole, furan, thiophene, indole, benzofuran and benzothiophene; 6-membered rings such as cyclohexane, piperidine, piperazine, morpholine, tetrahydropyran, dioxane, pentamethylenesulfide, dithiane, benzene, piperidine, piperazine, pyridazine, quinoline and quinazoline; and 7-membered rings such as cycloheptane and hexamethyleneimine.

In Formula (6), when the 5-, 6- or 7-membered ring formed by linking of $R_{16}$ with $R_8$ is a ring that can be substituted, the ring may be substituted with a substituent, in which the substituent may be selected from the range of substituents represented by $R_1$ to $R_7$ described above. When the ring is substituted with two or more substituents, the two or more substituents may be the same as or mutually different from one another.

Preferable examples of the specific compound-1 represented by Formula (1) and the substituent represented by Formula (2) will be described.

In Formulae (1) and (2), it is preferable that a represents an integer of 1 or more, that each $R_f$ independently represents a fluorine atom, a fluorine-containing alkyl group having 1 to 4 carbon atoms, a fluorine-containing aryl group, a fluorine-containing alkylsulfonamido group having 1 to 4 carbon atoms, or a fluorine-containing arylsulfonamido group, that m represents an integer of from 1 to 5, that each $R_g$ independently represents a hydrogen atom or a substituent, that n represents an integer of from 0 to 4, that L represents a single bond, an oxygen atom, —NH—, —R—NH— (where, R represents an alkylene group), —Ar—NH— (where, Ar represents an arylene group), a carbonyl group, an ester group, an oxycarbonyl group, a thioester group, a thiocarbonyl group, *—CONH—, *—NHCO—, *—NHSO$_2$—, a sulfinyl group, a sulfonyl group, *—SO$_2$NH—, a substituted or unsubstituted alkylene chain having 1 to 4 carbon atoms, or a substituted or unsubstituted arylene group (where, * represents a bond linking to Formula (1)), that $R_1$ and $R_6$ each independently represent a hydrogen atom, an alkyl group, an alkenyl group, an aryl group, a heterocyclic group, a silyl group, a hydroxy group, a cyano group, an alkoxy group, an aryloxy group, a heterocyclic oxy group, an acyl group, an alkoxycarbonyl group, a carbamoyl group, an amino group, an anilino group, a heterocyclic amino group, a carbonamido group, an ureido group, an imido group, an alkoxycarbonylamino group, an aryloxycarbonylamino group, a sulfonamido group, an azo group, an alkylthio group, an arylthio group, a heterocyclic thio group, an alkylsulfonyl group, an arylsulfonyl group or a phosphinoylamino group, that $R_2$ and $R_5$ each independently represent a hydrogen atom, a halogen atom, an alkyl group, an alkenyl group, an aryl group, a heterocyclic group, a hydroxy group, a cyano group, a nitro group, an alkoxy group, an aryloxy group, a heterocyclic oxy group, an acyl group, an alkoxycarbonyl group, an aryloxycarbonyl group, a carbamoyl group, an imido group, an alkoxycarbonylamino group, a sulfonamido group, an azo group, an alkylthio group, an aryl thio group, a heterocyclic thio group, an alkylsulfonyl group, an arylsulfonyl group, or a sulfamoyl group, that $R_3$ and $R_4$ each independently represent a hydrogen atom, a halogen atom, an alkyl group, an alkenyl group, an aryl group, a heterocyclic group, a silyl group, a hydroxy group, a cyano group, an alkoxy group, an aryloxy group, a heterocyclic oxy group, an acyl group, an alkoxycarbonyl group, a carbamoyl group, an anilino group, a carbonamido group, an ureido group, an imido group, an alkoxycarbonylamino group, a sulfonamido group, an azo group, an alkylthio group, an arylthio group, a heterocyclic thio group, an alkylsulfonyl group, an arylsulfonyl group, a sulfamoyl group or a phosphinoylamino group, and that $R_7$ represents a hydrogen atom, a halogen atom, an alkyl group, an aryl group, or a heterocyclic group.

In Formulae (1) and (2), it is more preferable that a represents an integer of 1 or more, that each $R_f$ independently represents a fluorine atom, a fluorine-containing alkyl group having 1 to 4 carbon atoms, a fluorine-containing aryl group, a fluorine-containing alkylsulfonamido group having 1 to 4 carbon atoms or a fluorine-containing arylsulfonamido group, that m represents an integer of from 1 to 5, that each $R_g$ independently represents a hydrogen atom or a substituent, that n represents an integer of from 0 to 4, that L represents a single bond, —NH—, —R—NH— (where, R represents an alkylene group), —Ar—NH— (where, Ar represents an arylene group), a carbonyl group, an ester group, an oxycarbonyl group, a thioester group, a thiocarbonyl group, *—CONH—, *—NHCO—, *—NHSO$_2$—, a sulfinyl group, a sulfonyl group, *—SO$_2$NH—, a substituted or unsubstituted alkylene chain having 1 to 4 carbon atoms, or a substituted or unsubstituted arylene group (where, * represents a bond linking to Formula (1)), that $R_1$ and $R_6$ each independently represent a hydrogen atom, an alkyl group, an alkenyl group, an aryl group, a heterocyclic group, a cyano group, an acyl group, an alkoxycarbonyl group, a carbamoyl group, an amino group, a heterocyclic amino group, a carbonamido group, an ureido group, an imido group, an alkoxycarbonylamino group, a sulfonamido group, an azo group, an alkylsulfonyl group, an arylsulfonyl group or a phosphinoylamino group, that $R_2$ and $R_5$ each independently represent an alkyl group, an alkenyl group, an aryl group, a heterocyclic group, a cyano group, a nitro group, an acyl group, an alkoxycarbonyl group, an aryloxycarbonyl group, a carbamoyl group, an imido group, an alkylsulfonyl group, an arylsulfonyl group or a sulfamoyl group, that $R_3$ and $R_4$ each independently represent a hydrogen atom, an alkyl group, an alkenyl group, an aryl group, a heterocyclic group, a cyano group, an acyl group, an alkoxycarbonyl group, a carbamoyl group, a carbonamido group, an ureido group, an imido group, an alkoxycarbonylamino group, a sulfonamido group, an alkylthio group, an arylthio group, a heterocyclic thio group, an alkylsulfonyl group, an arylsulfonyl group or a sulfamoyl group, and that $R_7$ represents a hydrogen atom, a halogen atom, an alkyl group, an aryl group, or a heterocyclic group.

In Formulae (1) and (2), it is still more preferable that a represents an integer of 1 or more, that each $R_f$ independently represents a fluorine atom, a fluorine-containing alkyl group having 1 to 4 carbon atoms, a fluorine-containing aryl group, a fluorine-containing alkylsulfonamido group or a fluorine-containing arylsulfonamido group having 1 to 4 carbon atoms, m represents an integer of from 1 to 5, that each $R_g$ independently represents a hydrogen atom or a substituent, that n represents an integer of from 0 to 4, that L represents a single bond, —NH—, —R—NH— (where, R represents an alkylene group), —Ar—NH— (where, Ar represents an arylene group), a carbonyl group, an ester group, an oxycarbonyl group, a thioester group, a thiocarbonyl group, *—CONH—, *—NHCO—, *—NHSO$_2$—, a sulfinyl group, a sulfonyl group, *—SO$_2$NH—, a substituted or unsubstituted alkylene chain having 1 to 4 carbon atoms, or a substituted or unsubstituted arylene group (where, * represents a bond linking to Formula (1)), that $R_1$ and $R_6$ each independently represent a hydrogen atom, an alkyl group, an aryl group, a heterocyclic group, an amino group, a heterocyclic amino group, a carbonamido group, an ureido group, an imido group, an alkoxycarbonylamino group, a sulfonamido group, an azo group, an alkylsulfonyl group, an arylsulfonyl group or a phosphinoylamino group, that $R_2$ and $R_5$ each independently represent an alkyl group, an aryl group, a heterocyclic group, a cyano group, an acyl group, an alkoxycarbonyl group, a carbamoyl group, an alkylsulfonyl group, or an arylsulfonyl group, that $R_3$ and $R_4$ each independently represent a hydrogen atom, an alkyl group, an aryl group, or a heterocyclic group, and that $R_7$ represents a hydrogen atom, an alkyl group, an aryl group, or a heterocyclic group.

Metal or Metal Compound

In order to form the specific metal complex compound-1 for the colored curable composition of the invention, the metal or metal compound is used together with the specific compound-1 (the fluorine-containing dipyrromethene compound represented by Formula (1)).

The metal or metal compound that forms the specific metal complex compound-1 together with the specific compound-1 is not particularly limited, as long as the metal or metal compound can form a complex with the specific compound-1, and examples thereof include bivalent metal atoms, bivalent metal oxides, bivalent metal hydroxides and bivalent metal chlorides. Specific examples thereof include metals such as Zn, Mg, Si, Sn, Rh, Pt, Pd, Mo, Mn, Pb, Cu, Ni, Co, and Fe; metal chlorides such as AlCl, InCl, FeCl, TiCl$_2$, SnCl$_2$, SiCl$_2$ and GeCl$_2$; metal oxides such as TiO and VO; and metal hydroxides such as Si(OH)$_2$.

Among these, in consideration of the stability, spectroscopic properties, heat resistance, light-fastness, and production suitability of complexes, Fe, Zn, Mg, Si, Pt, Pd, Mo, Mn, Cu, Ni, Co, TiO and VO are preferable; Zn, Mg, Si, Pt, Pd, Cu, Ni, Co and VO are more preferable; and Zn is most preferable.

Hereinafter, preferable ranges of the specific metal complex compound-1 formed with the compound represented by Formula (1) (including the substituent of Formula (2)) and the metal or metal compound will be described.

A preferable range (hereinafter, referred to as "preferable range A") is as follows:

in Formula (1), $R_1$ and $R_6$ each independently represent a hydrogen atom, an alkyl group, an alkenyl group, an aryl group, a heterocyclic group, a silyl group, a hydroxyl group, a cyano group, an alkoxy group, an aryloxy group, a heterocyclic oxy group, an acyl group, an alkoxycarbonyl group, a carbamoyl group, an amino group, an anilino group, a heterocyclic amino group, a carbonamido group, a ureido group, an imido group, an alkoxycarbonylamino group, an aryloxycarbonylamino group, a sulfonamido group, an azo group, an alkylthio group, an arylthio group, a heterocyclic thio group, an alkylsulfonyl group, an arylsulfonyl group or a phosphinoylamino group; $R_2$ and $R_5$ each independently represent a hydrogen atom, a halogen atom, an alkyl group, an alkenyl group, an aryl group, a heterocyclic group, a hydroxyl group, a cyano group, a nitro group, an alkoxy group, an aryloxy group, a heterocyclic oxy group, an acyl group, an alkoxycarbonyl group, an aryloxycarbonyl group, a carbamoyl group, an imido group, an alkoxycarbonylamino group, a sulfonamido group, an azo group, an alkylthio group, an arylthio group, a heterocyclic thio group, an alkylsulfonyl group, an arylsulfonyl group or a sulfamoyl group; $R_3$ and $R_4$ each independently represent a hydrogen atom, a halogen atom, an alkyl group, an alkenyl group, an aryl group, a heterocyclic group, a silyl group, a hydroxyl group, a cyano group, an alkoxy group, an aryloxy group, a heterocyclic oxy group, an acyl group, an alkoxycarbonyl group, a carbamoyl group, an anilino group, a carbonamido group, a ureido group, an imido group, an alkoxycarbonylamino group, a sulfonamido group, an azo group, an alkylthio group, an arylthio group, a heterocyclic thio group, an alkylsulfonyl group, an arylsulfonyl group, a sulfamoyl group or a phosphinoylamino group; $R_7$ represents a hydrogen atom, a halogen atom, an alkyl group, an aryl group or a heterocyclic group;

the metal or metal compound represents Zn, Mg, Si, Pt, Pd, Mo, Mn, Cu, Ni, Co, TiO, or VO; and in Formula (2), each $R_f$ independently represents a fluorine atom, a fluorine-containing alkyl group having 1 to 4 carbon atoms, a fluorine-containing aryl group, a fluorine-containing alkoxy group having 1 to 4 carbon atoms, or a fluorine-containing alkylsulfonamido group having 1 to 4 carbon atoms; m represents an integer of from 1 to 5; each $R_g$ independently represents a hydrogen atom; n represents an integer of from 0 to 4; L represents a single bond, an oxygen atom, a sulfur atom, —NH—, —R—NH— (where, R represents an alkylene group), —Ar—NH— (where, Ar represents an arylene group), a carbonyl group, an ester group, an oxycarbonyl group, a thioester group, a thiocarbonyl group, *—CONH—, *—NHCO—, *—NHSO$_2$—, a sulfinyl group, a sulfonyl group, *—SO$_2$NH—, a substituted or unsubstituted alkylene chain having 1 to 4 carbon atoms, or a substituted or unsubstituted arylene group (where, * represents a bond linking to Formula (1)); and a represents an integer of 1 or more.

A more preferable range (hereinafter, referred to as "preferable range B") is as follows:

in Formula (1), $R_1$ and $R_6$ each independently represent a hydrogen atom, an alkyl group, an alkenyl group, an aryl group, a heterocyclic group, an alkoxy group, an aryloxy group, a heterocyclic oxy group, an acyl group, an alkoxycarbonyl group, a carbamoyl group, an amino group, an anilino group, a heterocyclic amino group, a carbonamido group, a ureido group, an imido group, an alkoxycarbonylamino group, an aryloxycarbonylamino group, a sulfonamido group, an azo group, an alkylthio group, an arylthio group, a heterocyclic thio group, an alkylsulfonyl group, an arylsulfonyl group or a phosphinoylamino group; $R_2$ and $R_5$ each independently represent an alkyl group, an alkenyl group, an aryl group, a heterocyclic group, a hydroxyl group, a cyano group, a nitro group, an alkoxy group, an aryloxy group, a heterocyclic oxy group, an acyl group, an alkoxycarbonyl group, an aryloxycarbonyl group, a carbamoyl group, an imido group, an alkoxycarbonylamino group, a sulfonamido group, an azo group, an alkylthio group, an arylthio group, a heterocyclic thio group, an alkylsulfonyl group, an arylsulfonyl group or a sulfamoyl group; $R_3$ and $R_4$ each independently represent a hydrogen atom, an alkyl group, an alkenyl group, an aryl group, a heterocyclic group, a silyl group, a hydroxyl group, a cyano group, an alkoxy group, an aryloxy group, a heterocyclic oxy group, an acyl group, an alkoxycarbonyl group, a carbamoyl group, an anilino group, a carbonamido group, a ureido group, an imido group, an alkoxycarbonylamino group, a sulfonamido group, an azo group, an alkylthio group, an arylthio group, a heterocyclic thio group, an alkylsulfonyl group, an arylsulfonyl group or a sulfamoyl group; $R_7$ represents a hydrogen atom, a halogen atom, an alkyl group, an aryl group or a heterocyclic group;

the metal or metal compound represents Zn, Mg, Si, Pt, Pd, Mo, Mn, Cu, Ni, Co, TiO, or VO; and in Formula (2), each $R_f$ independently represents a fluorine atom, a fluorine-containing alkyl group having 1 to 4 carbon atoms, a fluorine-containing aryl group, a fluorine-containing alkoxy group having 1 to 4 carbon atoms, or a fluorine-containing alkylsulfonamido group having 1 to 4 carbon atoms; m represents an integer of from 1 to 5; each $R_g$ independently represents a hydrogen atom; n represents an integer of from 0 to 4; L represents a single bond, an oxygen atom, a sulfur atom, —NH—, —R—NH— (where, R represents an alkylene group), —Ar—NH— (where, Ar represents an arylene group), a carbonyl group, an ester group, an oxycarbonyl group, a thioester group, a thiocarbonyl group, *—CONH—, *—NHCO—, *—NHSO$_2$—, a sulfinyl group, a sulfonyl group, *—SO$_2$NH—, a substituted or unsubstituted alkylene chain having 1 to 4 carbon atoms, or a substituted or unsubstituted arylene group (where, * represents a bond linking to Formula (1)); and a represents an integer of 1 or more.

A still more preferable range (hereinafter, referred to as "preferable range C") is as follows:

in Formula (1), $R_1$ and $R_6$ each independently represent a hydrogen atom, an alkyl group, an aryl group, a heterocyclic group, an amino group, an anilino group, a heterocyclic amino group, a carbonamido group, a ureido group, an imido group, an alkoxycarbonylamino group, an aryloxycarbonylamino group, a sulfonamido group, an azo group, an alkylthio group, an arylthio group, a heterocyclic thio group, an alkylsulfonyl group, an arylsulfonyl group or a phosphinoylamino group; $R_2$ and $R_5$ each independently represent an alkyl group, an aryl group, a heterocyclic group, a cyano group, an acyl group, an alkoxycarbonyl group, a carbamoyl group, an alkylsulfonyl group or an arylsulfonyl group; $R_3$ and $R_4$ each independently represent a hydrogen atom, an alkyl group, an alkenyl group, an aryl group or a heterocyclic group; $R_7$ represents a hydrogen atom, an alkyl group, an aryl group or a heterocyclic group;

the metal or metal compound represents Zn, Cu, Co or VO; and in Formula (2), each $R_f$ independently represents a fluorine atom, a fluorine-containing alkyl group having 1 to 4 carbon atoms, a fluorine-containing aryl group, a fluorine-containing alkoxy group having 1 to 4 carbon atoms, or a fluorine-containing alkylsulfonamido group having 1 to 4 carbon atoms; m represents an integer of from 1 to 5; each $R_g$ independently represents a hydrogen atom; n represents an integer of from 0 to 4; L represents a single bond, an oxygen atom, a sulfur atom, —NH—, —R—NH— (where, R represents an alkylene group), —Ar—NH— (where, Ar represents an arylene group), a sulfinyl group, a sulfonyl group, a substituted or unsubstituted alkylene chain having 1 to 4 carbon atoms, or a substituted or unsubstituted arylene group (where, * represents a bond linking to Formula (1)); and a represents an integer of 1 or more.

When the above-descried saturated or unsaturated 5-, 6-, or 7-membered ring, which is formed by mutual bonding of $R_1$ and $R_2$, $R_2$ and $R_3$, $R_4$ and $R_5$, or $R_5$ and $R_6$ in Formula (1) (mutual binding in each pair is independent from whether mutual bonding occurs in the other pairs) is unsubstituted, examples of such a ring include pyrrole, furan, thiophene, pyrazole, imidazole, triazole, oxazole, thiazole, pyrrolidine, piperidine, cyclopentene, cyclohexene, benzene, pyridine, pyrazine, and pyridazine rings. Among these, benzene and pyridine rings are preferable.

When the above-descried saturated or unsaturated 5-, 6-, or 7-membered ring, which is formed by mutual bonding of $R_1$ and $R_2$, $R_2$ and $R_3$, $R_4$ and $R_5$, or $R_5$ and $R_6$ in Formula (1) (mutual binding in each pair is independent from whether mutual bonding occurs in the other pairs) has a substituent, the substituent may be selected from the range of substituents represented by $R_1$ to $R_7$ described above. Preferable examples of the substituent are also the same as those of the substituent represented by $R_1$ to $R_7$.

The specific metal complex compound-1 formed with the compound represented by Formula (1) and the metal or metal compound may be in the form of any tautomer.

Fluorine-Containing Dipyrromethene Metal Complex Compound Represented by Formula (3)

Preferable examples of the specific metal complex compound-1 include the fluorine-containing dipyrromethene metal complex compound represented by the following Formula (3) (hereinafter, sometimes referred to as a "specific metal complex compound-2").

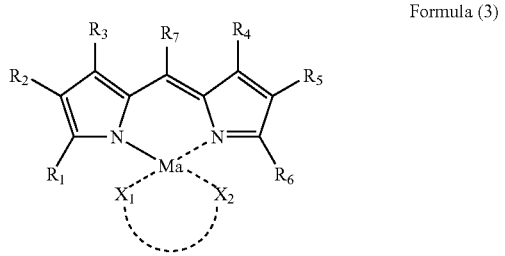

Formula (3)

In Formula (3), $R_1$, $R_2$, $R_3$, $R_4$, $R_5$, $R_6$, and $R_7$ each independently represent a hydrogen atom or a substituent; Ma represents a metal or metal compound; $X_1$ represents a group that can bind to Ma; and $X_2$ represents a group required for neutralizing the electric charge of Ma. Here, $X_1$ and $X_2$ may be linked to each other to form a 5-, 6-, or 7-membered ring.

In Formula (3), at least one hydrogen atom in at least one of $R_1$ to $R_7$ is replaced by a substituent represented by Formula (2). In Formula (2), a represents an integer of 1 or more; each $R_f$ independently represents a fluorine atom, a fluorine-containing alkyl group having 1 to 4 carbon atoms, a fluorine-containing aryl group, a fluorine-containing alkoxy group having 1 to 4 carbon atoms, a fluorine-containing alkylsulfonamido group having 1 to 4 carbon atoms, or a fluorine-containing arylsulfonamido group; m represents an integer of from 1 to 5; each $R_g$ independently represents a hydrogen atom or a substituent; n represents an integer of from 0 to 4; and L represents a single bond, an oxygen atom, a sulfur atom, —NH—, —R—NH— (where, R represents an alkylene group), —Ar—NH— (where, Ar represents an arylene group), a carbonyl group, an ester group, an oxycarbonyl group, a thioester group, a thiocarbonyl group, *—CONH—, *—NHCO—, *—NHSO$_2$—, a sulfinyl group, a sulfonyl group, *—SO$_2$NH—, an alkylene chain having 1 to 4 carbon atoms, or an arylene group (where, * represents a bond linking to Formula (3)).

$R_1$ to $R_7$ in Formula (3) have the same definitions as those of $R_1$ to $R_7$ of the fluorine-containing dipyrromethene compound (the specific compound-1) represented by Formula (1), respectively. Preferable examples thereof are also the same as those of $R_1$ to $R_7$ in the specific compound-1, respectively. Ma in Formula (3) represents a metal or metal compound, and has the same definition as those of a metal or metal compound of the specific compound-1. Preferable examples thereof are also the same as those of a metal or metal compound of the specific metal complex compound-1.

$X_1$ in Formula (3) may be any atom that can bind to the metal atom Ma, and examples thereof include water, alcohols (such as methanol, ethanol, and propanol), and the compounds described, for example, in Takeichi Sakaguchi and Keihei Ueno, "Metal Chelates" vol. 1, (1995), vol. 2 (1996), and vol. 3 (1997) (all published by Nankodo).

$X_2$ in Formula (3) represents a group required for neutralizing the electric charge of Ma, such as a halogen atom, a hydroxyl group, a carboxylic acid group, a phosphate group, or a sulfonic group.

$X_1$ and $X_2$ in Formula (3) may be linked to each other to form a 5-, 6-, or 7-membered ring together with Ma. The ring formed may be saturated or unsaturated. The 5-, 6-, or 7-membered may be a ring containing only carbon atoms, or may be a heterocyclic ring having at least one atom selected from a nitrogen atom, an oxygen atom and/or a sulfur atom.

Fluorine-Containing Dipyrromethene Metal Complex Compound Represented by Formula (4) or Formula (5)

Preferable examples of the specific metal complex compound-1 include the fluorine-containing dipyrromethene metal complex compound represented by the following Formula (4) (hereinafter, sometimes referred to as a "specific metal complex compound-3") and the fluorine-containing dipyrromethene metal complex compound represented by the following Formula (5) (hereinafter, sometimes referred to as a "specific metal complex compound-4").

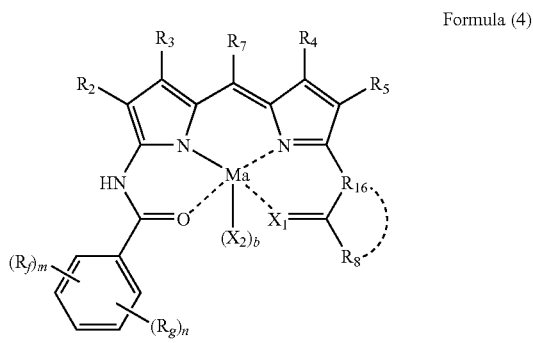

Formula (4)

In Formula (4), $R_2$, $R_3$, $R_4$, $R_5$, and $R_7$ each independently represent a hydrogen atom or a substituent. Each $R_f$ independently represents a fluorine atom, a fluorine-containing alkyl group having 1 to 4 carbon atoms, a fluorine-containing aryl group, a fluorine-containing alkoxy group having 1 to 4 carbon atoms, a fluorine-containing alkylsulfonamido group having 1 to 4 carbon atoms, or a fluorine-containing arylsulfonamido group, and m represents an integer of from 1 to 5. Each $R_g$ independently represents a hydrogen atom or a substituent, and n represents an integer of from 0 to 4. Ma represents a metal or metal compound and $X_1$ represents NY (where, Y represents a hydrogen atom, an alkyl group, an alkenyl group, an aryl group, a heterocyclic group, an acyl group, an alkylsulfonyl group or an arylsulfonyl group), an oxygen atom, a nitrogen atom or a sulfur atom. $R_{16}$ represents NR (where, R represents a hydrogen atom, an alkyl group, an alkenyl group, an aryl group, a heterocyclic group, an acyl group, an alkylsulfonyl group or an arylsulfonyl group), a nitrogen group or a carbon atom; and $R_8$ represents a hydrogen atom, an alkyl group, an alkenyl group, an aryl group, a heterocyclic group, an alkoxy group, an aryloxy group, an alkylamino group, an arylamino group or a heterocyclic amino group. $R_{16}$ and $R_8$ may be linked to each other to form a 5-, 6-, or 7-membered ring. $X_2$ represents a group required for neutralizing the electric charge of Ma; and b represents 0, 1, or 2.

Formula (5)

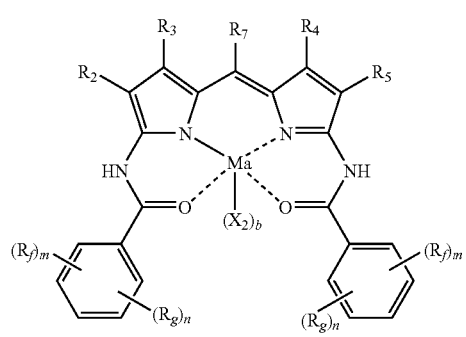

In Formula (5), $R_2$, $R_3$, $R_4$, $R_5$, and $R_7$ each independently represent a hydrogen atom or a substituent. Each $R_f$ independently represents a fluorine atom, a fluorine-containing alkyl group having 1 to 4 carbon atoms, a fluorine-containing aryl group, a fluorine-containing alkoxy group having 1 to 4 carbon atoms, a fluorine-containing alkylsulfonamido group having 1 to 4 carbon atoms, or a fluorine-containing arylsulfonamido group; m represents an integer of from 1 to 5. Each $R_g$ independently represents a hydrogen atom or a substituent; n represents an integer of from 0 to 4; Ma represents a metal or metal compound; $X_2$ represents a group required for neutralizing the electric charge of Ma; and b represents 0, 1, or 2.

$R_2$, $R_3$, $R_4$, $R_5$, and $R_7$ in Formulae (4) and (5) have the same definitions as those of $R_2$, $R_3$, $R_4$, $R_5$, and $R_7$ in Formula (1), respectively, and preferable examples thereof are the same as those of $R_2$, $R_3$, $R_4$, $R_5$, and $R_7$ in Formula (1), respectively. Ma in Formulae (4) and (5) represents a metal or metal compound, and preferable examples thereof are the same as those of the metal or metal compound in the above specific metal complex compound-1.

In Formula (4), $R_8$ represents:

an alkyl group (preferably a linear, branched or cyclic alkyl group having 1 to 36 carbon atoms, more preferably 1 to 12 carbon atoms) such as a methyl group, an ethyl group, a propyl group, an isopropyl group, a butyl group, an isobutyl group, a t-butyl group, a hexyl group, a 2-ethylhexyl group, a dodecyl group, a cyclopropyl group, a cyclopentyl group, a cyclohexyl group or a 1-adamantyl group;

an alkenyl group (preferably an alkenyl group having 2 to 24 carbon atoms, more preferably 2 to 12 carbon atoms) such as a vinyl group, an allyl group or a 3-buten-1-yl group;

an aryl group (preferably an aryl group having 6 to 36 carbon atoms, more preferably 6 to 18 carbon atoms) such as a phenyl group or a naphthyl group;

a heterocyclic group (preferably a heterocyclic group having 1 to 24 carbon atoms, more preferably 1 to 12 carbon atoms) such as a 2-thienyl group, a 4-pyridyl group, a 2-furyl group, a 2-pyrimidinyl group, a 1-pyridyl group, a 2-benzothiazolyl group, a 1-imidazolyl group, a 1-pyrazolyl group or a benzotriazole-1-yl group;

an alkoxy group (preferably an alkoxy group having 1 to 36 carbon atoms, more preferably 1 to 18 carbon atoms) such as a methoxy group, an ethoxy group, a propyloxy group, a butoxy group, a hexyloxy group, a 2-ethylhexyloxy group, a dodecyloxy group or a cyclohexyloxy group;

an aryloxy group (preferably an aryloxy group having 6 to 24 carbon atoms, more preferably 1 to 18 carbon atoms) such as a phenoxy group or a naphthyloxy group;

an alkylamino group (preferably an alkylamino group having 1 to 36 carbon atoms, more preferably 1 to 18 carbon atoms) such as a methylamino group, an ethylamino group, a propylamino group, a butylamino group, a hexylamino group, a 2-ethylhexylamino group, an isopropylamino group, a t-butylamino group, a t-octylamino group, a cyclohexylamino group, an N,N-diethylamino group, an N,N-dipropylamino group, an N,N-dibutylamino group or an N-methyl-N-ethylamino group, an arylamino group (preferably an arylamino group having 6 to 36 carbon atoms, more preferably 6 to 18 carbon atoms) such as a phenylamino group, a naphthylamino group, an N,N-diphenylamino group or an N-ethyl-N-phenylamino group; or a heterocyclic amino group (preferably a heterocyclic amino group having 1 to 24 carbon atoms, more preferably 1 to 12 carbon atoms) such as a 2-aminopyrrole group, a 3-aminopyrazole group, a 2-aminopyridine group or a 3-aminopyridine group.

The alkyl, alkenyl, aryl, heterocyclic, alkoxy, aryloxy, alkylamino, arylamino, or heterocyclic amino group represented by $R_8$ in Formula (4) is a group that can be substituted, $R_8$ may be substituted with a substituent, in which the substituent may be selected from the range of substituents represented by $R_1$ to $R_7$ described above. When $R_8$ has two or more substituents, the two or more substituents may be the same as or mutually different from one another.

In Formula (4), $X_1$ represents NY, an oxygen atom, a nitrogen atom or a sulfur atom.

Y represents a hydrogen atom;

an alkyl group (preferably a linear, branched or cyclic alkyl group having 1 to 36 carbon atoms, more preferably 1 to 12 carbon atoms) such as a methyl group, an ethyl group, a propyl group, an isopropyl group, a butyl group, an isobutyl group, a t-butyl group, a hexyl group, a 2-ethylhexyl group, a dodecyl group, a cyclopropyl group, a cyclopentyl group, a cyclohexyl group or a 1-adamantyl group;

an alkenyl group (preferably an alkenyl group having 2 to 24 carbon atoms, more preferably 2 to 12 carbon atoms) such as a vinyl group, an allyl group or a 3-buten-1-yl group;

an aryl group (preferably an aryl group having 6 to 36 carbon atoms, more preferably 6 to 18 carbon atoms) such as a phenyl group or a naphthyl group;

a heterocyclic group (preferably a heterocyclic group having 1 to 24 carbon atoms, more preferably 1 to 12 carbon atoms) such as a 2-thienyl group, a 4-pyridyl group, a 2-furyl group, a 2-pyrimidinyl group, a 1-pyridyl group, a 2-benzothiazolyl group, a 1-imidazolyl group, a 1-pyrazolyl group or a benzotriazole-1-yl group;

an acyl group (preferably an acyl group having 1 to 24 carbon atoms, more preferably 2 to 18 carbon atoms) such as an acetyl group, a pivaloyl group, a 2-ethylhexyl group, a benzoyl group or a cyclohexanoyl group;

an alkylsulfonyl group (preferably an alkylsulfonyl group having 1 to 24 carbon atoms, more preferably 1 to 18 carbon atoms) such as a methylsulfonyl group, an ethylsulfonyl group, an isopropylsulfonyl group or a cyclohexylsulfonyl group; or an arylsulfonyl group (preferably an arylsulfonyl group having 6 to 24 carbon atoms, more preferably 6 to 18 carbon atoms) such as a phenylsulfonyl group or a naphthylsulfonyl group.

In Formula (4), the alkyl, alkenyl, aryl, heterocyclic, acyl, alkylsulfonyl, or arylsulfonyl group represented by Y may have a further substituent, in which the further substituent may be selected from the range of substituents represented by $R_1$ to $R_7$ described above. When Y has two or more substituents, the two or more substituents may be the same as or mutually different from one another.

In Formula (4), $R_{16}$ represents NR or a carbon atom, and R has the same definition as that of Y in $X_1$.

In Formula (4), $R_{16}$ and $R_8$ may be linked to each other to form a 5-, 6- or 7-membered ring. One bond of the ring formed by $R_{16}$, $R_8$ and carbon atoms may be replaced with a double bond. Examples of the ring formed by linking of $R_{16}$ with $R_8$ include 5-membered rings such as cyclopentane, pyrrolidine, tetrahydrofuran, dioxolane, tetrahydrothiophene, pyrrole, furan, thiophene, indole, benzofuran and benzothiophene; 6-membered rings such as cyclohexane, piperidine, piperazine, morpholine, tetrahydropyran, dioxane, pentamethylenesulfide, dithiane, benzene, piperidine, piperazine, pyridazine, quinoline and quinazoline rings; and 7-membered rings such as cycloheptane and hexamethyleneimine rings.

In Formula (4), when the 5-, 6- or 7-membered ring formed by linking of $R_{16}$ with $R_8$ is a ring that can be substituted, the ring may be substituted with a substituent, in which the substituent may be selected from the range of substituents represented by $R_1$ to $R_7$ described above. When the ring is substituted with two or more substituents, the two or more substituents may be the same as or mutually different from one another.

In Formulae (4) and (5), $X_2$ represents a group required for neutralizing the electric charge of Ma, and examples thereof include the same groups as those of $X_2$ in Formula (3).

In Formulae (4) and (5), b represents 0, 1, or 2.

$R_f$, $R_g$, m, and n in Formula (4) and Formula (5) have the same definitions as those of $R_f$, $R_g$, m, and n in Formula (2), respectively, and preferable examples thereof are also the same as those of $R_f$, $R_g$, m, and n in Formula (2), respectively. Specifically, it is preferable that each $R_f$ independently represents a fluorine atom, a fluorine-containing alkyl group having 1 to 4 carbon atoms, or a fluorine-containing alkoxy group having 1 to 4 carbon atoms, that m represents an integer of from 1 to 2, that each $R_g$ independently represents a hydrogen atom, and that n represents an integer of from 0 to 4.

In the compound represented by Formula (4) or Formula (5), it is preferable that $R_2$ to $R_5$ and $R_7$ (and preferably Ma) each are within the "preferable range A or B" mentioned in the description of $R_2$ to $R_5$ and $R_7$ (and a metal or metal compound) of the metal complex compound-1 obtained using the compound represented by Formula (1) and a metal or metal compound, that $X_2$ represents a group that can link with Ma through an oxygen atom, that b represents 0 or 1, that each $R_f$ independently represents a fluorine atom, a fluorine-containing alkyl group having 1 to 4 carbon atoms, or a fluorine-containing alkoxy group having 1 to 4 carbon atoms, that m represents an integer of from 1 to 2, that each $R_g$ independently represents a hydrogen atom, and that n represents an integer of from 0 to 4. In addition thereto, in the case of Formula (4), it is preferable that $X_1$ represents NY (where, Y represents a hydrogen atom or an alkyl group), a nitrogen atom, or an oxygen atom, that $R_{16}$ represents NR (where, R represents a hydrogen atom or an alkyl group), a nitrogen atom, or a carbon atom, and that $R_8$ represents an alkyl group, an aryl group, a heterocyclic group, an alkoxy group, or an alkylamino group ($R_{16}$ and $R_8$ are preferably linked to each other to form a 5- or 6-membered ring).

In the compound represented by Formula (4) or Formula (5), it is more preferable that $R_2$ to $R_5$ and $R_7$ (and preferably Ma) each are within the "preferable range C" mentioned in the description of $R_2$ to $R_5$ and $R_7$ (and a metal or metal compound) of the compound represented by Formula (1), that $X_2$ represents a group that can link with Ma through an oxygen atom, that b represents 0 or 1, that each $R_f$ independently represents a fluorine atom, a fluorine-containing alkyl group having 1 to 4 carbon atoms, or a fluorine-containing alkoxy group having 1 to 4 carbon atoms, that m represents an integer of from 1 to 2, that each $R_g$ independently represents a hydrogen atom, and that n represents an integer of from 0 to 4. In addition thereto, in the case of Formula (4), it is more preferable that $X_1$ represents an oxygen atom, that $R_{16}$ represents NH, and that $R_8$ represents an alkyl group, an aryl group, a heterocyclic group, an alkoxy group, or an alkylamino group ($R_{16}$ and $R_8$ are preferably linked to each other to form a 5- or 6-membered ring).

In the compound represented by Formula (6) or Formula (7), it is preferable that $R_2$ to $R_5$ and $R_7$ each are within the "preferable range A or B" mentioned in the description of $R_2$ to $R_5$ and $R_7$ of the compound represented by Formula (1), that each $R_f$ independently represents a fluorine atom, a fluorine-containing alkyl group having 1 to 4 carbon atoms, or a fluorine-containing alkoxy group having 1 to 4 carbon atoms, that m represents an integer of from 1 to 2, that each $R_g$ independently represents a hydrogen atom, and that n represents an integer of from 0 to 4. In addition thereto, in the case of Formula (6), it is preferable that $X_1$ represents NY (where, Y represents a hydrogen atom or an alkyl group), a nitrogen atom, or an oxygen atom, that $R_{16}$ represents NR (where, R represents a hydrogen atom or an alkyl group), a nitrogen atom, or a carbon atom, and that $R_8$ represents an alkyl group, an aryl group, a heterocyclic group, an alkoxy group, or an alkylamino group ($R_{16}$ and $R_8$ are preferably linked to each other to form a 5- or 6-membered ring).

In the compound represented by Formula (6) or Formula (7), it is more preferable that $R_2$ to $R_5$ and $R_7$ each are within the "preferable range C" mentioned in the description of $R_2$ to $R_5$ and $R_7$ of the compound represented by Formula (1), that each $R_f$ independently represents a fluorine atom, a fluorine-containing alkyl group having 1 to 4 carbon atoms, or a fluorine-containing alkoxy group having 1 to 4 carbon atoms, that m represents an integer of from 1 to 2, that each $R_g$ independently represents a hydrogen atom, and that n represents an integer of from 0 to 4. In addition thereto, in the case of Formula (6), it is more preferable that $X_1$ represents an oxygen atom, that $R_{16}$ represents NH, and that $R_8$ represents an alkyl group, an aryl group, a heterocyclic group, an alkoxy group, or an alkylamino group ($R_{16}$ and $R_8$ are preferably linked to each other to form a 5- or 6-membered ring).

In consideration of film thickness, the molar absorption coefficient of the specific metal complex compounds-1, -2, -3 and -4 of the invention is preferably as high as possible, and 60,000 or higher is preferable. The maximum absorption wavelength (λmax) thereof is preferably from 520 nm to 580 nm, and more preferably from 530 nm to 570 nm, in order to improve color purity. The maximum absorption wavelength and the molar absorption coefficient are determined by using a spectrophotometer UV-2400PC (manufactured by Shimadzu Corporation).

The melting point of the specific metal complex compound-1 of the invention is preferably not too high, in consideration of solubility.

Specific examples of the specific metal complex compound-1 of the invention (including the specific metal complex compounds-2, -3 and -4) and specific examples of the compound represented by Formula (6) or Formula (7) (exemplary compounds Ia-1 to Ia-80, Ib-1 to Ib-80, IIa-1 to IIa-40, and IIb-1 to IIb-40) are shown below. However, the present invention is not limited to these examples.

Here, in specific examples of the specific metal complex compound-1, Ma represents a metal or metal compound, preferably Zn.

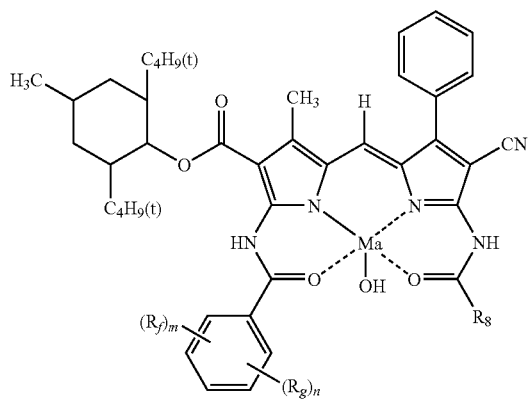

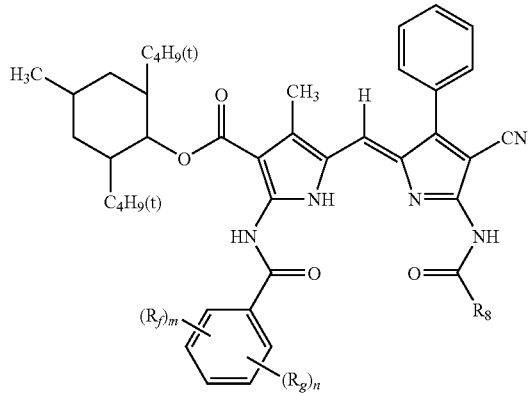

| | | | | | |
|---|---|---|---|---|---|
| Ia-6 | " | " | " | " | 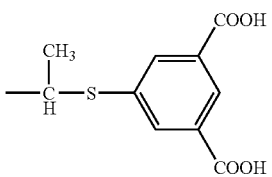 [SMILES: CC(C)Sc1cc(C(=O)O)cc(C(=O)O)c1] |
| Ia-7 | -4-F | " | " | " | —CH₃ |
| Ia-8 | " | " | " | " | —C₃H₉(t) |
| Ia-9 | " | " | " | " | 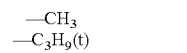 |
| Ia-10 | -2-CF₃ | " | " | " | —CH₃ |
| Ia-11 | -2-CF₃ | 1 | —H | 4 | —C₃H₉(t) |
| Ia-12 | " | " | " | " | 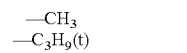 |
| Ia-13 | -3-CF₃ | " | " | " | —CH₃ |
| Ia-14 | " | " | " | " | —C₃H₉(t) |
| Ia-15 | " | " | " | " | 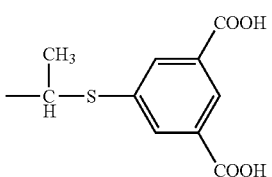 [SMILES: CC(C)Sc1cc(C(=O)O)cc(C(=O)O)c1] |
| Ia-16 | " | " | " | " | 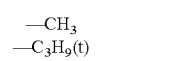 |
| Ia-17 | " | " | " | " | 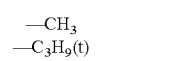 |
| Ia-18 | " | " | " | " | 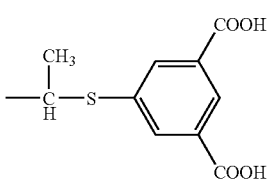 [SMILES: CC(C)Sc1cc(C(=O)O)cc(C(=O)O)c1] |
| Ia-19 | " | " | " | " | 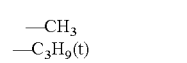 |

| | | | | | |
|---|---|---|---|---|---|
| Ia-20 | " | " | " | " | CH₃—CH(H)—S—(CH₂)₃—SO₃Na |
| Ia-21 | -4-CF₃ | 1 | —H | 4 | —CH₃ |
| Ia-22 | " | " | " | " | —C₃H₉(t) |
| Ia-23 | " | " | " | " | CH₃—CH(H)—S—(3,5-di-COOH-phenyl) |
| Ia-24 | " | " | " | " | C₄H₉—CH(H)—S—(3,5-di-COOH-phenyl) |
| Ia-25 | " | " | " | " | —(CH₂)₃—S—(3,5-di-COOH-phenyl) |
| Ia-26 | " | " | " | " | (CH₃)CH—CH₂—NH—SO₂—(3,5-di-COOH-phenyl) |
| Ia-27 | " | " | " | " | (CH₃)CH—CH₂—NH—SO₂—(4-COOH-phenyl) |
| Ia-28 | " | " | " | " | CH₃—CH(H)—S—(CH₂)₃—SO₃Na |
| Ia-29 | 4-OCF₃ | " | " | " | —C₃H₉(t) |
| Ia-30 | " | " | " | " | CH₃—CH(H)—S—(3,5-di-COOH-phenyl) |
| Ia-31 | -2-F, -3-F | 2 | —H | 3 | CH₃—CH(H)—S—(3,5-di-COOH-phenyl) |

| | | | | | |
|---|---|---|---|---|---|
| Ia-32 | -2-F, -6-F | 2 | " | 3 | 3,5-bis(COOH)-phenyl-S-CH(CH₃)- |
| Ia-33 | -2-F, -4-F | 2 | " | 3 | 3,5-bis(COOH)-phenyl-S-CH(CH₃)- |
| Ia-34 | -2-F, -5-F | 2 | " | 3 | 3,5-bis(COOH)-phenyl-S-CH(CH₃)- |
| Ia-35 | -3-F, -4-F | 2 | " | 3 | 3,5-bis(COOH)-phenyl-S-CH(CH₃)- |
| Ia-36 | " | " | " | " | —C₄H₉(t) |
| Ia-37 | " | " | " | " | NaO₃S—(CH₂)₃—S—CH(CH₃)— |
| Ia-38 | -3-F, -5-F | 2 | " | 3 | 3,5-bis(COOH)-phenyl-S-CH(CH₃)- |
| Ia-39 | " | " | " | " | —C₃H₉(t) |
| Ia-40 | " | " | " | " | NaO₃S—(CH₂)₃—S—CH(CH₃)— |
| Ia-41 | -3-CF₃, -5-CF₃ | 2 | —H | 3 | 3,5-bis(COOH)-phenyl-S-CH(CH₃)- |
| Ia-42 | " | " | " | " | —C₃H₉(t) |
| Ia-43 | -2-F, -4-CF₃ | " | " | " | 3,5-bis(COOH)-phenyl-S-CH(CH₃)- |

-continued

| | | | | | |
|---|---|---|---|---|---|
| Ia-44 | " | " | " | " | —C$_3$H$_9$(t) |
| Ia-45 | -3-F | 1 | -2-CH$_3$, -4,5,6-H | 4 | —C$_3$H$_9$(t) |
| Ia-46 | " | " | -2-COOH, -4,5,6-H | " | 3,5-bis(COOH)phenyl-S-CH(CH$_3$)— |
| Ia-47 | " | " | -4-OCH$_3$, -2,5,6-H | " | 3,5-bis(COOH)phenyl-S-CH(CH$_3$)— |
| Ia-48 | " | " | -6-OH, -2,4,5-H | " | —C$_3$H$_9$(t) |
| Ia-49 | " | " | -6-NHSO$_2$CH$_3$, -2,4,5-H | " | 3,5-bis(COOH)phenyl-S-CH(CH$_3$)— |
| Ia-50 | " | " | -6-NHSO$_2$Phe, -2,4,5-H | " | —C$_3$H$_9$(t) |
| Ia-51 | -3-F | 1 | -6-NH$_2$, -2,4,5-H | 4 | 3,5-bis(COOH)phenyl-S-CH(CH$_3$)— |
| Ia-52 | -4-F | " | -6-Cl, -2,3,5-H | " | 3,5-bis(COOH)phenyl-S-CH(CH$_3$)— |
| Ia-53 | " | " | -5-Br, -2,3,6-H | " | 3,5-bis(COOH)phenyl-S-CH(CH$_3$)— |
| Ia-54 | " | " | -5-NO$_2$, -2,3,6-H | " | 3,5-bis(COOH)phenyl-S-CH(CH$_3$)— |

-continued

| | | | | | |
|---|---|---|---|---|---|
| Ia-55 | " | " | -5-NH₂,<br>-2,3,6-H | " | 3,5-bis(COOH)phenyl-S-CH(CH₃)- |
| Ia-56 | " | " | -5-NHSO₂CH₃,<br>-2,3,6-H | " | —(CH₂)₃—S—[3,5-bis(COOH)phenyl] |
| Ia-57 | " | " | -5-NHSO₂Phe,<br>-2,3,6-H | " | —(CH₂)₃—S—[3,5-bis(COOH)phenyl] |
| Ia-58 | -2,3,4-F | 3 | —H | 2 | —(CH₂)₃—S—[3,5-bis(COOH)phenyl] |
| Ia-59 | -2,3,5-F | " | " | " | —(CH₂)₃—S—[3,5-bis(COOH)phenyl] |
| Ia-60 | -2,4,5-F | " | " | " | —(CH₂)₃—S—[3,5-bis(COOH)phenyl] |
| Ia-61 | -3,4,5-F | 3 | —H | 2 | —CH₃ |
| Ia-62 | " | " | " | " | —C₃H₉(t) |
| Ia-63 | " | " | " | " | 3,5-bis(COOH)phenyl-S-CH(CH₃)- |
| Ia-64 | -2,4,6-F | " | " | " | 3,5-bis(COOH)phenyl-S-CH(C₄H₉)- |

-continued

| ID | | | | | Structure |
|---|---|---|---|---|---|
| Ia-65 | -2,3,4,5-F | 4 | " | 1 | C4H9-CH(-)-S-[3,5-di(COOH)phenyl] |
| Ia-66 | -2,3,5,6-F | " | " | " | C4H9-CH(-)-S-[3,5-di(COOH)phenyl] |
| Ia-67 | " | " | -4-CH3 | " | C4H9-CH(-)-S-[3,5-di(COOH)phenyl] |
| Ia-68 | " | " | -4-Br | " | CH3-CH(-)-S-(CH2)3-SO3Na |
| Ia-69 | " | " | -4-COOH | " | —C3H9(t) |
| Ia-70 | " | " | -4-OH | " | CH3-CH(-)-S-[3,5-di(COOH)phenyl] |
| Ia-71 | -2,3,5,6-F | 4 | -4-NH2 | 1 | —C3H9(t) |
| Ia-72 | " | " | -4-NHSO2Phe | " | —C3H9(t) |
| Ia-73 | " | " | -4-NHSO2Me | " | —C3H9(t) |
| Ia-74 | -2,3,4,5-F | " | -6-COOH | " | —C3H9(t) |
| Ia-75 | -2,3,4,5,6-F | 5 | — | 0 | CH3-CH(-)-S-[3,5-di(COOH)phenyl] |
| Ia-76 | " | " | — | " | —C3H9(t) |
| Ia-77 | " | " | — | " | CH3-CH(-)-S-(CH2)3-SO3Na |
| Ia-78 | " | " | — | " | CH3-CH(-)-S-[3,5-di(COOH)phenyl] |
| Ia-79 | " | " | — | " | —C3H9(t) |
| Ia-80 | " | " | — | " | CH3-CH(-)-S-(CH2)3-SO3Na |

-continued
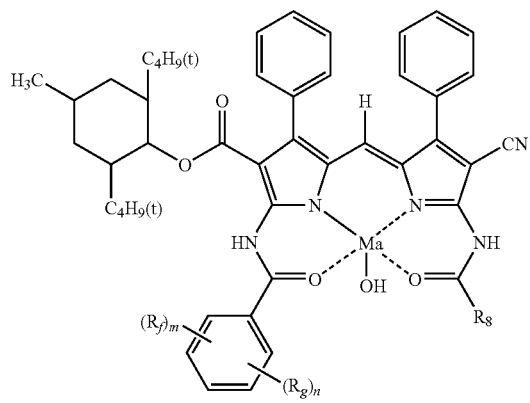
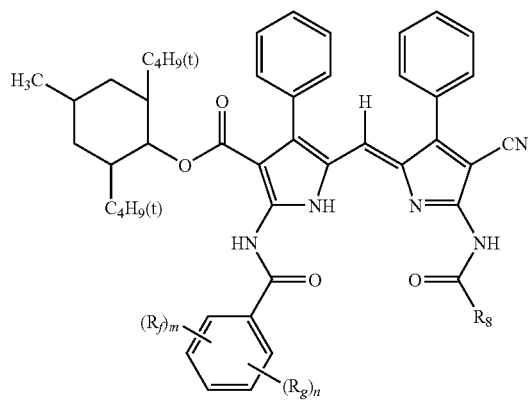
| Compound No. | $R_f$ | m | $R_g$ | n | $R_8$ |
|---|---|---|---|---|---|
| Ib-1 | -2-F | 1 | —H | 4 | —CH₃ |
| Ib-2 | " | " | " | " | —C₃H₉(t) |
| Ib-3 | " | " | " | " | 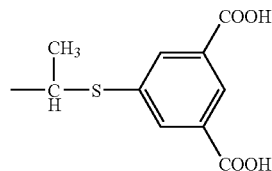 |
| Ib-4 | -3-F | " | " | " | —CH₃ |
| Ib-5 | " | " | " | " | —C₃H₉(t) |
| Ib-6 | " | " | " | " | 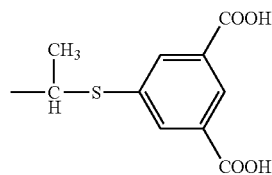 |
| Ib-7 | -4-F | " | " | " | —CH₃ |
| Ib-8 | " | " | " | " | —C₃H₉(t) |
| Ib-9 | " | " | " | " | 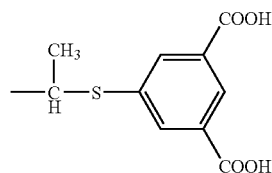 |

-continued

| | | | | | |
|---|---|---|---|---|---|
| Ib-10 | -2-CF$_3$ | " | " | " | —CH$_3$ |
| Ib-11 | -2-CF$_3$ | 1 | —H | 4 | —C$_3$H$_9$(t) |
| Ib-12 | " | " | " | " | ![structure: CH(CH$_3$)—S—C$_6$H$_3$(COOH)$_2$] |
| Ib-13 | -3-CF$_3$ | " | " | " | —CH$_3$ |
| Ib-14 | " | " | " | " | —C$_3$H$_9$(t) |
| Ib-15 | " | " | " | " | ![structure: CH(CH$_3$)—S—C$_6$H$_3$(COOH)$_2$] |
| Ib-16 | " | " | " | " | ![structure: CH(C$_4$H$_9$)—S—C$_6$H$_3$(COOH)$_2$] |
| Ib-17 | " | " | " | " | ![structure: —(CH$_2$)$_3$—S—C$_6$H$_3$(COOH)$_2$] |
| Ib-18 | " | " | " | " | ![structure: (CH$_3$)CH—CH$_2$—NH—SO$_2$—C$_6$H$_3$(COOH)$_2$] |
| Ib-19 | " | " | " | " | ![structure: (CH$_3$)CH—CH$_2$—NH—SO$_2$—C$_6$H$_4$—COOH] |
| Ib-20 | " | " | " | " | ![structure: CH(CH$_3$)—S—(CH$_2$)$_3$—SO$_3$Na] |
| Ib-21 | -4-CF$_3$ | 1 | —H | 4 | —CH$_3$ |
| Ib-22 | " | " | " | " | —C$_3$H$_9$(t) |
| Ib-23 | " | " | " | " | ![structure: CH(CH$_3$)—S—C$_6$H$_3$(COOH)$_2$] |

-continued
| | | | | | |
|---|---|---|---|---|---|
| Ib-24 | " | " | " | " | 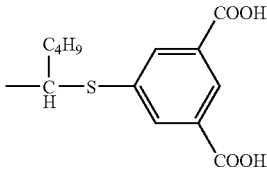 |
| Ib-25 | " | " | " | " | 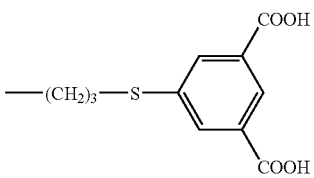 |
| Ib-26 | " | " | " | " | 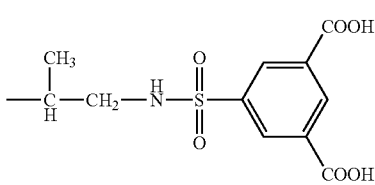 |
| Ib-27 | " | " | " | " | 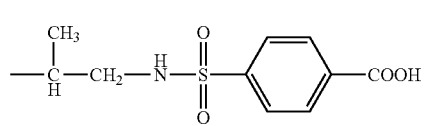 |
| Ib-28 | " | " | " | " | 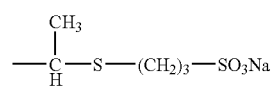 |
| Ib-29 | -4-OCF$_3$ | " | " | " | —C$_3$H$_9$(t) |
| Ib-30 | " | " | " | " | 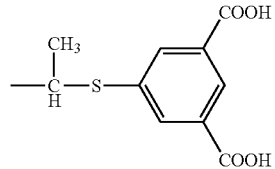 |
| Ib-31 | -2-F, -3-F | 2 | —H | 3 | 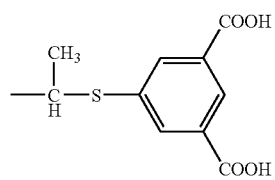 |
| Ib-32 | -2-F, -6-F | 2 | " | 3 | 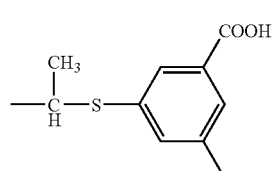 |
| Ib-33 | -2-F, -4-F | 2 | " | 3 | 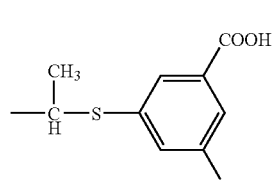 |

-continued

| | | | | | |
|---|---|---|---|---|---|
| Ib-34 | -2-F, -5-F | 2 | " | 3 | 3,5-bis(COOH)-phenyl-S-CH(CH₃)- |
| Ib-35 | -3-F, -4-F | 2 | " | 3 | 3,5-bis(COOH)-phenyl-S-CH(CH₃)- |
| Ib-36 | " | " | " | " | —C₃H₉(t) |
| Ib-37 | " | " | " | " | NaO₃S-(CH₂)₃-S-CH(CH₃)- |
| Ib-38 | -3-F, -5-F | 2 | " | 3 | 3,5-bis(COOH)-phenyl-S-CH(CH₃)- |
| Ib-39 | " | " | " | " | —C₃H₉(t) |
| Ib-40 | " | " | " | " | NaO₃S-(CH₂)₃-S-CH(CH₃)- |
| Ib-41 | -3-CF₃, -5-CF₃ | 2 | —H | 3 | 3,5-bis(COOH)-phenyl-S-CH(CH₃)- |
| Ib-42 | " | " | " | " | —C₃H₉(t) |
| Ib-43 | -2-F, -4-CF₃ | " | " | " | 3,5-bis(COOH)-phenyl-S-CH(CH₃)- |
| Ib-44 | " | " | " | " | —C₃H₉(t) |
| Ib-45 | -3-F | 1 | -2-CH₃, -4,5,6-H | 4 | —C₃H₉(t) |
| Ib-46 | " | " | -2-COOH, -4,5,6-H | " | 3,5-bis(COOH)-phenyl-S-CH(CH₃)- |

-continued

| ID | | | | | Structure |
|---|---|---|---|---|---|
| Ib-47 | " | " | -4-OCH₃, -2,5,6-H | " | CH₃-CH(-)-S- attached to benzene with 3,5-di-COOH |
| Ib-48 | " | " | -6-OH, -2,4,5-H | " | —C₃H₉(t) |
| Ib-49 | " | " | -6-NHSO₂CH₃, -2,4,5-H | " | CH₃-CH(-)-S- attached to benzene with 3,5-di-COOH |
| Ib-50 | " | " | -6-NHSO₂Phe, -2,4,5-H | " | —C₃H₉(t) |
| Ib-51 | -3-F | 1 | -6-NH₂, -2,4,5-H | 4 | CH₃-CH(-)-S- attached to benzene with 3,5-di-COOH |
| Ib-52 | -4-F | " | -6-Cl, -2,3,5-H | " | CH₃-CH(-)-S- attached to benzene with 3,5-di-COOH |
| Ib-53 | " | " | -5-Br, -2,3,6-H | " | CH₃-CH(-)-S- attached to benzene with 3,5-di-COOH |
| Ib-54 | " | " | -5-NO₂, -2,3,6-H | " | CH₃-CH(-)-S- attached to benzene with 3,5-di-COOH |
| Ib-55 | " | " | -5-NH₂, -2,3,6-H | " | CH₃-CH(-)-S- attached to benzene with 3,5-di-COOH |
| Ib-56 | " | " | -5-NHSO₂CH₃, -2,3,6-H | " | —(CH₂)₃—S— attached to benzene with 3,5-di-COOH |

-continued
| | | | | | |
|---|---|---|---|---|---|
| Ib-57 | " | " | -5-NHSO₂Phe, -2,3,6-H | " | 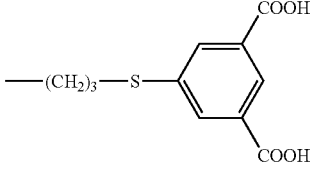 |
| Ib-58 | -2,3,4-F | 3 | —H | 2 | 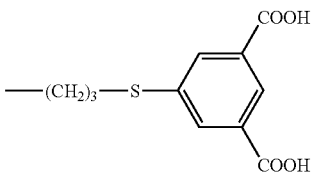 |
| Ib-59 | -2,3,5-F | " | " | " | 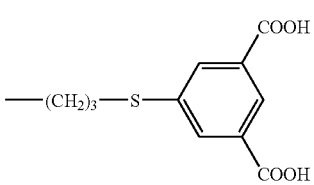 |
| Ib-60 | -2,4,5-F | " | " | " | 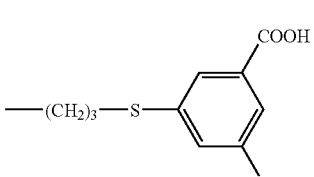 |
| Ib-61 | -3,4,5-F | 3 | —H | 2 | —CH₃ |
| Ib-62 | " | " | " | " | —C₃H₉(t) |
| Ib-63 | " | " | " | " | 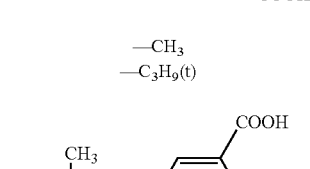 |
| Ib-64 | -2,4,6-F | " | " | " | 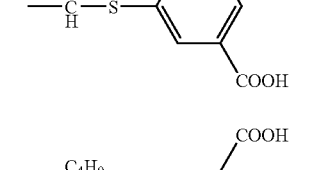 |
| Ib-65 | -2,3,4,5-F | 4 | " | 1 | 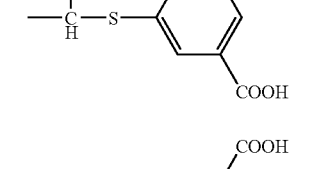 |
| Ib-66 | -2,3,5,6-F | " | " | " | 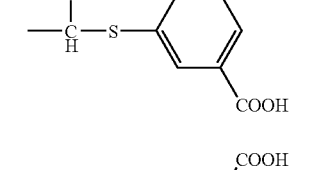 |

-continued
| | | | | | |
|---|---|---|---|---|---|
| Ib-67 | " | " | -4-CH₃ | " | 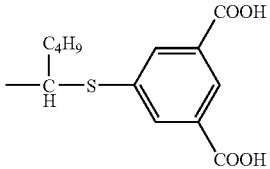 |
| Ib-68 | " | " | -4-Br | " | 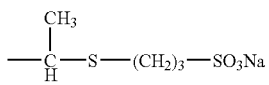 |
| Ib-69 | " | " | -4-COOH | " | —C₃H₉(t) |
| Ib-70 | " | " | -4-OH | " | 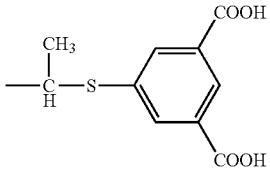 [SMILES: CC(C)Sc1cc(C(=O)O)cc(C(=O)O)c1] |
| Ib-71 | -2,3,5,6-F | 4 | 4-NH₂ | 1 | —C₃H₉(t) |
| Ib-72 | " | " | -4-NHSO₂Phe | " | —C₃H₉(t) |
| Ib-73 | " | " | -4-NHSO₂Me | " | —C₃H₉(t) |
| Ib-74 | -2,3,4,5-F | " | -6-COOH | " | —C₃H₉(t) |
| Ib-75 | -2,3,4,5,6-F | 5 | — | 0 | 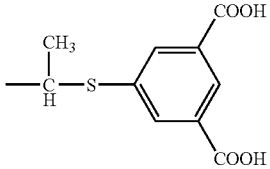 |
| Ib-76 | " | " | — | " | —C₃H₉(t) |
| Ib-77 | " | " | — | " | 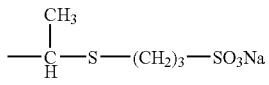 |
| Ib-78 | " | " | — | " | 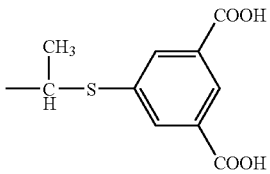 [SMILES: CC(C)Sc1cc(C(=O)O)cc(C(=O)O)c1] |
| Ib-79 | " | " | — | " | —C₃H₉(t) |
| Ib-80 | " | " | — | " | 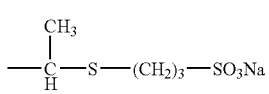 |
Phe: phenyl group

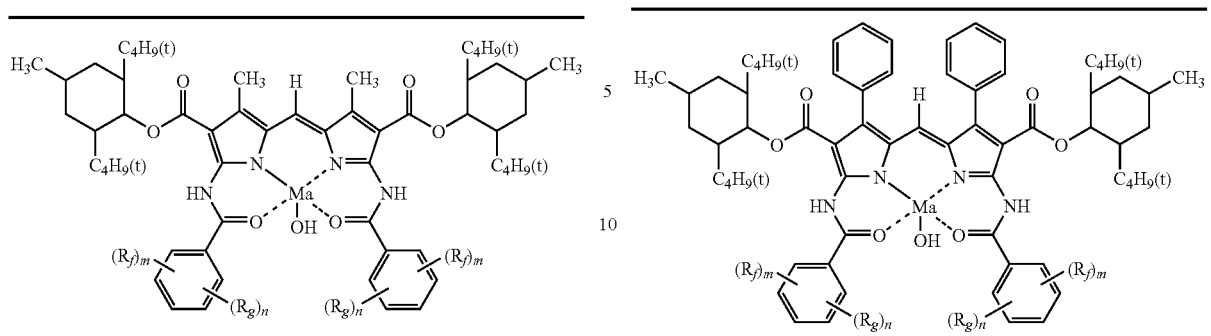

| Compound No. | $R_f$ | m | $R_g$ | n |
|---|---|---|---|---|
| IIa-1 | -2-F | 1 | —H | 4 |
| IIa-2 | -3-F | " | " | " |
| IIa-3 | -4-F | " | " | " |
| IIa-4 | -3-F | " | " | " |
| IIa-5 | -2-CF$_3$ | " | " | " |
| IIa-6 | -3-CF$_3$ | " | " | " |
| IIa-7 | -4-CF$_3$ | " | " | " |
| IIa-8 | -4-OCF$_3$ | " | " | " |
| IIa-9 | -2-F, -3-F | 2 | " | 3 |
| IIa-10 | -2-F, -6-F | " | " | " |
| IIa-11 | -2-F, -4-F | " | " | " |
| IIa-12 | -2-F, -5-F | " | " | " |
| IIa-13 | -3-F, -4-F | " | " | " |
| IIa-14 | -3-CF$_3$, -5-CF$_3$ | " | " | " |
| IIa-15 | -2-F, -4-CF$_3$ | " | " | " |
| IIa-16 | -3-F | 1 | -2-CH$_3$, -4,5,6-H | 4 |
| IIa-17 | " | " | -2-COOH, -4,5,6-H | " |
| IIa-18 | " | " | -4-OCH$_3$, -2,5,6-H | " |
| IIa-19 | " | " | -6-OH, -2,4,5-H | " |
| IIa-20 | " | " | -6-NHSO$_2$CH$_3$, -2,4,5-H | " |
| IIa-21 | -3-F | 1 | -6-NHSO$_2$Phe, -2,4,5-H | 4 |
| IIa-22 | " | " | -6-NH$_2$, -2,4,5-H | " |
| IIa-23 | -4-F | " | -6-Cl, -2,3,5-H | " |
| IIa-24 | " | " | -5-Br, -2,3,6-H | " |
| IIa-25 | " | " | -5-NO$_2$, -2,3,6-H | " |
| IIa-26 | " | " | -5-NH$_2$, -2,3,6-H | " |
| IIa-27 | " | " | -5-NHSO$_2$CH$_3$, -2,3,6-H | " |
| IIa-28 | " | " | -5-NHSO$_2$Phe, -2,3,6-H | " |
| IIa-29 | -2,3,4-F | 3 | —H | 2 |
| IIa-30 | -2,3,5-F | " | " | " |
| IIa-31 | -2,4,5-F | " | " | " |
| IIa-32 | -3,4,5-F | " | " | " |
| IIa-33 | -2,4,6-F | " | " | " |
| IIa-34 | -2,3,4,5-F | 4 | " | 1 |
| IIa-35 | -2,3,5,6-F | " | " | " |
| IIa-36 | " | " | -4-CH$_3$ | " |
| IIa-37 | " | " | -4-Br | " |
| IIa-38 | " | " | -4-COOH | " |
| IIa-39 | " | " | -4-OH | " |
| IIa-40 | -2,3,4,5,6-F | 5 | — | 0 |

Phe: phenyl group

| Compound No. | $R_f$ | m | $R_g$ | n |
|---|---|---|---|---|
| IIb-1 | -2-F | 1 | H | 4 |
| IIb-2 | -3-F | " | " | " |
| IIb-3 | -4-F | " | " | " |
| IIb-4 | -3-F | " | " | " |
| IIb-5 | -2-CF$_3$ | " | " | " |
| IIb-6 | -3-CF$_3$ | " | " | " |
| IIb-7 | -4-CF$_3$ | " | " | " |
| IIb-8 | -4-OCF$_3$ | " | " | " |
| IIb-9 | -2-F, -3-F | 2 | " | 3 |
| IIb-10 | -2-F, -6-F | " | " | " |
| IIb-11 | -2-F, -4-F | " | " | " |
| IIb-12 | -2-F, -5-F | " | " | " |
| IIb-13 | -3-F, -4-F | " | " | " |
| IIb-14 | -3-CF$_3$, -5-CF$_3$ | " | " | " |
| IIb-15 | -2-F, -4-CF$_3$ | " | " | " |
| IIb-16 | -3-F | 1 | -2-CH$_3$, -4,5,6-H | 4 |
| IIb-17 | " | " | -2-COOH, -4,5,6-H | " |
| IIb-18 | " | " | -4-OCH$_3$, -2,5,6-H | " |
| IIb-19 | " | " | -6-OH, -2,4,5-H | " |
| IIb-20 | " | " | -6-NHSO$_2$CH$_3$, -2,4,5-H | " |
| IIb-21 | -3-F | 1 | -6-NHSO$_2$Phe, -2,4,5-H | 4 |
| IIb-22 | " | " | -6-NH$_2$, -2,4,5-H | " |
| IIb-23 | -4-F | " | -6-Cl, -2,3,5-H | " |
| IIb-24 | " | " | -5-Br, -2,3,6-H | " |
| IIb-25 | " | " | -5-NO$_2$, -2,3,6-H | " |
| IIb-26 | " | " | -5-NH$_2$, -2,3,6-H | " |
| IIb-27 | " | " | -5-NHSO$_2$CH$_3$, -2,3,6-H | " |
| IIb-28 | " | " | -5-NHSO$_2$Phe, -2,3,6-H | " |
| IIb-29 | -2,3,4-F | 3 | —H | 2 |
| IIb-30 | -2,3,5-F | " | " | " |
| IIb-31 | -2,4,5-F | " | " | " |
| IIb-32 | -3,4,5-F | " | " | " |
| IIb-33 | -2,4,6-F | " | " | " |
| IIb-34 | -2,3,4,5-F | 4 | " | 1 |
| IIb-35 | -2,3,5,6-F | " | " | " |
| IIb-36 | " | " | -4-CH$_3$ | " |
| IIb-37 | " | " | -4-Br | " |
| IIb-38 | " | " | -4-COOH | " |
| IIb-39 | " | " | -4-OH | " |
| IIb-40 | -2,3,4,5,6-F | 5 | — | 0 |

Phe: phenyl group

The metal complex compound-1 (including the specific metal complex compounds-2, -3, and -4) obtained from fluorine-containing dipyrromethene compound represented by Formula (1) can be synthesized by the methods such as those described in U.S. Pat. Nos. 4,774,339 and 5,433,896, JP-A Nos. 2001-240761 and 2002-155052, JP No. 3614586, "Aust. J. Chem.", 11, 1835-1845 (1965), and J. H. Boger et al, "Heteroatom Chemistry", Val, No. 5, 389 (1990).

Here, examples of synthetic intermediates include the fluorine-containing dipyrromethene compound represented by Formula (6) or (7) and tautomers thereof.

As one example of methods for synthesizing the dipyrromethene metal complex compound, the synthetic schemes (reaction scheme 1) of the exemplary compounds Ia-15, Ib-15, IIa-6, and IIb-6 are shown below. The synthesis of each intermediate and the like will be described in detail in the Examples described below. The following intermediates 11 to 14 are specific examples of the fluorine-containing dipyrromethene compound (including tautomers thereof) represented by Formula (6) or (7).

Reaction scheme 1

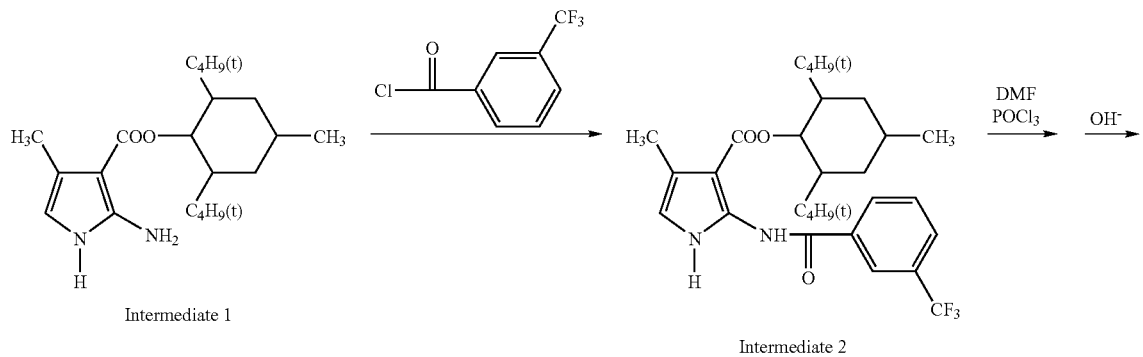

Intermediate 1 → Intermediate 2

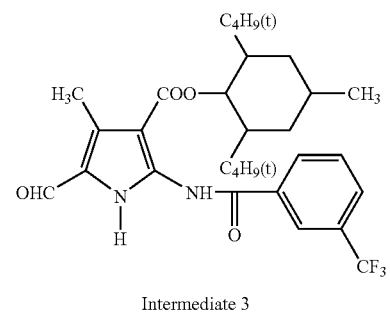

Intermediate 3

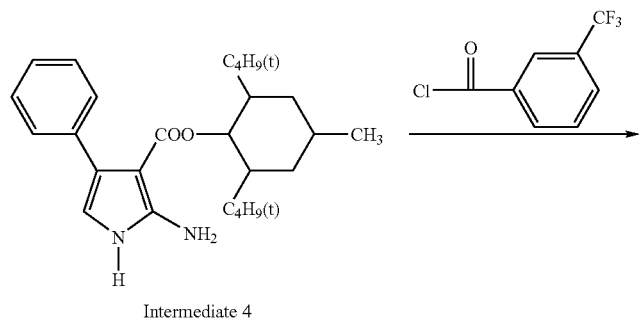

Intermediate 4

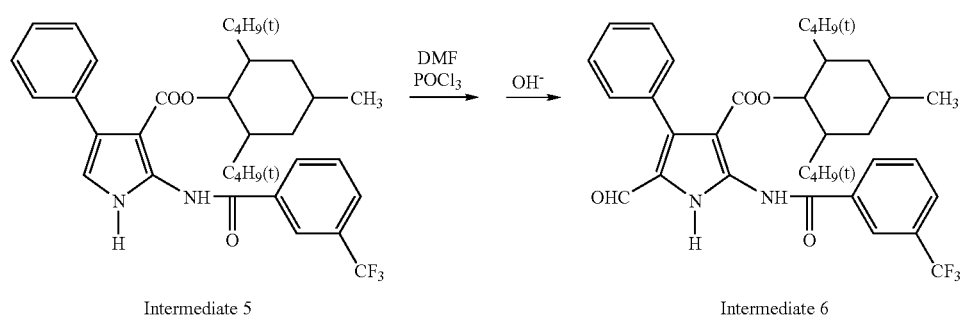

Intermediate 5 → Intermediate 6

-continued
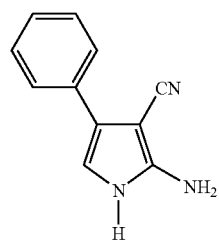 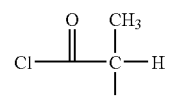 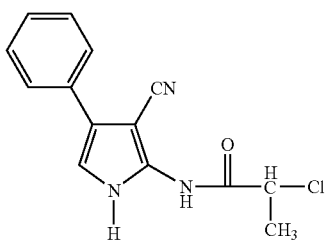 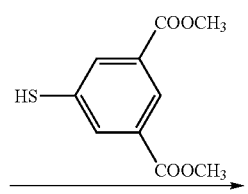
Intermediate 7    Intermediate 8
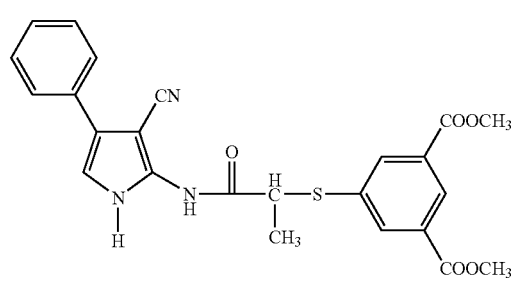 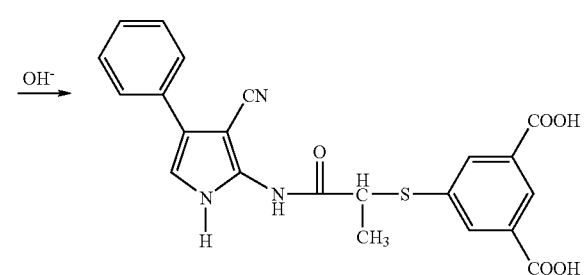
Intermediate 9    Intermediate 10
Intermediate 3 + Intermediate 10 →
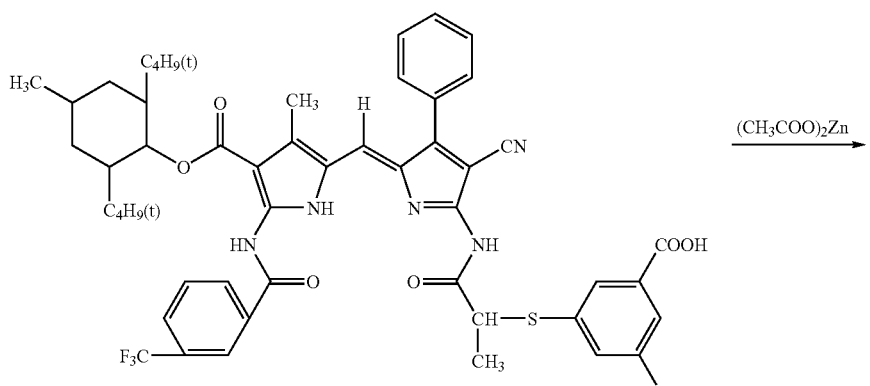 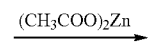
Intermediate 11
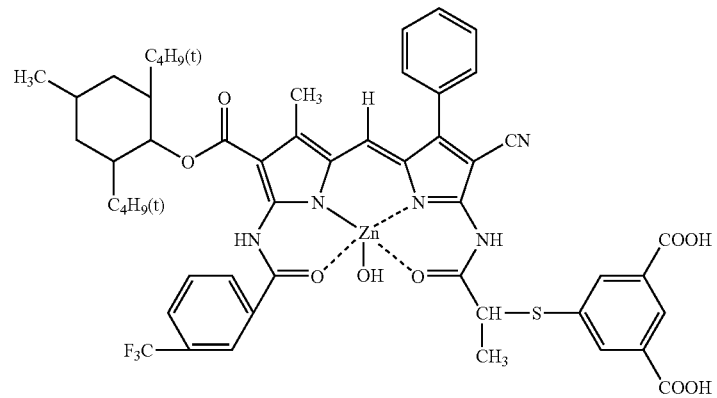
Exemplary compound Ia-15

-continued
Intermediate 6 + Intermediate 10 ⟶ 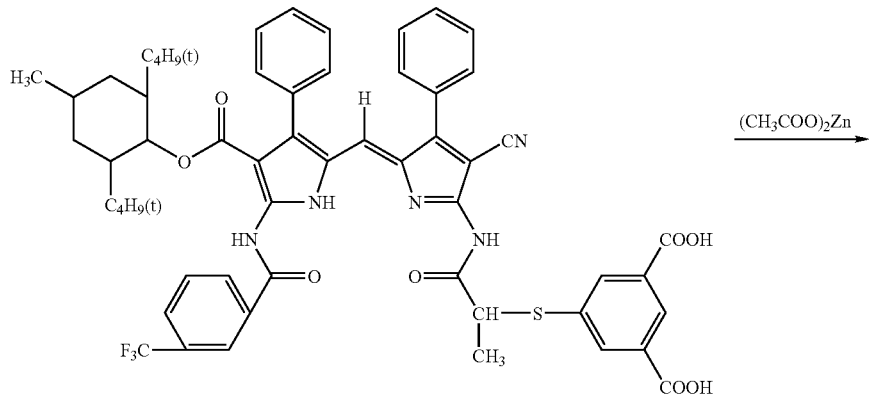
Intermediate 12
$(CH_3COO)_2Zn$ ⟶
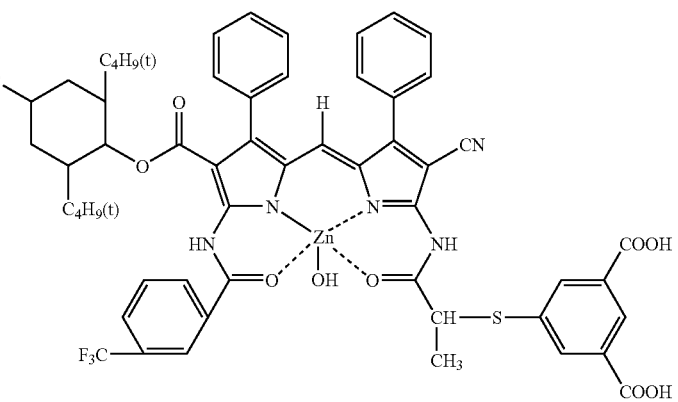
Exemplary compound Ib-15
Intermediate 2 $\xrightarrow{CH(OC_2H_5)_3}$ 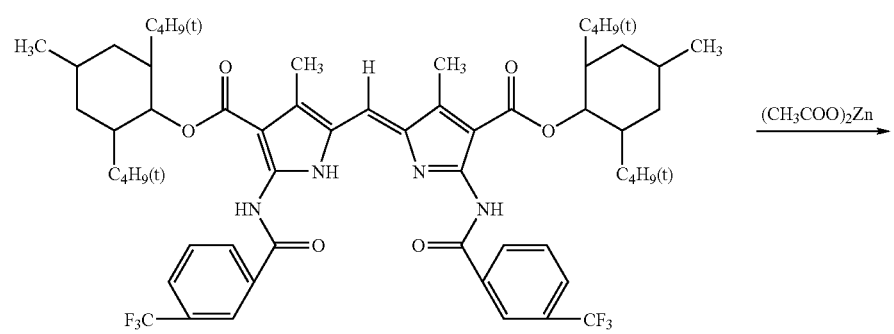
Intermediate 13
$(CH_3COO)_2Zn$ ⟶
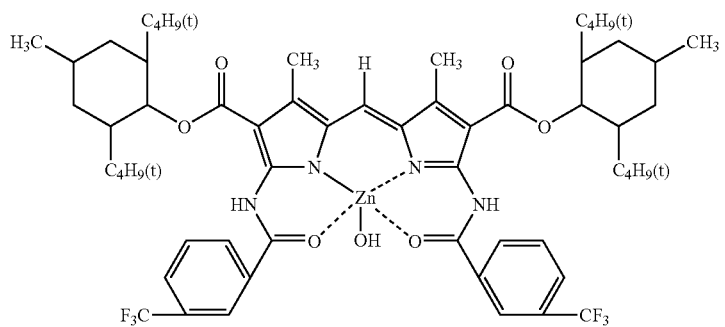
Exemplary Compound IIa-6

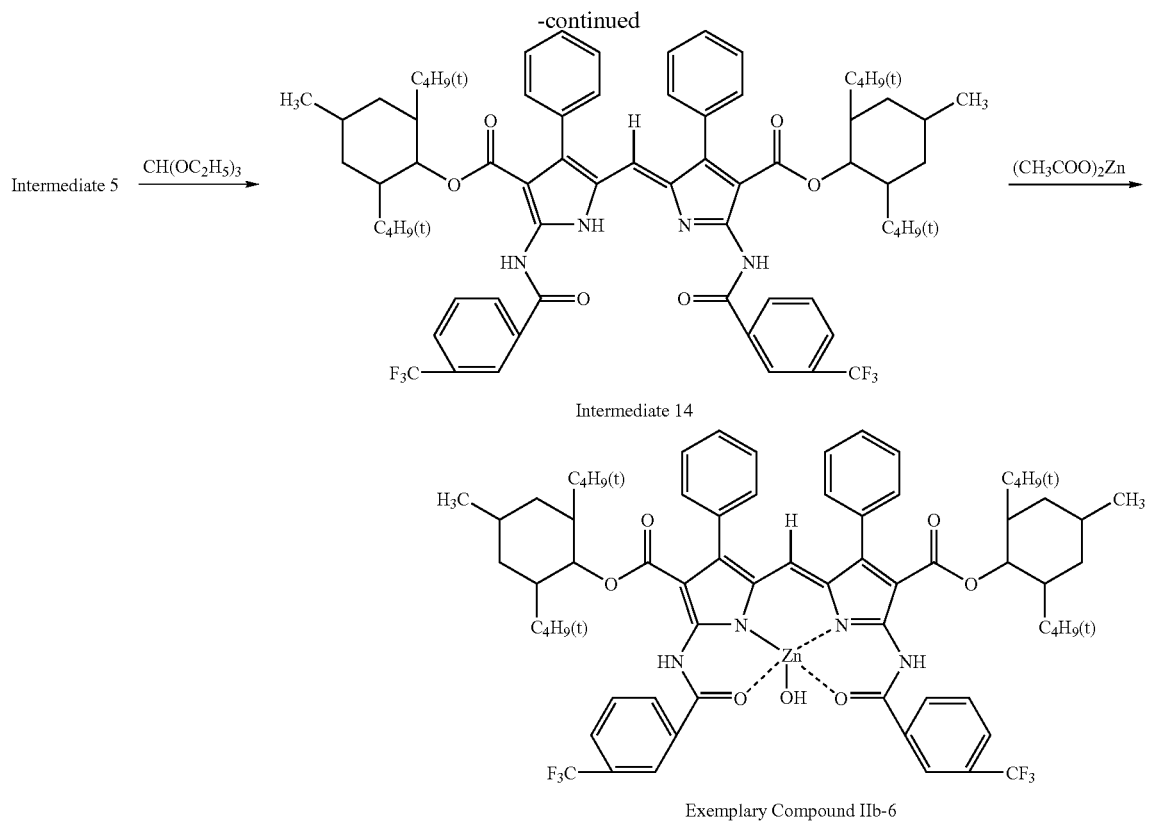

Exemplary Compound IIb-6

In the colored curable composition of the invention, the above-described specific metal complex compound-1 (including the specific metal complex compounds-2, -3 and -4) may be used singly or in combination of two or more kinds thereof.

The content of the specific metal complex compound-1 of the invention in the colored curable composition varies depending on the molecular weight and the molar absorption coefficient thereof, and is preferably from 0.5% by mass to 80% by mass, more preferably from 0.5% by mass to 60% by mass, and most preferably from 0.5% by mass to 50% by mass, with respect to the total solid content of the colored curable composition.

Other Coloring Materials

In addition to the above-described specific metal complex compound-1 (including the specific metal complex compounds-2, -3 and -4), the colored curable composition of the invention (and a color filter formed by using this colored curable composition) may contain other coloring materials, such as a triarylmethane-based coloring material having a maximum absorption in a wavelength region of from 550 nm to 650 nm. Examples thereof include C.I. Acid Blue 7, C.I. Acid Blue 83, C.I. Acid Blue 90, C.I. Solvent Blue 38, C.I. Acid Violet 17, C.I. Acid Violet 49 and C.I. Acid Green 3.

Examples of the coloring materials further include xanthene-based dyes having a maximum absorption in a wavelength region of from 500 nm to 600 nm, such as C.I. Acid Red 289.

Examples of the coloring materials further include tetraazaporphyrin-based cyan dyes having a maximum absorption in a wavelength region of from 600 nm to 680 nm, such as the specific dye-A described in the specification of U.S. Patent Application Publication No. 2008/0076044.

The content of the triarylmethane-based coloring material is not specifically limited as far as the effect of the invention is not impaired, and preferably from 0.5% by mass to 50% by mass, with respect to the total solid content of the colored curable composition of the invention.

Binder

The colored curable composition of the invention preferably contains at least one type of binder resin. The binder resin used in the invention is not particularly limited as long as it is alkali-soluble, and is preferably selected in view of heat resistance, developability, availability, and the like.

The alkali-soluble binder is preferably a linear organic high-molecular polymer, which is soluble in organic solvents and developable with an aqueous weak-alkaline solution. Examples of such linear organic high-molecular polymer include a polymer having a carboxylic acid group at a side chain thereof, for example, a methacrylic acid copolymer, an acrylic acid copolymer, an itaconic acid copolymer, a crotonic acid copolymer, a maleic acid copolymer or a partially-esterified maleic acid copolymer such as those described in JP-A Nos. 59-44615, 59-53836 and 59-71048, and JP-B Nos. 54-34327, 58-12577 and 54-25957. In particular, an acidic cellulose derivative having a carboxylic acid group at a side chain thereof is useful. In addition, preferable examples thereof include a polymer obtained by adding an acid anhydride to a polymer having a hydroxyl group; and a polyhydroxystyrene resin, a polysiloxane resin, poly(2-hydroxyethyl (meth)acrylate), polyvinylpyrrolidone, polyethylene oxide and polyvinyl alcohol.

The alkali-soluble binder may be formed using a monomer having a hydrophilic group as a copolymerization component. Examples of the monomer having a hydrophilic group include alkoxyalkyl (meth)acrylate, hydroxyalkyl (meth)

acrylate, glycerol (meth)acrylate, (meth)acrylamide, N-methylol acrylamide, secondary or tertiary alkyl acrylamide, dialkylaminoalkyl (meth)acrylate, morpholine (meth)acrylate, N-vinylpyrrolidone, N-vinylcaprolactam, vinylimidazole, vinyltriazole, methyl (meth)acrylate, ethyl (meth)acrylate, branched or linear propyl (meth)acrylate, branched or linear butyl (meth)acrylate, and phenoxyhydroxypropyl (meth)acrylate.

Examples of monomer having a hydrophilic group further include a monomer having a tetrahydrofurfuryl group, a phosphate moiety, a phosphate ester moiety, a quaternary ammonium salt moiety, an ethyleneoxy chain, a propyleneoxy chain, sulfonic acid moiety, a sulfonic acid salt moiety, or a morpholinoethyl group.

The binder resin may have a polymerizable group at a side chain thereof for improving the cross-linking efficiency. Preferable examples of the alkali-soluble binder include a polymer having an allyl group, a (meth)acrylic group or an allyloxyalkyl group at a side chain thereof. Examples of the polymer having a polymerizable group include KS RESIST-106 (manufactured by Osaka Organic Chemical Industry Ltd.), and CYCLOMER P Series (manufactured by Daicel Chemical Industries, Ltd.).

In order to increase the strength of a cured film, alcohol-soluble nylon, and polyether of 2,2-bis(4-hydroxyphenyl)-propane and epichlorohydrine are also useful.

Among the binder resins, the binder resin of the invention is preferably, from the viewpoint of heat resistance, polyhydroxy styrene resin, polysiloxane resin, acrylic resin, acrylamide resin, or acryl-acrylamide copolymer resin. In order to control developability, the binder resin is preferably an acrylic resin, an acrylamide resin, or an acryl-acrylamide copolymer resin. Preferable examples of the acrylic resin include a copolymer obtained by polymerizing monomers selected from a benzyl (meth)acrylate, a (meth)acryl acid, a hydroxyethyl (meth)acrylate, or a (meth)acrylamide; and KS RESIST-106 (manufactured by Osaka Organic Chemical Industry Ltd.) and CYCLOMER P Series (manufactured by Daicel Chemical Industries, Ltd.).

The binder resin may be an alkali-soluble phenol resin. The alkali-soluble phenol resin is suitably used when the colored curable composition of the invention is used as a positive-working composition. Examples of the alkali-soluble phenol resin include a novolak resin and a vinyl polymer.

Examples of the novolak resin include resins produced, for example, by condensing phenols and aldehydes in the presence of acid catalyst. Examples of the phenols include phenol, cresol, ethyl phenol, butyl phenol, xylenol, phenyl phenol, catechol, resorcinol, pyrogallol, naphthol and bisphenol A.

Examples of the aldehydes include formaldehyde, paraformaldehyde, acetaldehyde, propionaldehyde and benzaldehyde.

The phenols may be used singly or in combination of two or more kinds thereof, and the aldehydes may be used singly or in combination of two or more kinds thereof.

Specific examples of the novolak resin include a condensation product of formalin and methacresol, paracresol, or a mixture of methacresol and paracresol.

Molecular weight distribution of the novolak resin may be adjusted, for example, by fractionation. The novolak resin may also be mixed with a low-molecular component having a phenolic hydroxy group such as bisphenol C or bisphenol A.

The binder resin is preferably a polymer having a weight average molecular weight (polystyrene-equivalent value measured according to a GPC method) of from 1,000 to $2 \times 10^5$, more preferably of from 2,000 to $1 \times 10^5$, and still more preferably of from 5,000 to $5 \times 10^4$.

The content of the binder resin in the colored curable composition of the invention is preferably from 10% by mass to 90% by mass, more preferably from 20% by mass to 80% by mass, particularly from 30% by mass to 70% by mass, with respect to the total solid content of the colored curable composition.

Crosslinking Agent

The colored curable composition of the invention is higher in color purity, has a higher absorption coefficient allowing reduction in the thickness, and is better in fastness compared with a conventional composition. It is possible to obtain a highly-cured film by adding a crosslinking agent.

The cross-linking agent used in the invention is not particularly limited, as long as it can cure a film by the cross-linking reaction. Examples of the cross-linking agent include (a) an epoxy resin, (b) a melamine compound, a guanamine compound, a glycoluril compound and a urea compound, each of which is substituted with at least one substituent selected from a methylol group, an alkoxymethyl group or an acyloxymethyl group, and (c) a phenol compound, a naphthol compound or a hydroxyanthracene compound, each of which is substituted with at least one substituent selected from a methylol group, an alkoxymethyl group or an acyloxymethyl group. Among these compounds, a multifunctional epoxy resin is preferable.

As (a) the epoxy resin, any resins having epoxy groups and having cross-linking properties may be used. Examples of (a) the epoxy resin include bis(glycidyl group)-containing low-molecular compounds such as bisphenol A diglycidyl ether, ethyleneglycol diglycidyl ether, butanediol diglycidyl ether, hexanediol diglycidyl ether, dihydroxybiphenyl diglycidyl ether, diglycidyl phthalate and N,N-diglycidylaniline; tris(glycidyl group)-containing low-molecular compounds such as trimethylolpropane triglycidyl ether, trimethylolphenol triglycidyl ether and TrisP-PA triglycidyl ether; tetrakis(glycidyl group)-containing low-molecular compounds such as pentaerythritol tetraglycidyl ether and tetramethylol bisphenol A tetraglycidyl ether; poly(glycidyl group)-containing low-molecular compounds such as dipentaerythritol pentaglycidyl ether and dipentaerythritol hexaglycidyl ether; and glycidyl group-containing high-molecular compounds such as polyglycidyl (meth)acrylate and a 1,2-epoxy-4-(2-oxiranyl)cyclohexane adduct of 2,2-bis(hydroxymethyl)-1-butanol.

The total number of the methylol, alkoxymethyl and acyloxymethyl groups, by which the cross-linking agent of (b) is substituted, is from 2 to 6 in the case of the melamine compound, and is from 2 to 4 in the case of the glycoluril compound, the guanamine compound, or the urea compound. The total number of these groups is preferably 5 or 6 in the case of the melamine compound, and is preferably 3 or 4 in the case of the glycoluril compound, the guanamine compound, or the urea compound.

Hereinafter, (b) the melamine compound, guanamine compound, glycoluril compound and urea compound are sometimes collectively referred to as a "compound (b)" or "compounds (b)" (which include a methylol group-containing compound, an alkoxymethyl group-containing compound, and an acyloxymethyl group-containing compound).

A compound (b) that contains a methylol group can be obtained by heating a compound (b) that contains an alkoxymethyl group in alcohol solution in the presence of an acid catalyst such as hydrochloric acid, sulfuric acid, nitric acid or methanesulfonic acid. A compound (b) that contains an acyloxymethyl group can be obtained by mixing and stirring a compound (b) that contains a methylol group with acylchloride in the presence of a base catalyst.

Hereinafter, specific examples of the compound (b) having a substituent are described.

Examples of the melamine compound include a hexamethylolmelamine, hexamethoxymethylmelamine, compounds in which 1 to 5 methylol groups of hexamethylolmelamine are methoxymethylated and mixtures of these compounds, hexamethoxyethylmelamine, hexaacyloxymethylmelamine, and compounds in which 1 to 5 methylol groups of hexamethylolmelamine are acyloxymethylated and mixtures of there compounds.

Examples of the guanamine compound include tetramethylolguanamine, tetramethoxymethylguanamine, compounds in which 1 to 3 methylol groups of tetramethylolguanamine are methoxymethylated or mixtures of these compounds, tetramethoxyethylguanamine, tetraacyloxymethylguanamine, and compounds in which 1 to 3 methylol groups of tetramethylolguanamine are acyloxymethylated and mixtures of these compounds.

Examples of the glycoluril compound include tetramethylolglycoluril, tetramethoxymethylglycoluril, compounds in which 1 to 3 methylol groups of tetramethylolglycoluril are methoxymethylated or mixtures of these compounds, and compounds in which 1 to 3 methylol groups of tetramethylol glycoluril are acyloxymethylated and mixtures of these compounds.

Examples of the urea compound include tetramethylolurea, tetramethoxymethylurea, compounds in which 1 to 3 methylol groups of tetramethylolurea are methoxymethylated and mixtures of these compounds, and tetramethoxyethylurea.

The compounds (b) may be used singly or in combination of two or more kinds thereof.

The cross-linking agent (c) (i.e., a phenol compound, a naphthol compound or a hydroxyanthracene compound, each of which is substituted with at least one substituent selected from a methylol group, an alkoxymethyl group or an acyloxymethyl group) suppresses intermixing with an overcoated photoresist by thermal cross-linking and can further increase a film strength, similarly to the compounds (b).

Hereinafter, these compounds are sometimes collectively referred to as a "compound (c)" or "compounds (c)" (which include a methylol group-containing compound, an alkoxymethyl group-containing compound, and an acyloxymethyl group-containing compound).

The total number of the methylol, acyloxymethyl, and alkoxymethyl groups contained in the cross-linking agent (c) is at least two per one molecule. In consideration of thermal cross-linking ability and storage stability, the skeleton of the phenol compound are preferably substituted at all of 2- and 4-positions. It is preferable that the skeleton of the naphthol compound and the skeleton of the hydroxyanthracene compound are substituted at all of the ortho- and para-positions to the OH groups, respectively. The skeleton of phenol compound may be unsubstituted or substituted at 3- and 5-positions. The skeleton of the naphthol compound may be unsubstituted or substituted at positions other than the ortho-positions to the OH groups A compound (c) that contains a methylol group can be obtained by using a compound, in which ortho- or para-position (2- or 4-position) of the phenolic OH group is a hydrogen atom, as a raw material and reacting it with formalin in the presence of a base catalyst, such as sodium hydroxide, potassium hydroxide, ammonia or tetraalkylammonium hydroxide.

A compound (c) that contains an alkoxymethyl group can be obtained by heating the methylol group-containing compound in an alcohol, in the presence of an acid catalyst such as hydrochloric acid, sulfuric acid, nitric acid or methanesulfonic acid.

A compound (c) that contains an acyloxymethyl group can be obtained by reacting the methylol group-containing compound with an acyl chloride in the presence of a base catalyst.

Examples of the backbone compound of the cross-linking agent (c) include phenol, naphthol and hydroxyanthracene compounds, in which the ortho- or para-position to the phenolic OH group is unsubstituted. Specific examples thereof include phenol, isomers of cresol, 2,3-xylenol, 2,5-xylenol, 3,4-xylenol, 3,5-xylenol, bisphenols such as bisphenol A, 4,4'-bishydroxy biphenyl, TrisP-PA (manufactured by Honshu Chemical Industry Co., Ltd.), naphthol, dihydroxynaphthalene and 2,7-dihydroxyanthracene.

Specific examples of the compounds (c) as the cross-linking agent include trimethylolphenol, tri(methoxymethyl)phenol, phenol compounds in which 1 or 2 methylol groups of trimethylolphenol are methoxymethylated, trimethylol-3-cresol, tri(methoxymethyl)-3-cresol, phenol compounds in which 1 or 2 methylol groups of trimethylol-3-cresol are methoxymethylated, a dimethylol cresol such as 2,6 dimethylol-4 cresol, tetramethylol bisphenol A, tetramethoxymethyl bisphenol A, phenol compounds in which 1 to 3 methylol groups of tetramethylol bisphenol A are methoxymethylated, tetramethylol-4,4'-bishydroxybiphenyl, tetramethoxymethyl-4,4'-bishydroxybiphenyl, a hexamethylol compound of TrisP-PA, a hexamethoxymethyl compound of TrisP-PA, phenol compounds in which 1 to 5 methylol groups of a hexamethylol compound of TrisP-PA are methoxymethylated, and bishydroxymethylnaphthalenediol.

Examples of the hydroxyanthracene compound include 1,6-dihydroxymethyl-2,7-dihydroxyanthracene.

Examples of the acyloxymethyl group-containing compound include compounds in which some or all of methylol groups of the above-mentioned methylol-containing compounds are acyloxymethylated.

Among these compounds, trimethylolphenol, bishydroxymethyl-p-cresol, tetramethylol bisphenol A, hexamethylol compounds of TrisP-PA (trade name; manufactured by Honshu Chemical Industry Co., Ltd.), and compounds in which the methylol groups of these compounds are substituted with alkoxymethyl groups or both of methylol and alkoxymethyl groups.

The compounds (c) may be used singly or in combination of two or more kinds thereof.

When cross-linking agent is contained in the colored curable composition, the content of the cross-linking agent varies depending on the material, and is preferably from 1% by weight to 70% by weight, more preferably from 5% by weight to 50% by weight, and still more preferably from 7% by weight to 30% by weight, with respect to the total solid content (weight) of the colored curable composition. When the content is within the above range, sufficient curing as well as excellent eluting properties at an unexposed area can be obtained, whereby insufficient curing at an exposed area and deterioration of eluting properties at the unexposed area can be prevented.

Polymerizable Monomer

The colored curable composition of the invention preferably contains at least one type of polymerizable monomer. The polymerizable monomer is suitably used when the colored curable composition of the invention is used as a negative-working composition.

The polymerizable monomer may be added to a positive-working colored curable composition containing a naphthoquinonediazide compound described below, together with a photopolymerization initiator described below. In this case, curing of a formed pattern can further be enhanced. Hereinafter, the polymerizable monomer will be described.

The polymerizable monomer is preferably a compound having at least one addition-polymerizable ethylenic unsaturated group, and having a boiling point of 100° C. or more under normal pressure. Examples thereof include: monofunctional acrylates and methacrylates, such as polyethylene glycol mono(meth)acrylate, polypropylene glycol mono(meth)acrylate, phenoxyethyl (meth)acrylate; polyethylene glycol di(meth)acrylate; trimethylolethane tri(meth)acrylate; neopentyl glycol di(meth)acrylate; pentaerythritol tri(meth)acrylate; pentaerythritol tetra(meth)acrylate; dipentaerythritol penta(meth)acrylate; dipentaerythritol hexa(meth)acrylate; hexanediol (meth)acrylate; trimethylolpropane tri(acryloyloxypropyl)ether; tri(acryloyloxyethyl)isocyanurate; compounds obtained by adding an ethylene oxide or a propylene oxide to a multifunctional alcohol such as glycerin or trimethylolethane, and then (meth)acrylating the resultant; urethane acrylates such as those described in JP-B Nos. 48-41708 and 50-6034 and JP-A No. 51-37193; polyester acrylates such as those described in JP-A No. 48-64183, JP-B Nos. 49-43191 and 52-30490; and multifunctional acrylates or methacrylates, such as epoxyacrylates obtained by the reaction of an epoxy resin and (meth)acrylic acid, and mixtures thereof.

Examples of polymerizable monomers further include light-curable monomers and oligomers described in "Journal of the Adhesion Society of Japan", Vol. 20, No. 7, pp. 300-308.

The content of the polymerizable monomer in the colored curable composition of the invention is preferably from 0.1% by mass to 90% by mass, more preferably from 1.0% by mass to 80% by mass, and still more preferably from 2.0% by mass to 70% by mass, with respect to the total solid content of the colored curable composition.

Radiation-Sensitive Compound

The colored curable composition of the invention preferably comprises at least one radiation-sensitive compound. The radiation-sensitive compound can cause chemical reactions such as the generation of radicals, acids or bases when irradiated with UV light with a wavelength of 400 nm or less, visible light, infrared light or an electron beam. When the colored curable composition of the invention contains the radiation-sensitive compound, it is possible to insolubilize the alkali-soluble binder by cross-linking, polymerization or decomposition of an acidic group, and to induce polymerization of the polymerizable monomer and oligomer or cross-linking of the residual cross-linking agent in a coating film, and thereby insolubilizing the coating film against an alkali developer.

When the colored curable composition of the invention is used as a negative-working composition, as the ultraviolet-sensitive compound, the colored curable composition preferably contains a photopolymerization initiator or a photoacid generator. When the colored curable composition of the invention is used as a positive-working composition, the colored curable composition preferably contains a naphthoquinonediazide compound.

Photopolymerization Initiator

The photopolymerization initiator used in the invention is not particularly limited, as long as it causes polymerization of the polymerizable monomer, and is preferably selected based on its properties, initiation efficiency, absorption wavelength, availability or cost. The photopolymerization initiator may be added to the positive-working composition containing a naphthoquinonediazide compound. In this case, curing of a formed pattern can further be enhanced.

Examples of the photopolymerization initiator include at least one activated halogen compound selected from a halomethyloxadiazole compound or a halomethyl-s-triazine compound; 3-aryl-substituted coumarin compounds; Rofin dimers; benzophenone compounds; acetophenone compounds and derivatives thereof; cyclopentadiene-benzene-iron complexes and salts thereof; and oxime compounds.

Examples of active halogen compounds such as halomethyloxadiazole compounds include 2-halomethyl-5-vinyl-1,3,4-oxadiazole compounds such as those described in JP-B No. 57-6096; 2-trichloromethyl-5-styryl-1,3,4-oxadiazole, 2-trichloromethyl-5-(p-cyanostyryl)-1,3,4-oxadiazole, and 2-trichloromethyl-5-(p-methoxy styryl)-1,3,4-oxadiazole.

Examples of halomethyl-s-triazine compounds include vinyl-halomethyl-s-triazine compounds such as those described in JP-B No. 59-1281, and 2-(naphtho-1-yl)-4,6-bis-halomethyl-s-triazine compounds and 4-(p-aminophenyl)-2,6-di-halomethyl-s-triazine compounds such as those described in JP-A No. 53-133428.

Other examples thereof include 2,4-bis(trichloromethyl)-6-p-methoxystyryl-s-triazine, 2,6-bis(trichloromethyl)-4-(3,4-methylenedioxyphenyl)-1,3,5-triazine, 2,6-bis(trichloromethyl)-4-(4-methoxyphenyl)-1,3,5-triazine, 2,4-bis(trichloromethyl)-6-(1-p-dimethylaminophenyl-1,3-butadienyl)-s-triazine, 2-trichloromethyl-4-amino-6-p-methoxystyryl-s-triazine, 2-(naphtho-1-yl)-4,6-bis(trichloromethyl)-s-triazine, 2-(4-methoxy-naphtho-1-yl)-4,6-bis(trichloromethyl)-s-triazine, 2-(4-ethoxy-naphtho-1-yl)-4,6-bis(trichloromethyl)-s-triazine, 2-(4-butoxy-naphtho-1-yl)-4,6-bis(trichloromethyl)-s-triazine, 2-[4-(2-methoxyethyl)-naphtho-1-yl]-4,6-bis(trichloromethyl)-s-triazine, 2-[4-(2-ethoxyethyl)-naphtho-1-yl]-4,6-bis(trichloromethyl)-s-triazine, 2-[4-(2-butoxyethyl)-naphtho-1-yl]-4,6-bis(trichloromethyl)-s-triazine, 2-(2-methoxy-naphtho-1-yl)-4,6-bis(trichloromethyl)-s-triazine, 2-(6-methoxy-5-methyl-naphtho-2-yl)-4,6-bis(trichloromethyl)-s-triazine, 2-(6-methoxy-naphtho-2-yl)-4,6-bis(trichloromethyl)-s-triazine, 2-(5-methoxy-naphtho-1-yl)-4,6-bis-trichloromethyl-s-triazine, 2-(4,7-dimethoxy-naphtho-1-yl)-4,6-bis(trichloromethyl)-s-triazine, 2-(6-ethoxy-naphtho-2-yl)-4,6-bis(trichloromethyl)-s-triazine, 2-(4,5-dimethoxy-naphtho-1-yl)-4,6-bis(trichloromethyl)-s-triazine, 4-[p-N,N-di(ethoxycarbonylmethyl)aminophenyl]-2,6-di(trichloromethyl)-s-triazine, 4-(o-methyl-p-N,N-di(ethoxycarbonylmethyl)aminophenyl)-2,6-bis(trichloromethyl)-s-triazine, 4-(p-N,N-di(chloroethyl)aminophenyl)-2,6-bis(trichloromethyl)-s-triazine, 4-[o-methyl-p-N,N-di(chloroethyl)aminophenyl]-2,6-bis(trichloromethyl)-s-triazine, 4-(p-N-chloroethylaminophenyl)-2,6-bis(trichloromethyl)-s-triazine, 4-(p-N-ethoxycarbonylmethylaminophenyl)-2,6-bis(trichloromethyl)-s-triazine, 4-[p-N,N-di(phenyl)aminophenyl]-2,6-bis(trichloromethyl)-s-triazine, 4-(p-N-chloroethylcarbonylaminophenyl)-2,6-bis(trichloromethyl)-s-triazine, 4-[p-N-(p-methoxyphenyl)carbonylaminophenyl]-2,6-bis(trichloromethyl)-s-triazine, 4-[m-N,N-di(ethoxycarbonylmethyl)aminophenyl]-2,6-bis(trichloromethyl)-s-triazine, 4-[m-bromo-p-N,N-di(ethoxycarbonylmethyl)aminophenyl]-2,6-bis(trichloromethyl)-s-triazine, 4-[m-chloro-p-N,N-di(ethoxycarbonylmethyl)aminophenyl]-2,6-bis(trichloromethyl)-s-triazine, 4-[m-fluoro-p-N,N-di(ethoxycarbonylmethyl)aminophenyl]-2,6-bis (trichloromethyl)-s-triazine, 4-[o-bromo-p-N,N-di(ethoxycarbonylmethyl)aminophenyl]-2,6-bis(trichloromethyl)-s-triazine, 4-[o-chloro-p-N,N-di(ethoxycarbonylmethyl)aminophenyl]-2,6-bis(trichloromethyl)-s-triazine, 4-[o-fluoro-p-N,N-di(ethoxycarbonylmethyl)aminophenyl]-2,6-bis(trichloromethyl)-s-triazine, 4-[o-bromo-p-N,N-di(chloroethyl)aminophenyl]-2,6-bis(trichloromethyl)-s-triazine, 4-[o-chloro-p-N,N-di(chloroethyl)aminophenyl]-2,6-bis(trichloromethyl)-s-triazine, 4-[o-fluoro-p-N,N-di(chloroethyl)aminophenyl]-2,6-bis(trichloromethyl)-s-triazine, 4-[m-bromo-p-N,N-di(chloroethyl)aminophenyl]-2,6-bis(trichloromethyl)-s-triazine, 4-[m-chloro-p-N,N-di(chloroethyl)aminophenyl]-2,6-bis(trichloromethyl)-s-triazine, 4-[m-fluoro-p-N,N-di(chloroethyl)aminophenyl]-2,6-bis(trichloromethyl)-s-triazine, 4-(m-bromo-p-N-ethoxycarbonylmethylaminophenyl)-2,6-bis(trichloromethyl)-s-triazine, 4-(m-chloro-p-N-ethoxycarbonylmethylaminophenyl)-2,6-bis(trichloromethyl)-s-triazine, 4-(m-fluoro-p-N-ethoxycarbonylmethylaminophenyl)-2,6-bis(trichloromethyl)-s-triazine, 4-(o-bromo-p-N-ethoxycarbonylmethylaminophenyl)-2,6-bis(trichloromethyl)-s-triazine, 4-(o-chloro-p-N-ethoxycarbonylmethylaminophenyl)-2,6-bis(trichloromethyl)-s-triazine, 4-(o-fluoro-p-N-ethoxycarbonylmethylaminophenyl)-2,6-bis(trichloromethyl)-s-triazine, 4-(m-bromo-p-N-chloroethylaminophenyl)-2,6-bis(trichloromethyl)-s-triazine, 4-(m-chloro-p-N-chloroethylaminophenyl)-2,6-bis(trichloromethyl)-s-triazine, 4-(m-fluoro-p-N-chloroethylaminophenyl)-2,6-bis(trichloromethyl)-s-triazine, 4-(o-bromo-p-N-chloroethylaminophenyl)-2,6-bis(trichloromethyl)-s-triazine, 4-(o-chloro-p-N-chloroethylaminophenyl)-2,6-bis(trichloromethyl)-s-triazine, and 4-(o-fluoro-p-N-chloroethylaminophenyl)-2,6-bis(trichloromethyl)-s-triazine.

Other useful examples thereof include TAZ series products (e.g., TAZ-107, TAZ-110, TAZ-104, TAZ-109, TAZ-140, TAZ-204, TAZ-113, TAZ-123.) manufactured by Midori Kagaku Co., Ltd.; T series products (e.g., T-OMS, T-BMP, T-R, T-B.) manufactured by PANCHIM; IRGACURE series products (e.g., IRGACURE 369, IRGACURE 784, IRGACURE 651, IRGACURE 184, IRGACURE 500, IRGACURE 1000, IRGACURE 149, IRGACURE 819, IRGACURE 261); DAROCUR series products, such as DAROCUR 1173, manufactured by Ciba Specialty Chemicals;

4,4'-bis(diethylamino)-benzophenone, 2-(O-benzoyloxime)-1-[4-(phenylthio)phenyl]-1,2-octandione, 1-(O-acetyloxime)-1-[9-ethyl-6-(2-methylbenzoyl)-9H-carbazol-3-yl]ethane, 2-benzyl-2-dimethylamino-4-morpholinobutyrophenone, 2,2-dimethoxy-2-phenylacetophenone, 2-(o-chlorophenyl)-4,5-diphenylimidazolyl dimer, 2-(o-fluorophenyl)-4,5-diphenylimidazolyl dimer, 2-(o-methoxyphenyl)-4,5-diphenylimidazolyl dimer, 2-(p-methoxyphenyl)-4,5-diphenylimidazolyl dimer, 2-(p-dimethoxyphenyl)-4,5-diphenylimidazolyl dimer, 2-(2,4-dimethoxyphenyl)-4,5-diphenylimidazolyl dimer, 2-(p-methyl mercaptophenyl)-4,5-diphenylimidazolyl dimer, and benzoin isopropyl ether.

The photopolymerization initiator is preferably oxime-O-acyl compounds such as 2-(O-benzoyloxime)-1-[4-(phenylthio)phenyl]-1,2-octandione and 1-(O-acetyloxime)-1-[9-ethyl-6-(2-methylbenzoyl)-9H-carbazol-3-yl]ethanone.

In addition to the photopolymerization initiators described above, the photosensitive colored curable composition according to the invention may contain other known photopolymerization initiators.

Specific examples thereof include vicinal polyketaldonyl compounds such as those described in U.S. Pat. No. 2,367,660; α-carbonyl compounds such as those described in U.S. Pat. Nos. 2,367,661 and 2,367,670; acyloin ethers such as those described in U.S. Pat. No. 2,448,828; aromatic acyloin compounds substituted with α-hydrocarbon such as those described in U.S. Pat. No. 2,722,512; polynuclear quinone compounds such as those described in U.S. Pat. Nos. 3,046,127 and 2,951,758; the combination of triarylimidazolyl dimer and p-aminophenyl ketone described in U.S. Pat. No. 3,549,367; and benzothiazole compounds and trihalomethyl-s-triazine compounds such as those described in JP-B No. 51-48516.

The content of the photopolymerization initiator in the colored curable composition of the invention is preferably from 0.01% by mass to 50% by mass, more preferably from 1% by mass to 30% by mass, and still more preferably from 1% by mass to 20% by mass, with respect to the solid content of the polymerizable monomer. When the content of the photopolymerization initiator is within the above range, polymerization reaction proceeds well and a film with favorable film strength can be obtained.

The photopolymerization initiator may be used in combination with a sensitizer or a photostabilizer.

Examples thereof include benzoin, benzoin methyl ether, 9-fluorenone, 2-chloro-9-fluorenone, 2-methyl-9-fluorenone, 9-anthrone, 2-bromo-9-anthrone, 2-ethyl-9-anthrone, 9,10-anthraquinone, 2-ethyl-9,10-anthraquinone, 2-t-butyl-9,10-anthraquinone, 2,6-dichloro-9,10-anthraquinone, xanthone, 2-methylxanthone, 2-methoxyxanthone, 2-ethoxyxanthone, thioxanthone, 2,4-diethylthioxanthone, acridone, 10-butyl-2-chloroacridone, benzil, dibenzalacetone, p-(dimethylamino)phenyl styryl ketone, p-(dimethylamino)phenyl-p-methyl styryl ketone, benzophenone, p-(dimethylamino)benzophenone (or Michler's ketone), p-(diethylamino)benzophenone, benzanthrone, benzothiazole compounds such as those described in JP-B No. 51-48516, and TINUVIN 1130 and TINUVIN 400 (trade name, manufactured by Chiba Specialty Chemicals).

The colored curable composition of the invention may contain a heat-polymerization inhibitor in addition to the above components. Examples of the heat-polymerization inhibitor include hydroquinone, p-methoxyphenol, di-t-butyl-p-cresol, pyrogallol, t-butylcatechol, benzoquinone, 4,4'-thiobis(3-methyl-6-t-butylphenol), 2,2'-methylene bis(4-methyl-6-t-butylphenol), and 2-mercaptobenzimidazole.

Photoacid Generator

Photoacid generator used in the invention is not limited, as long as it can decompose to generate an acid by irradiation of active light or radiation and can polymerize monomers having polymerization properties (polymerizable monomer). Examples thereof include known photoacid generators.

Examples of the photoacid generator include onium salts including diazonium salts such as those described in S. I. Schlesinger, Photogr. Sci. Eng., 18, 387 (1974), and T. S. Bal et al., Polymer, 21, 423 (1980), ammonium salts such as those described in U.S. Pat. Nos. 4,069,055 and 4,069,056 and JP-A No. 3-140140, phosphonium salts such as those described in D. C. Necker et al., Macromolecules, 17, 2468 (1984), C. S. Wen et al., Teh, Proc. Conf. Rad. Curing ASIA, p 478 Tokyo, October (1988) and U.S. Pat. Nos. 4,069,055 and 4,069,056., iodonium salts such as those described in J. V. Crivello et al., Macromorecules, 10 (6), 1307 (1977), Chem. & Eng. News, November 28, p 31 (1988), European Patent (EP) No. 104,143, U.S. Pat. Nos. 339,049 and 410,201 and JP-A Nos. 2-150848 and 2-296514, sulfonium salts such as those described in J. V. Crivello et al., Polymer J. 17, 73 (1985), J. V. Crivello et al., J. Org. Chem., 43, 3055 (1978), W. R. Watt et al., J. Polymer Sci., Polymer Chem. Ed., 22, 1789 (1984), J. V. Crivello et al., Polymer Bull., 14, 279 (1985), J. V. Crivello et al., Macromorecules, 14 (5), 1141 (1981), J. V. Crivello et al., J. Polymer Sci., Polymer Chem. Ed., 17, 2877 (1979), U.S. Pat. Nos. 3,902,114, 4,933,377, 410, 201, 339, 049, 4,760,013, 4,734,444, and 2,833,827, EP Nos. 370,693, 233,567, 297,443, and 297,442, and German Patent (DE) Nos. 2,904,626, 3,604,580, and 3,604,581, selenonium salts such as those described in J. V. Crivello et al., Macromorecules, 10 (6), 1307 (1977), J. V. Crivello et al., J. Polymer Sci., and Polymer Chem. Ed., 17, 1047 (1979), and arsonium salts such as those described in C. S. Wen et al., Teh, Proc. Conf. Rad. Curing ASIA, p 478 Tokyo, October (1988);

organic halogenated compounds such as those described in specifications of U.S. Pat. No. 3,905,815, JP-B No. 46-4605, and JP-A Nos. 48-36281, 55-32070, 60-239736, 61-169835, 61-169837, 62-58241, 62-212401, 63-70243, and 63-298339;

organic metal/organic halogenated compounds such as those described in K. Meier et al., J. Rad. Curing, 13 (4), 26 (1986), T. P. Gill et al., Inorg. Chem., 19, 3007 (1980), D. Astruc, Acc. Chem. Res., 19 (12), 377 (1896), and JP-A No. 2-161445;

photoacid generators having o-nitrobenzyl protecting groups such as those described in S. Hayase et al., J. Polymer Sci., 25, 753 (1987), E. Reichmanis et al., J. PholymerSci., Polymer Chem. Ed., 23, 1 (1985), Q. Q. Zhu et al., J. Photochem., 36, 85, 39, 317 (1987), B. Amit et al., Tetrahedron Lett., (24), 2205 (1973), D. H. R. Barton et al., J. Chem. Soc., 3571 (1965), P. M. Collins et al., J. Chem. SoC., Perkin I, 1695 (1975), M. Rudinstein et al., Tetrahedron Lett., (17), 1445 (1975), J. W. Walker et al., J. Am. Chem. Soc., 110, 7170 (1988), S. C. Busman et al., J. Imaging Technol., 11 (4), 191 (1985), H. M. Houlihan et al., Macromolecules, 21, 2001 (1988), P. M. Collins et al., J. Chem. Soc., Chem. Commun., 532 (1972), S. Hayase et al., Macromolecules, 18, 1799 (1985), E. Reichmanis et al., J. Electrochem. Soc., Solid State Sci. Technol., 130 (6), F. M. Houlihan et al., Macromolcules, 21, 2001 (1988), EP Nos. 0,290,750, 046,083, 156,535, 271, 851, and 0,388,343, U.S. Pat. Nos. 3,901,710 and 4,181,531 and JP-A Nos. 60-198538 and 53-133022;

compounds that can generate a sulfonic acid by photolysis such as iminosulfonates such as those described in M. TUNOOKA et al., Polymer Preprints Japan, 35 (8), G. Berner et al., J. Rad. Curing, 13 (4), W. J. Mijs et al., Coating Technol., 55 (697), 45 (1983), Akzo, H. Adachi et al., Polymer Preprints, Japan, 37 (3), EP Nos. 0,199,672, 84,515, 199,672, 044,115, and 0,101,122, U.S. Pat. Nos. 4,618,564, 4,371,605, and 4,431,774 and JP-A Nos. 64-18143, 2-245756, and 4-365048; and disulfone compounds such as those described in JP-A No. 61-166544.

Naphthoquinonediazide Compound

Next, the naphthoquinonediazide compound, which may be included in the colored curable composition of the invention when the composition is used as a positive-working composition, will be described.

The naphthoquinonediazide compound is a compound having at least one o-quinonediazide group, and specific examples thereof include o-naphthoquinonediazide-5-sulfonic acid ester, o-naphthoquinonediazide-5-sulfonic acid amide, o-naphthoquinonediazide-4-sulfonic acid ester, and o-naphthoquinonediazide-4-sulfonic acid amide. These esters and amides can be produced by a known method, for example, using a phenol compound represented by Formula (1) described in JP-A Nos. 2-84650 and 3-49437.

When the colored curable composition of the invention is used as a positive-working composition, the colored curable composition may contain the alkali-soluble phenol resin and the crosslinking agent described above. The alkali-soluble phenol resin is preferably dissolved in an organic solvent at the amount of approximately 2% by mass to 50% by mass, and the crosslinking agent is preferably dissolved in the organic solvent at the amount of approximately 2% by mass to 30% by mass. The content of the naphthoquinonediazide compound is preferably approximately 2% by mass to 30% by mass, with respect to a solution containing the binder (the alkali-soluble phenol resin) and the crosslinking agent. The content of the colorant (including the specific metal complex compound-1) is preferably approximately 2% by mass to 50% by mass, with respect to a solution containing the binder (the alkali-soluble phenol resin) and the crosslinking agent.

Solvent

When the colored curable composition of the invention is prepared, a solvent is usually used.

The solvent that can be used in the invention is not particularly limited, as far as it satisfies the requirements for solubility of respective components in the colored curable composition and for coating properties of the colored curable composition. In particular, the solvent is preferably selected properly in consideration of solubility of the binder and coating properties and safety.

Preferable examples of the solvent include esters such as ethyl acetate, n-butyl acetate, isobutyl acetate, amyl formate, isoamyl acetate, isobutyl acetate, butyl propionate, isopropyl butyrate, ethyl butyrate, butyl butyrate, methyl lactate, ethyl lactate, methyl oxyacetate, ethyl oxyacetate, butyl oxyacetate (for example, methyl methoxyacetate, ethyl methoxyacetate, butyl methoxyacetate, methyl ethoxyacetate and ethyl ethoxyacetate), 3-oxypropionic acid alkyl esters such as methyl 3-oxypropionate and ethyl 3-oxypropionate (for example, methyl 3-methoxypropionate, ethyl 3-methoxypropionate, methyl 3-ethoxypropionate and ethyl 3-ethoxypropionate), 2-oxypropionic acid alkyl esters such as methyl 2-oxypropionate, ethyl 2-oxypropionate and propyl 2-oxypropionate (for example, methyl 2-methoxypropionate, ethyl 2-methoxypropionate, propyl 2-methoxypropionate, methyl 2-ethoxypropionate, ethyl 2-ethoxypropionate, methyl 2-oxy-2-methylpropionate, ethyl 2-oxy-2-methylpropionate, methyl 2-methoxy-2-methylpropionate and ethyl 2-ethoxy-2-methylpropionate), methyl pyruvate, ethyl pyruvate, propyl pyruvate, methyl acetoacetate, ethyl acetoacetate, methyl 2-oxobutanoate and ethyl 2-oxobutanoate;

ethers such as diethylene glycol dimethyl ether, tetrahydrofuran, ethylene glycol monomethyl ether, ethylene glycol monoethyl ether, methyl cellosolve acetate, ethyl cellosolve acetate, diethylene glycol monomethyl ether, diethylene glycol monoethyl ether, diethylene glycol monobutyl ether, propylene glycol methyl ether, ethyl carbitol acetate, butyl carbitol acetate, propylene glycol methyl ether acetate, propylene glycol ethyl ether acetate and propylene glycol propyl ether acetate;

ketones such as methyl ethyl ketone, cyclohexanone, 2-heptanone and 3-heptanone; and aromatic hydrocarbons such as toluene and xylene.

Among these, methyl 3-ethoxypropionate, ethyl 3-ethoxypropionate, ethyl cellosolve acetate, ethyl lactate, diethylene glycol dimethyl ether, n-butyl acetate, methyl 3-methoxypropionate, 2-heptanone, cyclohexanone, ethyl carbitol acetate, butyl carbitol acetate, propylene glycol methyl ether and propylene glycol methyl ether acetate are more preferable.

Additives

The colored curable composition of the invention may contain various additives such as filler, a high-molecular compound other than those described above, a surfactant, an adhesion accelerator, an antioxidant, an ultraviolet absorber and an aggregation inhibitor, if necessary.

Specific examples of the various additives include fillers such as glass and alumina; high-molecular compounds other than the binder resin, such as polyvinylalcohol, polyacrylic acid, polyethylene glycol monoalkyl ethers, and polyfluoroalkyl acrylates; nonionic, cationic and anionic surfactants; adhesion accelerators such as vinyltrimethoxysilane, vinyltriethoxysilane, vinyltris(2-methoxyethoxy)silane, N-(2-aminoethyl)-3-aminopropylmethyldimethoxysilane, N-(2-aminoethyl)-3-aminopropyltrimethoxysilane, 3-aminopropyltriethoxysilane, 3-glycidoxypropyltrimethoxysilane, 3-glycidoxypropylmethyldimethoxysilane, 2-(3,4-epoxycyclohexyl)ethyltrimethoxysilane, 3-chloropropylmethyldimethoxysilane, 3-chloropropyltrimethoxysilane, 3-methacryloxypropyltrimethoxysilane, and 3-mercaptopropyltrimethoxysilane; antioxidants such as 2,2-thiobis(4-methyl-6-t-butylphenol) and 2,6-di-t-butylphenol; ultraviolet absorbers such as 2-(3-t-butyl-5-methyl-2-hydroxyphenyl)-5-chlorobenzotriazole and alkoxybenzophenones; and aggregation inhibitors such as sodium polyacrylate.

An organic carboxylic acid, preferably a low-molecular organic carboxylic acid having a molecular weight of 1,000 or less, may be added to the colored curable composition of the invention, in order to enhance the alkaline solubility of an area to be removed by development (e.g., an uncured area in the case of a negative-working composition) and to further improve the developability of the colored curable composition of the invention.

Specific examples of the low-molecular organic carboxylic acid include aliphatic monocarboxylic acids such as formic acid, acetic acid, propionic acid, butyric acid, valeric acid, pivalic acid, caproic acid, diethylacetic acid, enanthic acid, and caprylic acid; aliphatic dicarboxylic acids such as oxalic acid, malonic acid, succinic acid, glutaric acid, adipic acid, pimelic acid, suberic acid, azelaic acid, sebacic acid, brassylic acid, methylmalonic acid, ethylmalonic acid, dimethylmalonic acid, methylsuccinic acid, tetramethylsuccinic acid and citraconic acid; aliphatic tricarboxylic acids such as tricarballylic acid, aconitic acid and camphoronic acid; aromatic monocarboxylic acids such as benzoic acid, toluic acid, cuminic acid, hemellitic acid and mesitylenic acid; aromatic polycarboxylic acids such as phthalic acid, isophthalic acid, terephthalic acid, trimellitic acid, trimesic acid, mellophanic acid and pyromellitic acid; and other carboxylic acids such as phenylacetic acid, hydratropic acid, hydrocinnamic acid, mandelic acid, phenylsuccinic acid, atropic acid, cinnamic acid, methyl cinnamate, benzyl cinnamate, cinnamylideneacetic acid, coumaric acid and umbellic acid.

The colored curable composition of the invention can be preferably used for forming color pixels of color filters used in liquid crystal displays (LCDs) or solid-state image sensors (e.g., CCD and CMOS), and for producing printing inks, inkjet inks, and coating agents. In particular, the colored curable composition of the invention can be preferably used for forming color pixels for solid-state image sensors, such as CCD and CMOS.

The colored curable composition of the invention is particularly preferable for the formation of a color filter for a solid-state image sensor which has a very small-sized coloring pattern, which is formed into a thin film, and which requires a favorable rectangular cross sectional profile. Specifically, because of the increased amount of coloring materials when the pixel pattern size (side length of the pixel pattern viewed from a normal direction to the substrate) constituting the color filter is 2 μm or less (for example, from 0.5 μm to 2.0 μm), and because of the blue-based color hue, line width sensitivity may be deteriorated and a DOF margin may become narrow, thereby impairing the pattern formation properties. This is remarkable when the pixel pattern size is from 1.0 μm to 1.7 μm (and more remarkable when the pixel pattern size is from 1.2 μm to 1.5 μm). In a thin film having a thickness of 1 μm or less, the amount of ingredients (other than coloring materials) that contribute to photolithographic properties in the film relatively decreases, and the amount of other ingredients further decreases due to an increase in the amount of coloring materials, thereby decreasing sensitivity and making the pattern more susceptible to removal from an area of low exposured. In this case, when heat treatment such as post-baking is performed, thermal sagging is likely to occur. These phenomena are remarkable when the film thickness is from 0.005 μm to 0.9 μm (more remarkable when the film thickness is from 0.1 μm to 0.7 μm).

Color Filter and Method for Producing the Color Filter

A color filter of the invention is obtained using the colored curable composition of the present invention containing the above described dipyrromethene metal complex compound or tautomers thereof. Hereinafter, the color filter of the invention will be described in detail through a production method therefor.

In a method for producing the color filter of the invention, the above described colored curable composition of the invention is used. The colored curable composition of the invention is preferably used as a composition which has been imparted with photosensitivity (more preferably ultraviolet sensitivity). The color filter of the invention is produced, for example, by a process (hereinafter referred to as an "image forming process") including applying the colored curable composition of the invention having photosensitivity to a substrate by using an application method such as a spin coating method, a cast coating method, or a roll coating method to form a photosensitive coating layer; exposing the formed coating layer to light (for example, through a given pattern mask); and developing the resultant with a developer to form a pattern image (resist pattern) of a negative type or a positive type.

The light source used for exposure is preferably a light source that emits light with a wavelength of 400 nm or less. The light source is not particularly limited, and, examples thereof include lamp light sources such as a xenon lamp, a halogen lamp, a tungsten lamp, a high-pressure mercury lamp, an ultrahigh-pressure mercury lamp, a metal halide lamp, a medium-pressure mercury lamp, a low-pressure mercury lamp, a carbon arc lamp and a fluorescent lamp, and laser light sources. When only a specific wavelength is used, an optical filter may also be used.

Examples of the laser light sources include Ar ion laser (364 nm, 351 nm, 10 mW to 1 W), Kr ion laser (356 nm, 351 nm, 10 mW to 1 W), solid state lasers such as a combination of a waveguide-type frequency conversion device with an AlGaAs semiconductor, or a combination of a waveguide-type frequency conversion device with an AlGaInP/AlGaAs semiconductor (300 nm to 350 nm, 5 mW to 100 mW), and other pulsed lasers such as $N_2$ laser (337 nm, pulse: 0.1 mJ to 10 mJ) and XeF (351 nm, pulse: 10 mJ to 250 mJ). Ultraviolet rays such as an ArF excimer laser (wavelength: 193 nm), a KrF excimer laser (wavelength: 248 nm) or an i-line ray (wavelength: 365 nm) may be used. In consideration of cost and exposure energy, the light source is more preferably ultraviolet rays, and examples thereof include g-line ray, h-line ray and i-line ray. Among these, i-line ray is preferable.

Exposure of the colored curable composition of the invention may be conducted by any of a proximity method, a mirror projection method, or a stepper method. It is preferable to conduct exposure by the stepper method (a reduction-projection exposure method using a reduction-projection exposure apparatus). In the stepper method, patterns are formed by conducting exposure while changing the exposure amount step by step. The rectangularity of patterns can be improved by conducting exposure by the stepper method.

Examples of an exposure apparatus used for the stepper exposure include an i-line stepper (trade name: FPA-3000i5+, manufactured by Canon Inc.).

Thereafter, as a curing process, the formed colored pattern may be subjected to post-heating and/or post-exposing to further cure the pattern, if necessary. The light or radiation ray used in the curing process is preferably a radiation ray such as an i-line ray.

In the production process of a color filter, when producing a negative-working color filter, the image forming process (and the curing process, as needed) is repeated in accordance with the number of colors as desired, so that a color filter with desired number of color hues can be produced. When producing a positive-working color filter, the image forming process and the curing process are repeated in accordance with the number of colors as desired, so that a color filter with desired number of color hues can be produced.

Examples of the substrate include soda glass, PYREX (registered trademark) glass and quartz glass, and substrates each obtained by attaching a transparent conductive film to any of these materials, which are used in a liquid crystal display element and the like; photoelectric conversion element substrates that are used in image sensors, such as a silicone substrate; and a complementary metal-oxide semiconductor (CMOS). These substrates may have black stripes that separate the respective pixels.

Furthermore, on these substrates, an undercoat layer may be provided, if necessary, for the purpose of improving the adhesion with upper layers, preventing material diffusion, or flattening the substrate surface.

As the developer, any developer may be used, as long as the developer dissolves an area to be developed (an uncured area in the case of a negative-working composition) and does not dissolve other area (a cured area in the case of a negative-working composition) of the colored curable composition of the invention. Specifically, various combinations of organic solvents or aqueous alkaline solutions may be used. Examples of the organic solvents include solvents that can be used when the colored curable composition of the invention is prepared, which will be described above.

The aqueous alkaline solution is preferably an aqueous alkaline solution obtained by dissolving an alkaline compound in pure water to have a concentration of from 0.001% by mass to 10% by mass, more preferably from 0.01% by mass to 1% by mass. Examples of the alkaline compound include sodium hydroxide, potassium hydroxide, sodium carbonate, sodium silicate, sodium metasilicate, aqueous ammonia, ethylamine, diethylamine, dimethylethanolamine, tetramethylammonium hydroxide, tetraethylammonium hydroxide, choline, pyrrole, piperidine, and 1,8-diazabicyclo-[5.4.0]-7-undecene.

When such an aqueous alkaline solution is used as a developer, washing with water is usually performed after the development.

The color filter of the invention can be used in liquid crystal display elements and solid-state image sensors such as a charge coupled device (CCD), and preferably in a high-definition charge coupled device (CCD) or CMOS device having 1,000,000 pixels or more. Furthermore, the color filter of the invention may be used, for example, as a color filter arranged between a light condensing micro lens and a light-receiving unit of each pixel in a charge coupled device (CCD).

EXAMPLES

Hereafter, the invention will be explained in more detail with reference to examples, but the invention is not limited to the examples unless departing from the gist of the invention. Further, the "part" indicates quantities in terms of mass, unless otherwise specified.

Example 1

Synthesis Example 1

Synthesis of Dipyrromethene Metal Complex Compound

As a dipyrromethene metal complex compound, the exemplary compounds Ia-15, Ib-15, IIa-6 and IIb-6 were synthesized according to the following reaction scheme 1.

Reaction scheme 1

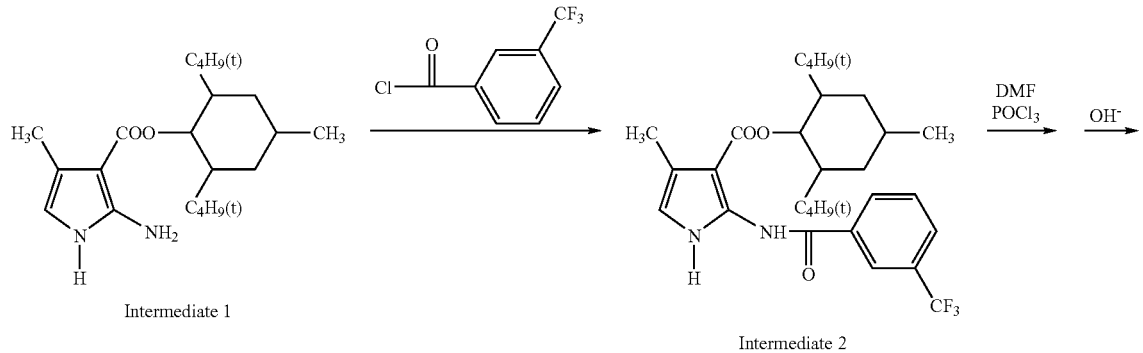

Intermediate 1

Intermediate 2

-continued
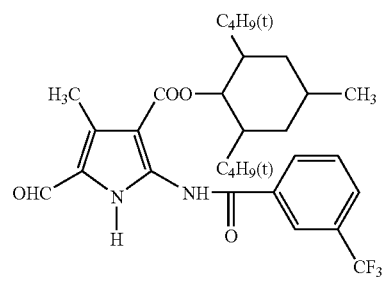
Intermediate 3
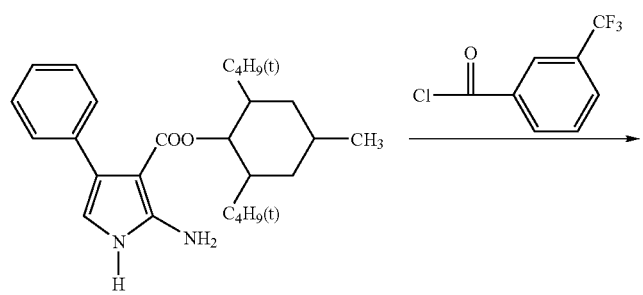
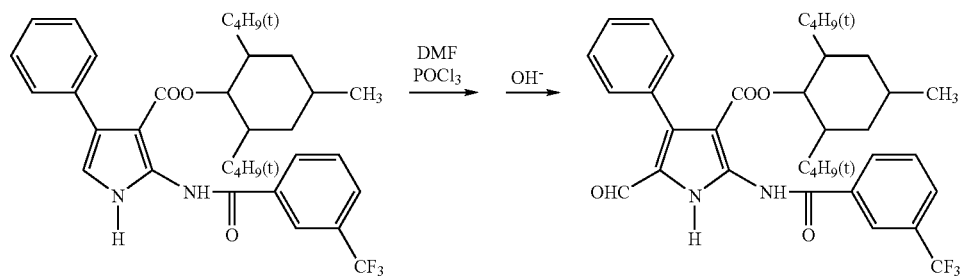
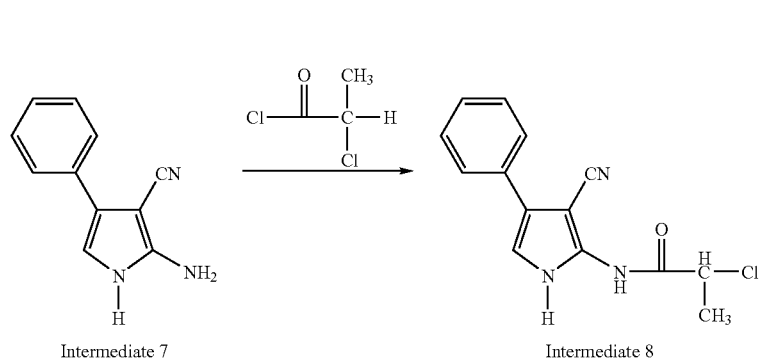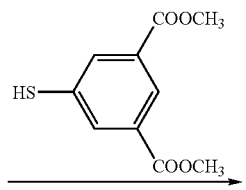
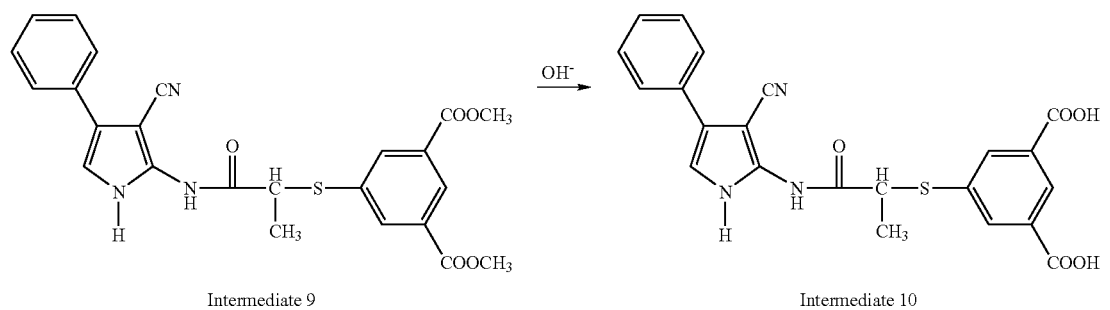

-continued
Intermediate 3 + Intermediate 10 →
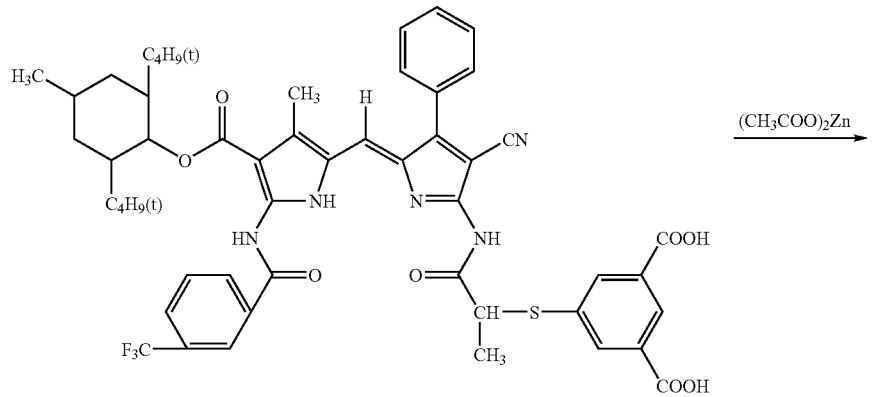
Intermediate 11
(CH₃COO)₂Zn →
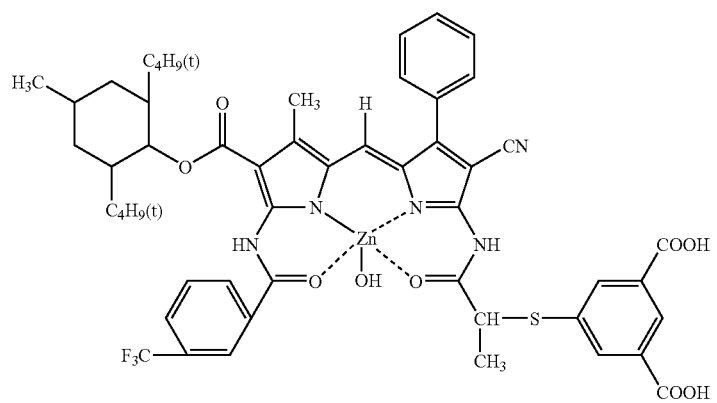
Exemplary compound Ia-15
Intermediate 6 + Intermediate 10 →
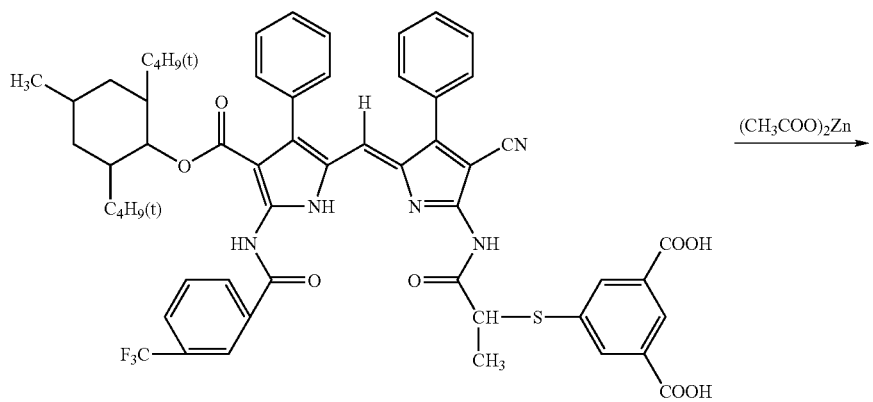
Intermediate 12
(CH₃COO)₂Zn →

-continued
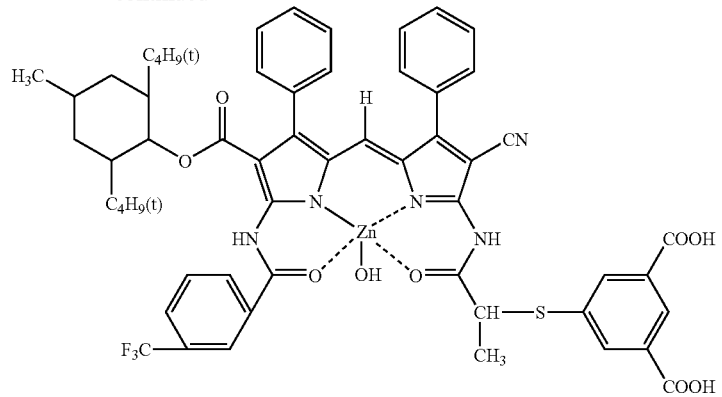
Exemplary compound Ib-15
Intermediate 2 $\xrightarrow{\text{CH(OC}_2\text{H}_5)_3}$
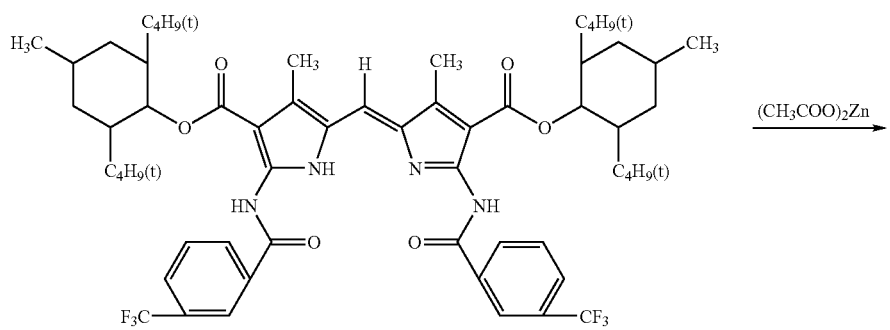
Intermediate 13 $\xrightarrow{(\text{CH}_3\text{COO})_2\text{Zn}}$
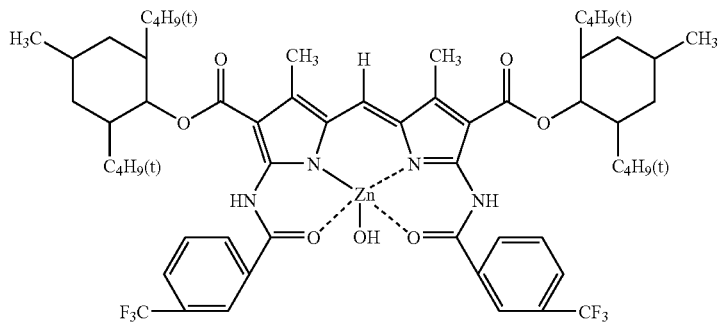
Exemplary Compound IIa-6
Intermediate 5 $\xrightarrow{\text{CH(OC}_2\text{H}_5)_3}$
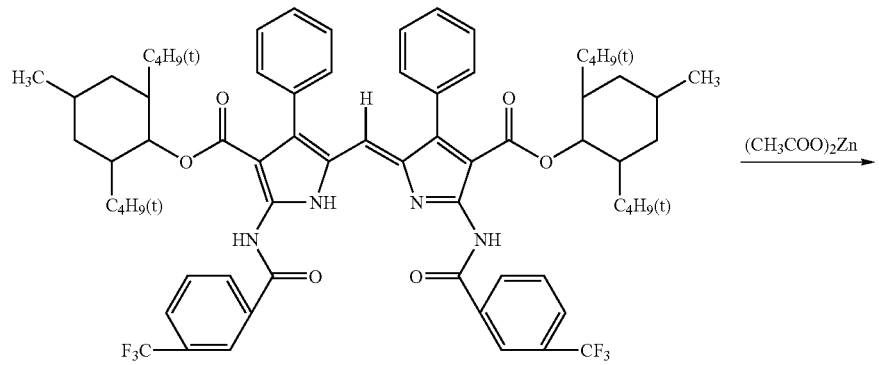
Intermediate 14 $\xrightarrow{(\text{CH}_3\text{COO})_2\text{Zn}}$

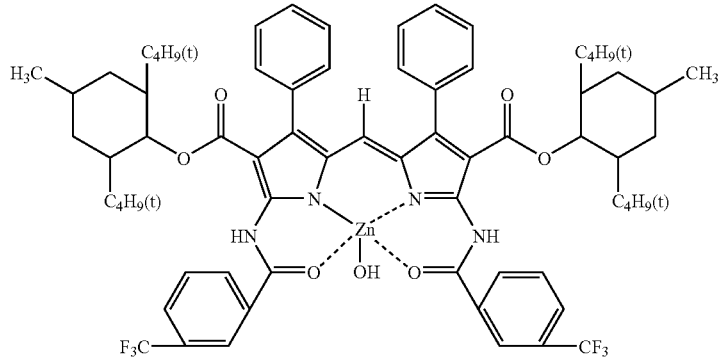

Exemplary Compound IIb-6

First, as shown in the reaction scheme 1, intermediates 1, 4, and 7 were synthesized according to a method described in the specification of U.S. Patent Application Publication No. 2008/0076044. Subsequently, as described below, intermediates 2, 3, 5, 6, and 8 to 14 were synthesized, and then the exemplary compounds Ia-15, Ib-15, IIa-6, and IIb-6 were synthesized.

Synthesis of Intermediate 2

45 ml of acetonitrile was added to 15.2 g (0.436 mol) of the intermediate 1 obtained according to the method described in the specification of U.S. patent Application Publication No. 2008/0076044, and the mixture was stirred under cooling with ice. To the mixed solution, 10 g (0.479 mol) of 3-(trifluoromethyl)benzoyl chloride was added dropwise. Thereafter, to the mixture, 4.13 g (0.523 mol) of pyridine was added dropwise, and the resultant mixture was stirred at room temperature for 1.5 hours. The reaction liquid was poured into 500 ml of an aqueous hydrochloric acid solution. Subsequently, the mixture was extracted with 300 ml of ethyl acetate, and then neutralized with 500 ml of an aqueous saturated sodium hydrogen carbonate solution. The resultant was dried over magnesium sulfate, and filtered, and then the filtrate was concentrated under reduced pressure. Thereafter, the resultant was purified by column chromatography, and the obtained solid was washed with methanol. Then, the solid was filtered off and dried, whereby 11.4 g (yield: 50.2%) of an intermediate 2 was obtained.

Details of $^1$H-NMR (CDCl$_3$) were as follows: δ=11.3 (br, 1H); 10.5 (br, 1H); 8.34 (s, 1H); 8.25-8.23 (d, 1H); 7.93-7.0 (d, 1H); 7.77-7.72 (t, 1H); 6.26-6.22 (d, 1H); 6.02-6.0 (br, 1H); 2.27 (s, 3H); 1.69-1.43 (br, 3H); 1.44-1.20 (br, 4H); 1.06-1.03 (d, 3H); and 0.91 (s, 18H).

Synthesis of Intermediate 3

10 ml of dimethylformamide was stirred while cooling with ice (5° C.). To the liquid, 0.98 g (6.4 mmol) of phosphorus oxychloride was added dropwise. After the dropwise addition was completed, the resultant was stirred at 5° C. for 30 minutes, and then 2.55 g (4.9 mmol) of the intermediate 2 obtained as described above was added thereto. Thereafter, the mixture was stirred at 5° C. to 10° C. for 1 hour to complete the reaction. After the reaction was completed, the reaction liquid was added dropwise to 250 ml of water while stirring. To the solution, an aqueous solution in which 0.77 g of sodium hydroxide was dissolved in 10 ml of water was added dropwise while stirring, and the mixture was stirred at room temperature for 30 minutes. The precipitated crystal was filtered, and washed with 30 ml of water. Thereafter, the crystal was dispersed and washed with 200 ml of methanol. Then, the crystal was filtered, washed with 15 ml of methanol and dried, whereby 2.2 g (yield: 83.0%) of an intermediate 3 was obtained.

Details of $^1$H-NMR (CDCl$_3$) were as follows: δ=12.1-11.9 (br, 1H); 11.0-10.8 (br, 1H); 8.99 (s, 1H); 8.64 (s, 1H); 8.35-8.33 (d, 1H); 8.1-8.08 (d, 1H); 7.87-7.83 (t, 1H); 6.0-5.9 (br, 1H); 2.26 (s, 3H); 1.72-1.4 (br, 3H); 1.46-1.41 (br, 4H); 1.04-1.03 (d, 3H); and 0.93 (s, 18H).

Synthesis of Intermediate 5

100 ml of acetonitrile was added to 32.8 g (79.9 mmol) of the intermediate 4 obtained according to the method described in the specification of U.S. Patent Application Publication No. 2008/0076044, and the mixture was stirred at room temperature. To the solution, 20 g (95.9 mmol) of 3-(trifluoromethyl)benzoyl chloride was added dropwise, and the mixture was stirred at room temperature for 1 hour. The obtained crystal was filtered, washed with acetonitrile and dried, whereby 27 g (yield: 58%) of an intermediate 5 was obtained.

Details of $^1$H-NMR (CDCl$_3$) were as follows: δ=11.45 (br, 1H); 10.52 (br, 1H); 8.56 (s, 1H); 8.32-8.3 (d, 1H); 7.85-7.82 (d, 1H); 7.77-7.74 (t, 1H); 7.42-7.35 (m, 5H); 6.22-6.2 (d, 1H); 5.9 (br, 1H); 1.28-1.26 (d, 2H); 1.08-1.06 (d, 2H); 0.82 (s, 18H); 0.75 (d, 3H); and 0.6-0.52 (m, 1H).

Synthesis of Intermediate 6

60 ml of dimethylformamide was stirred while cooling with ice (5° C.). To the liquid, 9.24 g (60.2 mmol) of phosphorus oxychloride was added dropwise. After the dropwise addition was completed, the resultant was stirred at 5° C. for 30 minutes, and then 27 g (46.3 mmol) of the intermediate 5 obtained as described above was added thereto. Thereafter, the mixture was stirred at 5° C. to 10° C. for 1 hour to complete the reaction. After the reaction was completed, the reaction liquid was added dropwise to 1.2 L of water while stirring. To the solution, an aqueous solution in which 7.23 g of sodium hydroxide was dissolved in 100 ml of water was added dropwise while stirring, and the mixture was stirred at room temperature for 30 minutes. The precipitated crystal was filtered, and washed with 50 ml of water. Thereafter, the crystal was dispersed and washed with 600 ml of methanol. Then, the crystal was filtered, washed with 20 ml of methanol and dried, whereby 13.8 g (yield: 48.7%) of an intermediate 6 was obtained.

Details of $^1$H-NMR (CDCl$_3$) were as follows: δ=11.91-11.86 (br, 1H); 11.44-11.34 (br, 1H); 9.06 (s, 1H); 8.33 (s, 1H); 8.16-8.12 (d, 1H); 7.93-7.87 (d, 1H); 7.77-7.72 (t, 1H); 7.48-7.41 (m, 3H); 7.39-7.33 (m, 2H); 5.96-5.94 (br, 1H); 1.28-1.26 (d, 2H); 1.06-1.04 (d, 2H); 0.84 (s, 18H); 0.73-0.71 (d, 3H); and 0.57-0.48 (m, 1H).

Synthesis of Intermediate 8

90 ml of dimethylacetamide was added to 30 g (164 mmol) of the intermediate 7 obtained according to the method described in the specification of U.S. Patent Application Publication No. 2008/0076044, and the mixture was stirred at room temperature. To the solution, 24.9 g (197 mmol) of 2-chloropivaloyl chloride was added dropwise, and the mixture was stirred at room temperature for 1 hour. The obtained crystal was filtered, washed with acetonitrile and dried, whereby 40.1 g (yield: 89.7%) of an intermediate 8 was obtained.

Details of $^1$H-NMR (DMSO-d$_6$) were as follows: δ=12.09-12.03 (br, 1H); 11.11 (s, 1H); 7.64-7.62 (d, 2H); 7.42-7.37 (t, 2H); 7.28-7.2 (t, 1H); 7.02 (s, 1H); 4.9-4.82 (q, 1H); and 1.66-1.63 (d, 3H).

Synthesis of Intermediate 9

6.97 g (25.5 mmol) of the intermediate 8 obtained as described above and 5.76 g (25.5 mmol) of 5-mercapto isophthalic acid dimethyl ester were dissolved in 20 ml of dimethylacetamide. To the mixture, 2.7 g (26.7 mmol) of triethylamine was added dropwise while stirring at room temperature. Thereafter, the mixture was stirred at room temperature for 1 hour and further stirred at 50° C. for 1 hour. After the reaction was completed, the reaction liquid was added dropwise to 500 ml of an aqueous hydrochloric acid solution. Then, the mixture was extracted with 250 ml of ethyl acetate. The extract was dried over magnesium sulfate, and then filtered. The solvent of the filtrate was distilled off under reduced pressure. Thereafter, the resultant was dispersed and washed with 100 ml of methanol. Then, the crystal was filtered, washed with 10 ml of methanol and dried, whereby 11.16 g (yield: 94.6%) of an intermediate 9 was obtained.

Details of $^1$H-NMR (DMSO-d$_6$) were as follows: δ=11.96-11.92 (br, 1H); 10.92-10.9 (br, 1H); 8.37 (s, 1H); 8.22 (s, 2H); 7.62-7.59 (d, 2H); 7.43-7.37 (t, 2H); 7.3-7.24 (t, 1H); 6.95 (s, 1H); 4.41-4.33 (q, 1H); 3.89 (s, 6H); and 1.48-1.44 (d, 3H).

Synthesis of Intermediate 10

11.1 g (23.9 mmol) of the intermediate 9 obtained by the above-described method was dissolved in 55 ml of N-methylpyrrolidone. To the resultant liquid, an aqueous solution in which 2.87 g (71.7 mmol) of sodium hydroxide was dissolved in 20 ml of water was added dropwise while stirring at 40° C., and then stirred while heating at 40° C. for 2.5 hours. The extract was dried over magnesium sulfate, and then filtered. The solvent of the filtrate was distilled off under reduced pressure. Thereafter, the reaction liquid was poured into 500 ml of an aqueous hydrochloric acid solution. Then, the mixture was extracted with 200 ml of ethyl acetate. The extract was dried over magnesium sulfate, and filtered. Then, the solvent of the filtrate was distilled off under reduced pressure. The residue was dispersed and washed with 100 ml of methanol. The crystal was filtered, washed with 10 ml of methanol and dried, whereby 9.5 g (yield: 91.3%) of an intermediate 10 was obtained.

Details of $^1$H-NMR (DMSO-d$_6$) were as follows: δ=11.96-11.91 (br, 1H); 10.99 (s, 1H); 8.36 (s, 1H); 8.2 (d, 2H); 7.62-7.58 (d, 2H); 7.43-7.35 (t, 2H); 7.31-7.22 (t, 1H); 6.95 (s, 1H); 4.42-4.33 (q, 1H); and 1.5-1.44 (d, 3H).

Synthesis of Intermediate 11

5.04 g (9.19 mmol) of the intermediate 3 obtained as described above was dispersed in a mixed solution of 10 ml of acetic anhydride and 10 ml of difluoroacetic acid. To the resultant, 5.61 g (9.19 mmol) of the intermediate 10 obtained above was added while stirring at room temperature. The mixture was stirred at room temperature for 1 hour. Thereafter, the reaction mixture was added dropwise to 500 ml of an aqueous saturated sodium hydrogen carbonate solution. Then, the mixture was extracted with 250 ml of ethyl acetate. The extract was dried over sodium sulfate, and filtered. The solvent of the filtrate was distilled off under reduced pressure. Thereafter, the resultant was dispersed and washed with 60 ml of ethyl acetate. The crystal was filtered, washed with 10 ml of ethyl acetate and dried, whereby 3.01 g (yield: 33.9%) of an intermediate 11 was obtained.

Detail of $^1$H-NMR (DMSO-d$_6$) were as follows: δ=11.9-11.87 (br, 1H); 10.92 (s, 2H); 8.36 (s, 1H); 8.28-8.26 (d, 2H); 8.18-8.11 (br, 2H); 8.04-8 (d, 1H); 7.88 (s, 1H); 7.5-7.36 (m, 5H); 6.49 (br, 1H); 6 (s, 1H); 4.51-4.42 (q, 1H); 1.33-1.15 (m, 3H); 1.15-1.07 (m, 2H); 0.93 (s, 9H); 0.84 (s, 9H); 0.73-0.69 (d, 3H); and 0.61-0.49 (m, 1H).

Synthesis of Intermediate 12

5.61 g (9.19 mmol) of the intermediate 6 obtained as described above was dispersed in a mixed solution of 10 ml of acetic anhydride and 10 ml of difluoroacetic acid. To the resultant, 4 g (9.19 mmol) of the intermediate 10 obtained above was added while stirring at room temperature. The mixture was stirred at room temperature for 1 hour. Thereafter, the reaction mixture was added dropwise to 500 ml of an aqueous saturated sodium hydrogen carbonate solution. Then, the mixture was extracted with 250 ml of ethyl acetate. The extract was dried over sodium sulfate, and filtered. The solvent of the filtrate was distilled off under reduced pressure. Thereafter, the resultant was dispersed and washed with 60 ml of ethyl acetate. The crystal was filtered, washed with 10 ml of ethyl acetate and dried, whereby 3.97 g (yield: 42.1%) of an intermediate 12 was obtained.

Details of $^1$H-NMR (DMSO-d$_6$) were as follows: δ=11.96-11.91 (br, 1H); 10.99 (s, 2H); 8.38 (s, 1H); 8.28-8.22 (d, 2H); 8.2-8.12 (s, 2H); 8.06-8.02 (d, 1H); 7.88 (s, 1H); 7.51-7.32 (m, 10H); 6.49 (br, 1H); 6.04 (s, 1H); 4.42-4.33 (q, 1H); 1.32-1.15 (m, 3H); 1.13-1.04 (m, 2H); 0.9 (s, 9H); 0.8 (s, 9H); 0.72-0.68 (d, 3H); and 0.58-0.42 (m, 1H).

Synthesis of Intermediate 13

9.05 g (20 mmol) of the intermediate 2 obtained by the above-described method and 5.19 g (35 mmol) of an orthoformic acid trimethyl ester were dispersed in a mixed solution of 10 ml of acetic anhydride and 10 ml of difluoroacetic acid. The mixture was stirred at room temperature for 1 hour. Thereafter, the reaction mixture was added dropwise to 500 ml of an aqueous saturated sodium hydrogen carbonate solution. Then, the mixture was extracted with 250 ml of ethyl acetate. The extract was dried over magnesium sulfate, and filtered. The solvent of the filtrate was distilled off under reduced pressure. Thereafter, the resultant was purified by column chromatography, and dispersed and washed with 80 ml of methanol. The crystal was filtered, washed with 10 ml of methanol and dried, whereby 5.31 g (yield: 58%) of an intermediate 13 was obtained.

Details of $^1$H-NMR (CDCl$_3$) were as follows: δ=11.64 (br, 2H); 11.14-11.11 (br, 2H); 8.38 (s, 2H); 8.14-8.11 (d, 2H); 7.9-7.88 (d, 2H); 7.77-7.71 (t, 2H); 6.84 (s, 1H); 6.06 (br, 2H); 2.6 (s, 6H); 1.72-1.66 (br, 4H); 1.28-1.17 (br, 8H); 0.92 (s, 36H); and 0.73-0.66 (br, 2H).

Synthesis of Intermediate 14

10 g (17.2 mmol) of the intermediate 5 obtained by the above-described method and 5.19 g (30.1 mmol) of an orthoformic acid trimethyl ester were dispersed in a mixed solution of 10 ml of acetic anhydride and 10 ml of difluoroacetic acid. The mixture was stirred at room temperature for 1 hour. Thereafter, the reaction mixture was added dropwise to 500 ml of an aqueous saturated sodium hydrogen carbonate solution. Then, the mixture was extracted with 250 ml of ethyl acetate. The extract was dried over magnesium sulfate, and filtered. The solvent of the filtrate was distilled off under reduced pressure. Thereafter, the resultant was purified by column chromatography, and dispersed and washed with 80 ml of methanol. The crystal was filtered, washed with 10 ml of methanol and dried, whereby 4.3 g (yield: 42.6%) of an intermediate 14 was obtained.

Details of $^1$H-NMR (CDCl$_3$) were as follows: δ=11.61-11.58 (br, 2H); 11.12-11.09 (br, 2H); 8.37 (s, 2H); 8.12-8.1 (d, 2H); 7.89-7.86 (d, 2H); 7.77-7.71 (t, 2H); 7.33-7.14 (10H); 6.88 (s, 1H); 6.04 (br, 2H); 1.72-1.66 (br, 4H); 1.28-1.17 (br, 8H); 0.92 (s, 36H); and 0.73-0.66 (br, 2H).

Synthesis of Exemplary Compound Ia-15

0.93 g (3.67 mmol) of zinc acetate dihydrate was dissolved in 50 ml of methanol, and the solution was stirred at room temperature. Thereafter, 3.55 g (3.67 mmol) of the intermediate 11 obtained by the above-described method was added thereto, and the mixture was stirred at room temperature for 2 hours. The precipitated crystal was filtered, washed with 10 ml of methanol and dried, whereby 3.8 g (yield: 95.5%) of an exemplary compound Ia-15 was obtained.

Details of $^1$H-NMR (DMSO-d$_6$) were as follows: δ=9.16-7.62 (br, 7H); 7.52-7.15 (br, 5H); 6.85-6.81 (br, 1H); 5.94-5.91 (br, 2H); 3.31-3.26 (s, 3H); 3.25-3.12 (br, 1H); 2.02-1.99 (br, 2H); 1.28-1.03 (br, 4H); 0.87-0.77 (s, 18H); 0.72-0.66 (d, 3H); and 0.56-0.33 (br, 2H).

The molar absorption coefficient (ε) of each of the obtained compounds was measured in an ethyl acetate solution using a spectrophotometer (trade name: UV-2400PC; manufactured by Shimadzu Corporation). The absorbance (Abs) at 450 nm was evaluated by normalizing the absorbance at a maximum absorption wavelength (λmax) to 1.0. Measurement of the maximum absorption wavelength (λmax) of the exemplary compound Ia-15 was 558 nm was performed, and it was found that the molar absorption coefficient (ε) thereof was 91,000. The measurement results of the absorbance (Abs value), maximum absorption wavelength (λmax), and molar absorption coefficient (ε) are shown in Table 1.

Synthesis of Exemplary Compound Ib-15

0.93 g (3.67 mmol) of zinc acetate dihydrate was dissolved in 50 ml of methanol, and the resultant was stirred at room temperature. Thereafter, 3.77 g (3.67 mmol) of the intermediate 12 obtained by the above-described method was added thereto, and the mixture was stirred at room temperature for 2 hours. The precipitated crystal was filtered, washed with 10 ml of methanol and dried, whereby 3.8 g (yield: 95%) of an exemplary compound Ib-15 was obtained.

Details of $^1$H-NMR (DMSO-d$_6$) were as follows: δ=8.0-7.78 (br, 7H); 7.52-7.15 (br, 10H); 6.66-6.52 (br, 1H); 5.96-5.94 (br, 2H); 3.23-3.12 (br, 1H); 2.02-1.99 (br, 2H); 1.28-1.03 (br, 4H); 0.87-0.77 (s, 18H); 0.72-0.66 (d, 3H); and 0.55-0.32 (br, 2H).

Measurement of the maximum absorption wavelength (λmax) and the molar absorption coefficient (ε) was performed similarly to the above, and it was revealed that the maximum absorption wavelength (λmax) of the exemplary compound Ib-15 in ethyl acetate was 562 nm and the molar absorption coefficient (ε) thereof was 87,100.

Synthesis of Exemplary Compound IIa-6

0.55 g (2.5 mmol) of zinc acetate dihydrate was dissolved in 30 ml of methanol, and the solution was stirred at room temperature. Thereafter, 2.4 g (2.28 mmol) of the intermediate 13 obtained by the above-described method was stirred at room temperature for 1 hour. The precipitated crystal was filtered, washed with 10 ml of methanol and dried, whereby 2.23 g (yield: 86.4%) of an exemplary compound IIa-6 was obtained.

Details of $^1$H-NMR (CDCl$_3$) were as follows: δ=11.14-11.11 (br, 2H); 8.42 (s, 2H); 8.24-8.21 (d, 2H); 7.88-7.86 (d, 2H); 7.76-7.71 (t, 2H); 6.75 (s, 1H); 6.1 (br, 2H); 2.55 (s, 6H); 1.78-1.72 (br, 4H); 1.25-1.12 (br, 8H); 0.94 (s, 36H); and 0.74-0.67 (br, 2H).

Measurement of the maximum absorption wavelength (λmax) and the molar absorption coefficient (ε) was performed similarly to the above, and it was revealed that the maximum absorption wavelength (λmax) of the exemplary compound IIa-6 in ethyl acetate was 552 nm and the molar absorption coefficient (ε) thereof was 106,300.

Synthesis of Exemplary Compound IIb-6

0.31 g (1.43 mmol) of zinc acetate dihydrate was dissolved in 25 ml of methanol, and the resultant was stirred at room temperature. Thereafter, 1.55 g (1.32 mmol) of the intermediate 14 obtained by the above-described method was added thereto, and the mixture was stirred at room temperature for 1 hour. The precipitated crystal was filtered, washed with 10 ml of methanol and dried, whereby 1.2 g (yield: 72.3%) of an exemplary compound IIb-6 was obtained.

Details of $^1$H-NMR (CDCl$_3$) were as follows: δ=11.52-11.46 (br, 2H); 8.35 (s, 2H); 8.14-8.13 (d, 2H); 7.88-7.85 (d, 2H); 7.74-7.70 (t, 2H); 7.31-7.11 (10H); 6.84 (s, 1H); 6 (br, 2H); 1.71-1.68 (br, 4H); 1.26-1.15 (br, 8H); 0.94 (s, 36H); and 0.72-0.66 (br, 2H).

Measurement of the maximum absorption wavelength (λmax) and the molar absorption coefficient (ε) was performed similarly to the above, and it was revealed that the maximum absorption wavelength (λmax) of the exemplary compound IIb-6 in ethyl acetate was 560 nm and the molar absorption coefficient (ε) thereof was 114,000.

Synthesis Example 2

By the method similar to the reaction scheme in Synthesis Example 1 above, the exemplary compounds (dipyrromethene metal complex compounds or tautomers thereof) shown in Table 1 were synthesized. The identification of the compounds and the measurement of the maximum absorption wavelength (λmax) and the molar absorption coefficient (ε) of the compounds were performed similarly to Synthesis Example 1 above. The measurement results are shown in Table 1.

TABLE 1

| Exemplary compound | λmax | ε | Abs value at 450 nm when normalized to Abs = 1.0 at λmax |
|---|---|---|---|
| Ia-12 | 560 | 81,400 | 0.0154 |
| Ia-14 | 560 | 87,600 | 0.0112 |
| Ia-15 | 558 | 91,000 | 0.091 |
| Ia-23 | 558 | 83,200 | 0.0099 |
| Ia-35 | 559 | 90,100 | 0.0106 |
| Ia-38 | 558 | 79,400 | 0.0191 |
| Ib-14 | 561 | 85,200 | 0.0105 |
| Ib-15 | 562 | 87,100 | 0.0089 |
| Ib-20 | 563 | 88,700 | 0.0142 |
| Ib-35 | 562 | 80,500 | 0.0173 |
| Ib-40 | 562 | 95,600 | 0.0082 |
| Ib-41 | 562 | 76,500 | 0.0195 |
| Ib-46 | 560 | 66,100 | 0.0186 |
| Ib-49 | 566 | 91,500 | 0.0116 |
| Ib-53 | 563 | 100,500 | 0.0082 |
| Ib-59 | 559 | 93,900 | 0.0083 |
| Ib-61 | 558 | 89,100 | 0.0101 |
| Ib-69 | 557 | 99,200 | 0.0111 |
| Ib-75 | 564 | 106,400 | 0.0099 |
| IIa-6 | 552 | 106,300 | 0.0127 |
| IIa-7 | 554 | 111,800 | 0.0089 |
| IIa-13 | 550 | 121,300 | 0.0084 |
| IIa-14 | 551 | 100,100 | 0.0114 |
| IIa-15 | 550 | 116,700 | 0.0095 |
| IIa-25 | 555 | 126,900 | 0.0081 |
| IIa-39 | 553 | 109,400 | 0.0119 |
| IIb-6 | 560 | 114,000 | 0.0079 |
| IIb-7 | 563 | 97,100 | 0.0123 |
| IIb-8 | 561 | 92,600 | 0.0135 |
| IIb-13 | 560 | 106,300 | 0.0107 |
| IIb-14 | 560 | 117,400 | 0.01 |
| IIb-20 | 565 | 121,000 | 0.082 |
| IIb-24 | 564 | 100,900 | 0.091 |
| IIb-32 | 559 | 91,400 | 0.0143 |
| IIb-38 | 561 | 105,900 | 0.0099 |
| IIb-40 | 562 | 107,300 | 0.0087 |

As shown in Table 1, each of the dipyrromethene metal complex compounds (including tautomers thereof) of the invention had a high molar absorption coefficient and favorable absorbance at 450 nm. Each of the dipyrromethene metal complex compounds (including tautomers thereof) of the invention had a maximum absorption wavelength within a wavelength region of from 560 nm to 570 nm, which is at a longer wavelength side as compared with those of the compounds (an exemplary compound III-1 (λmax=533 nm), an exemplary compound III-70 (λmax=540 nm), and an exemplary compound III-80 (λmax=540 nm)) described in the specification of U.S. Patent Application Publication No. 2008/0076044.

Example 2

1. Preparation of Resist Solution

The components of the following composition were mixed and dissolved to prepare a resist solution.
Composition

| | |
|---|---|
| Propylene glycol monomethyl ether acetate (PGMEA) | 57.8 parts |
| Binder: 41% solution of benzyl methacrylate/methacrylic acid/2-hydroxyethyl methacrylate (molar ratio = 60/20/20) copolymer in ethyl lactate (EL) | 30.5 parts |
| Dipentaerythritol hexaacrylate | 10.2 parts |
| Polymerization inhibitor: p-methoxyphenol | 0.006 parts |
| Fluorosurfactant: F-475 (trade name, manufactured by DIC Corporation) | 0.80 parts |
| Photopolymerization initiator: TAZ-107 (trade name, manufactured by Midori Kagaku Co., Ltd.; trihalomethyl triazine compound) | 0.58 parts |

2. Preparation of Glass Substrate Having Undercoat Layer

A glass substrate (trade name: Corning 1737, manufactured by Corning Incorporated) was ultrasonicated in 0.5% aqueous NaOH solution, and then washed and dehydrated by baking (200° C./20 minutes).

The resist solution obtained in section 1 above was then applied to the clean glass substrate by a spin coater such that a film thickness was 2.0 µm. Subsequently, the film was heated to dry at 220° C. for 1 hour, whereby a cured film (an undercoat layer) was obtained.

3. Preparation of (Negative-Working) Colored Resist Solution 9.4 g of the resist solution obtained in section 1 above and 0.35 g of the exemplary compound Ia-12 synthesized above (a compound represented by Formula (4): dipyrromethene complex compound) were mixed and dissolved, whereby a colored resist solution (a negative-working ultraviolet-sensitive colored curable composition) was obtained.

4. Formation of Resist Film

The colored resist solution obtained in section 3 above was applied to an undercoat layer side of the glass substrate having an undercoat layer obtained in section 2 above by a spin coater such that a film thickness was 1.0 µm. Subsequently, the film was pre-baked at 100° C. for 120 sec, whereby a monochromatic color filter was obtained.

5. Evaluation

The storage stability of the colored resist solution prepared above, and the spectroscopic property (transmittance), heat resistance and light-fastness of a coating film formed on a glass substrate using the colored resist solution were evaluated. Evaluation results are shown in Table 2.

5-1. Storage Stability

The colored resist solution was stored for one month at room temperature, and then degree of precipitation was visually observed. The storage stability was evaluated according to the following criteria.

Criteria
A: No precipitation was observed
B: Slight precipitation was observed
C: Precipitation was observed 5-2. Evaluation of Transmittance The transmission spectrum of the color filter obtained above was measured, and the transmittance at 450 nm was evaluated according to the following criteria. The transmittance of the color filter at 450 nm was evaluated by correcting (normalizing) the transmittance at the maximum absorption wavelength of the colorant included in the color filter to 2%. A larger transmittance indicates greater transmission of blue light, which indicates favorable magenta or violet color that can be used in a blue filter.

Criteria
A: Transmittance at 450 nm was 90% or more
B: Transmittance at 450 nm was 80% or more but not more than 90%
C: Transmittance at 450 nm was not more than 80%

5-3. Heat Resistance

A glass substrate having undercoat layer formed by applying the colored resin composition obtained in section 3 above was heat-treated at 100° C. for 1 hour using a hot plate, and the color difference (ΔEab) between before and after the heating was determined by using a chronometer MCPD-1000 (trade name, manufactured by Otsuka Electronics Co., Ltd.). The heat resistance was evaluated according to the following criteria. A smaller ΔEab value indicates better heat resistance.

Criteria
A: ΔEab value was less than 6
B: ΔEab value was from 6 to 10
C: ΔEab value was more than 10

5-4. Light-Fastness

A glass substrate having undercoat layer formed by applying the colored resin composition obtained in section 3 above was irradiated with a xenon lamp at an intensity of 20,000 luxes for 10 hours (equivalent to 200,000 lux·h), and the color difference ΔEab between before and after the irradiation was determined. The light-fastness was evaluated according to the following criteria. A smaller ΔEab value indicates better light-fastness.

Criteria
A: ΔEab value was less than 6
B: ΔEab value was from 6 to 10
C: ΔEab value was more than 10

Examples 3 to 37

Colored resist solutions (negative-working solutions) were prepared in the same manner as Example 2, except that the exemplary compound Ia-12 used as a coloring material in the preparation of the color resist solution in section 3 above was replaced by the equivalent molar amount of each of the exemplary compounds (dipyrromethene metal complex compounds) shown in Table 2, and color filters were produced and evaluated similarly to Example 2. The evaluation results are shown in Table 2.

Comparative Examples 1 to 3

Colored resist solutions (negative-working solutions) were prepared in the same manner as Example 2, except that the exemplary compound Ia-12 used as a coloring material in the preparation of the color resist solution in section 3 above was replaced by each of the compounds (exemplary compounds I-23, III-37, and III-55) described in the specification of U.S. Patent Application Publication No. 2008/0076044 as shown in Table 2, and color filters were produced and evaluated similarly to Example 2. The evaluation results are shown in Table 2.

TABLE 2

| | Exemplary compound | Transmittance at 450 nm | Storage stability | Heat resistance | Light-fastness |
|---|---|---|---|---|---|
| Ex. 2 | Ia-12 | A | A | A | A |
| Ex. 3 | Ia-14 | A | A | A | A |
| Ex. 4 | Ia-15 | A | A | A | A |
| Ex. 5 | Ia-23 | A | A | A | A |
| Ex. 6 | Ia-35 | A | A | A | A |
| Ex. 7 | Ia-38 | A | A | A | A |
| Ex. 8 | Ib-14 | A | A | A | A |
| Ex. 9 | Ib-15 | A | A | A | A |
| Ex. 10 | Ib-20 | A | A | B | B |
| Ex. 11 | Ib-35 | A | A | A | A |
| Ex. 12 | Ib-40 | A | A | B | B |
| Ex. 13 | Ib-41 | A | A | A | A |
| Ex. 14 | Ib-46 | A | B | A | A |
| Ex. 15 | Ib-49 | A | B | A | A |
| Ex. 16 | Ib-53 | A | A | A | A |
| Ex. 17 | Ib-59 | A | A | A | A |
| Ex. 18 | Ib-61 | A | A | A | A |
| Ex. 19 | Ib-69 | A | A | A | A |
| Ex. 20 | Ib-75 | A | A | A | A |
| Ex. 21 | IIa-6 | A | A | A | A |
| Ex. 22 | IIa-7 | A | A | A | A |
| Ex. 23 | IIa-13 | A | A | A | A |
| Ex. 24 | IIa-14 | A | A | A | A |
| Ex. 25 | IIa-15 | A | B | A | A |
| Ex. 26 | IIa-25 | A | B | A | A |
| Ex. 27 | IIa-39 | A | A | A | A |
| Ex. 28 | IIb-6 | A | A | A | A |
| Ex. 29 | IIb-7 | A | A | A | A |
| Ex. 30 | IIb-8 | A | A | A | A |
| Ex. 31 | IIb-13 | A | A | A | A |
| Ex. 32 | IIb-14 | A | A | A | A |
| Ex. 33 | IIb-20 | A | A | A | A |
| Ex. 34 | IIb-24 | A | B | A | A |
| Ex. 35 | IIb-32 | A | A | A | A |
| Ex. 36 | IIb-38 | A | A | A | A |
| Ex. 37 | IIb-40 | A | A | A | A |
| Com. Ex. 1 | I-23 (*1) | A | C | A | A |
| Com. Ex. 2 | III-37 (*1) | A | C | A | A |
| Com. Ex. 3 | III-55 (*1) | A | C | A | A |

Ex.: Example,
Comp. Ex.: Comparative Example
(*1): Compounds described in the specification of U.S. Patent Application Publication No. 2008/0076044

As shown in Table 2, each of the compounds in the Examples had excellent storage stability when prepared in a dye resist solution as compared with Comparative Examples using the known compounds (described in the specification of U.S. Patent Application Publication No. 2008/0076044). More specifically, it is shown that the dipyrromethene complex compounds, such as the exemplary compound Ia-12, as a coloring material in the invention have higher solvent solubility compared with the compounds described in the specification of U.S. Patent Application Publication No. 2008/0076044. In particular, in Examples 2 to 37, in which generally-used propylene glycol monomethyl ether acetate (PGMEA) was used as a solvent for a resist, favorable storage stability was obtained as shown above. Thus, it is thought that the dipyrromethene complex compound of the invention is a dye having a wider variety of uses than the known compounds.

In addition, in the Examples, color films having excellent blue spectral characteristics (color separation abilities) suitable for color filters, as well as having excellent heat resistance and light-fastness, were obtained.

Examples 38 to 73

Application of Resist Solution, Exposure, and Development

Image Forming Process

1. Preparation of Silicon Wafer Substrate Having Undercoat Layer

A 6-inch silicon wafer was heat-treated at 200° C. for 30 minutes using an oven. Subsequently, the resist solution prepared in the section 1 of Example 2 above was applied to the silicon wafer such that dry film thickness of the film was 1.0 μm. Then, the silicon wafer was further heated to dry in an oven at 220° C. for 1 hour to form an undercoat layer, whereby a silicon wafer substrate having an undercoat layer was obtained.

Production of Color Filter

Respective colored resist solutions (a negative-working ultraviolet-sensitive colored curable composition) prepared in Examples 2 to 37 above was applied to the undercoat layer of the silicon wafer having the undercoat layer obtained in section 1 above such that the dry film thickness of the coating film was 0.6 μm., to form a photocurable coating layer. Subsequently, the silicon wafer was heat-treated (prebaking) for 120 sec using a hot plate at 100° C.

Subsequently, an i-line stepper FPA-3000i5+ (trade name, manufactured by Canon Inc.) was used to expose the coating film to light at a wavelength of 365 nm through a patterned mask having a 1.2 μm-square island pattern at various exposure amounts from 100 mJ/cm$^2$ to 2500 mJ/cm$^2$ at an interval of 100 mJ/cm$^2$.

After irradiation, the silicon wafer substrate, on which the irradiated coating film was formed, was placed on a horizontal rotary table of a spin-shower developing apparatus (DW-30 type; manufactured by Chemitronics Co., Ltd.), and subjected to paddle development at 23° C. for 60 sec using a CD-2000 (manufactured by Fujifilm Electronic Materials Co., Ltd.), whereby a blue colored pattern was formed on the silicon wafer substrate.

Each of the 36 types of the silicon wafer substrates on which a colored pattern had been formed was fixed to the horizontal rotary table by a vacuum chuck method. While the silicon wafer substrate was rotated by a rotating apparatus at a rotation speed of 50 rpm, a rinsing treatment was conducted by supplying pure water in a shower from an ejection nozzle positioned above the rotational center of the silicon wafer substrate, and then the silicon wafer substrate was spray-dried, whereby a color filter was obtained.

Each of the obtained blue colored patterns had a favorable rectangular profile suitable for image sensors when a cross-sectioned in a plane parallel to the normal line of the substrate surface.

Example 74

1. Preparation of Positive-Working Ultraviolet-Sensitive Colored Curable Composition The components of the following composition were mixed and dissolved to prepare a positive-working ultraviolet-sensitive colored curable composition.

Composition

| | |
|---|---|
| Ethyl lactate (EL) | 30 parts |
| Resin P-1 (described below) | 3.0 parts |
| Naphthoquinonediazide compound N-1(described below) | 1.8 parts |
| Crosslinking agent: Hexamethoxymethylolated melamine | 0.6 parts |
| Photoacid generator: TAZ-107 (trade name, manufactured by Midori Kagaku Co., Ltd.; trihalomethyl triazine compound) | 1.2 parts |
| Fluorosurfactant: F-475 (trade name, manufactured by DIC Corporation) | 0.0005 parts |
| Exemplary compound Ia-12 synthesized above (a dipyrromethene complex compound represented by Formula (4)) | 0.3 parts |

Evaluation of the storage stability, heat resistance and light-fastness of the positive-working ultraviolet-sensitive colored curable composition prepared above was prepared in the same manner as Example 2, as a result of which the composition showed excellent storage stability and heat resistance and favorable light-fastness.

In addition, a color filter was prepared in the same manner as Example 2, and the spectroscopic property (transmittance) of the color filter was evaluated similarly to Example 2. It was found that a blue color filter having excellent transmittance and color separation properties was obtained.

Hereinafter, resin P-1 and naphthoquinonediazide compound (N-1) above will be described.

Synthesis of Resin P-1

70.0 g of benzyl methacrylate, 13.0 g of methacrylic acid, 17.0 g of 2-hydroxyethyl methacrylate, and 600 g of 2-methoxypropanol were placed in a three-neck flask and a stirrer, a reflux condenser tube, and thermometer were attached to the flask. A catalytic quantity of a polymerization initiator (trade name: V-65, made by Wako Pure Chemical Industries, Inc.) was added thereto at 65° C. in a nitrogen stream, and the solution was stirred for 10 hours. The resin solution obtained was added dropwise to 20 L of ion-exchange water while vigorously stirring, whereby a white powder was obtained. The obtained white powder was dried at 40° C. for 24 hours in a vacuum, whereby 145 g of resin P-1 was obtained. Measurement of the molecular weight of resin P-1 by GPC showed that the weight average molecular weight (Mw) was 28,000, and that the number average molecular weight (Mn) was 11,000.

Synthesis of Naphthoquinonediazide Compound (N-1)

42.45 g of TrisP-PA (made by Honshu Chemical Industry Co., Ld.), 61.80 g of o-naphthoquinonediazide-5-sulfonylchloride, and 300 ml of acetone were placed in a three-neck flask. To the mixture, 24.44 g of triethylamine was added dropwise at room temperature over 1 hour. After the dripping was completed, the mixed solution was stirred for another 2 hours. Then, the reaction solution was poured into a large volume of water while stirring. Precipitated naphthoquinonediazide sulfonic acid ester was collected by suction filtration, and dried in a vacuum at 40° C. for 24 hours, whereby naphthoquinonediazide compound N-1 was obtained.

All publications, patent applications, and technical standards mentioned in this specification are herein incorporated by reference to the same extent as if each individual publication, patent application, or technical standard was specifically and individually indicated to be incorporated by reference.

What is claimed is:

1. A colored curable composition, comprising a crosslinking agent and/or a polymerizable monomer and at least one of a dipyrromethene metal complex compound or a tautomer thereof, wherein the at least one of the dipyrromethene metal complex compound or the tautomer thereof is formed from a fluorine-containing dipyrromethene compound represented by the following Formula (4) or Formula (5):

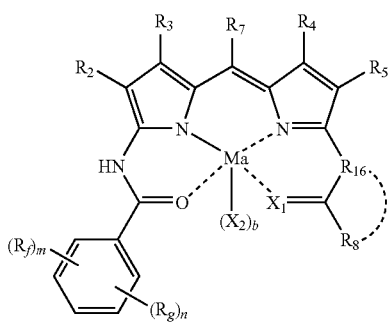

Formula (4)

wherein, in Formula 4, each $R_f$ independently represents a fluorine atom, a fluorine-containing alkyl group having 1 to 4 carbon atoms, a fluorine-containing aryl group, a fluorine-containing alkoxy group having 1 to 4 carbon atoms, a fluorine-containing alkylsulfonamido group having 1 to 4 carbon atoms, or a fluorine-containing arylsulfonamido group; m represents an integer of from 1 to 5; each $R_g$ independently represents a hydrogen atom or a substituent; n represents an integer of from 0 to 4: $R_2$, $R_3$, $R_4$, $R_5$, and $R_7$ each independently represent a hydrogen atom or a substituent; Ma represents a metal or metal compound; $X_1$ represents NY (where, Y represents a hydrogen atom, an alkyl group, an alkenyl group, an aryl group, a heterocyclic group, an acyl group, an alkylsulfonyl group, or an arylsulfonyl group), an oxygen atom, a nitrogen atom, or a sulfur atom; $R_{16}$ represents NR (where, R represents a hydrogen atom, an alkyl group, an alkenyl group, an aryl group, a heterocyclic group, an acyl group, an alkylsulfonyl group, or an arylsulfonyl group) or a carbon atom: & represents a hydrogen atom, an alkyl group, an alkenyl group, an aryl group, a heterocyclic group, an alkoxy group, an acyloxy group, an alkylamino group, an arylamino group, or a heterocyclic amino group; $R_{16}$ and $R_8$ may be linked to each other to form a 5-, 6-, or 7-membered ring; $X_2$ represents a group required for neutralizing the electric charge of Ma; and b represents 0, 1, or 2;

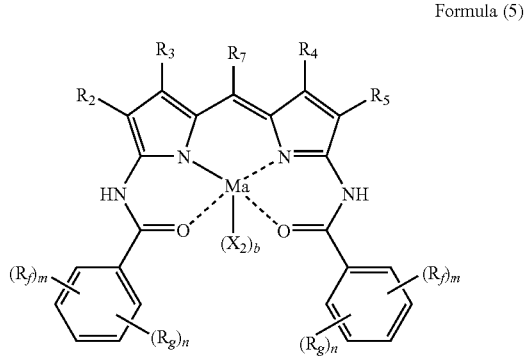

Formula (5)

wherein in Formula 5 each $R_f$ independently represents a fluorine atom, a fluorine-containing alkyl group having 1 to 4 carbon atoms, a fluorine-containing aryl group, a fluorine-containing alkoxy group having 1 to 4 carbon atoms, a fluorine-containing alkylsulfonamido group having 1 to 4 carbon atoms, or a fluorine-containing arylsulfonamido group; m represents an integer of from 1 to 5; each $R_g$ independently represents a hydrogen atom or a substituent; n represents an integer of from 0 to 4; $R_2$, $R_3$, $R_4$, $R_5$, and $R_7$ each independently present a hydrogen atom or a substituent; Ma represents a metal or metal compound; $X_2$ represents a group required for neutralizing the electric charge of Ma; and b represents 0, 1, or 2.

2. The colored curable composition of claim 1, wherein Ma Zn, Co, V=O, or Cu.

3. The colored curable composition of claim 2, wherein Ma is Zn.

4. A color filter formed from the colored curable composition of claim 1.

5. A method for producing a color filter, comprising applying the colored curable composition of claim 1 to form a coating layer, exposing the coating layer through a mask, and developing the coating layer to form a pattern image.

6. The colored curable composition according to claim 1, wherein, in Formula (4) or Formula (5), $R_f$ independently represents a fluorine atom, a fluorine-containing alkyl group having 1 to 4 carbon atoms, or a fluorine-containing alkoxy group having 1 to 4 carbon atoms.

7. The colored curable composition according to claim 1, further comprising a radiation-sensitive compound.

* * * * *